US008921652B2

(12) United States Patent
Liu et al.

(10) Patent No.: US 8,921,652 B2
(45) Date of Patent: Dec. 30, 2014

(54) VEGETABLE OILS AND USES THEREFOR

(75) Inventors: Qing Liu, Giralang (AU); Allan Graham Green, Red Hill (AU); Surinder Pal Singh, Downer (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 281 days.

(21) Appl. No.: 13/011,779

(22) Filed: Jan. 21, 2011

(65) Prior Publication Data

US 2011/0229623 A1 Sep. 22, 2011

Related U.S. Application Data

(63) Continuation-in-part of application No. PCT/AU2009/000930, filed on Jul. 21, 2009.

(60) Provisional application No. 61/135,621, filed on Jul. 21, 2008.

(51) Int. Cl.

| | |
|---|---|
| ***C12N 15/87*** | (2006.01) |
| ***A01H 5/10*** | (2006.01) |
| ***A23D 9/00*** | (2006.01) |
| ***C12N 9/10*** | (2006.01) |
| ***C12N 9/12*** | (2006.01) |
| ***C12P 7/64*** | (2006.01) |
| ***C12N 15/82*** | (2006.01) |

(52) U.S. Cl.

CPC ................ *C12N 9/1288* (2013.01); *A23D 9/00* (2013.01); *C12N 9/1029* (2013.01); *C12P 7/6463* (2013.01); *C12P 7/6472* (2013.01); *C12N 15/8218* (2013.01); *C12N 15/8247* (2013.01)

USPC ............ 800/281; 800/285; 800/298; 800/314

(58) Field of Classification Search

None

See application file for complete search history.

(56) References Cited

U.S. PATENT DOCUMENTS

| | | | | |
|---|---|---|---|---|
| 4,948,811 | A | 8/1990 | Spinner et al. | |
| 5,500,361 | A * | 3/1996 | Kinney | 800/264 |
| 6,100,077 | A | 8/2000 | Sturley et al. | |
| 6,344,548 | B1 | 2/2002 | Farese et al. | |
| 6,432,684 | B1 | 8/2002 | Mukerji et al. | |
| 7,001,771 | B1 | 2/2006 | Morell et al. | |
| 7,045,326 | B2 | 5/2006 | Cases et al. | |
| 7,109,392 | B1 | 9/2006 | Broglie et al. | |
| 7,135,617 | B2 | 11/2006 | Lardizabal et al. | |
| 7,244,599 | B2 | 7/2007 | Tanner et al. | |
| 7,417,176 | B2 | 8/2008 | Lardizabal et al. | |
| 7,521,593 | B2 | 4/2009 | Regina et al. | |
| 7,589,253 | B2 | 9/2009 | Green et al. | |
| 7,619,105 | B2 | 11/2009 | Green et al. | |
| 7,667,114 | B2 | 2/2010 | Morell et al. | |
| 7,700,139 | B2 | 4/2010 | Bird et al. | |
| 7,700,826 | B2 | 4/2010 | Morell et al. | |
| 7,741,532 | B2 | 6/2010 | Lardizabal et al. | |
| 7,790,955 | B2 | 9/2010 | Li et al. | |
| 7,807,849 | B2 | 10/2010 | Singh et al. | |
| 7,812,221 | B2 | 10/2010 | Regina et al. | |
| 7,834,248 | B2 | 11/2010 | Green et al. | |
| 7,834,250 | B2 | 11/2010 | Singh et al. | |
| 7,888,499 | B2 | 2/2011 | Morell et al. | |
| 7,892,803 | B2 | 2/2011 | Tanner et al. | |
| 7,919,132 | B2 | 4/2011 | Regina et al. | |
| 7,932,438 | B2 | 4/2011 | Singh et al. | |
| 7,932,440 | B2 | 4/2011 | Reid et al. | |
| 7,993,686 | B2 | 8/2011 | Bird et al. | |
| 8,049,069 | B2 | 11/2011 | Wu et al. | |
| 8,106,226 | B2 | 1/2012 | Singh et al. | |
| 8,115,087 | B2 | 2/2012 | Regina et al. | |
| 8,158,392 | B1 | 4/2012 | Singh et al. | |
| 8,178,759 | B2 | 5/2012 | Morell et al. | |
| 8,188,336 | B2 | 5/2012 | Li et al. | |
| 8,269,082 | B2 | 9/2012 | Millar et al. | |
| 8,288,572 | B2 | 10/2012 | Singh et al. | |
| 8,501,262 | B2 | 8/2013 | Bird et al. | |

(Continued)

FOREIGN PATENT DOCUMENTS

| | | |
|---|---|---|
| EP | 1806398 | 7/2007 |
| EP | 1837397 | 9/2007 |

(Continued)

OTHER PUBLICATIONS

Dubois et al 2007 109: European Journal of Lipid Science Technology p. 710-732.*
Chapman et al 2001 Journal of the American Oil Chemists Society 78:9 p. 941-947.*
Sheikh et al 2002 Pakistan Journal of Applied Sciences 2:1 p. 97-99.*
International Search Report issued on Sep. 8, 2009 by the International Searching Authority (ISA/US) in connection with International Application No. PCT/AU2006/000930.
U.S Appl. No. 13/093,252, filed Apr. 25, 2011, Singh et al.
U.S Appl. No. 12/989,405, filed May 16, 2011, Singh et al.

(Continued)

*Primary Examiner* — Brent T Page
*Assistant Examiner* — Matthew Keogh
(74) *Attorney, Agent, or Firm* — John P. White; Gary J. Gershik; Cooper & Dunham LLP

(57) ABSTRACT

The specification relates to plants and their seeds and oil obtained therefrom, and to methods of producing same comprising oil having modified fatty acid compositions, such that 28% to 80% of the total fatty acid content in the seedoil is palmitic acid, 0% to 16% is palmitoleic acid, 0% to 4% is C16:2 fatty acid, 3% to 33% is stearic acid, 1% to 40% is oleic acid, 4% to 50% is linoleic acid and 0% to 10% is linolenic acid. The specification describes nucleic acid molecules encoding RNA capable of conferring these properties, in particular, RNA that inhibits expression of an oil biosynthesis gene encoding KASII in seeds of a plant. Genetic constructs and cells comprising the nucleic acid molecules are also described and claimed.

20 Claims, 10 Drawing Sheets

(56) References Cited

U.S. PATENT DOCUMENTS

| | | | |
|---|---|---|---|
| 8,525,917 | B2 | 9/2013 | Singh et al. |
| 8,530,724 | B2 | 9/2013 | Whitelaw et al. |
| 2002/0104124 | A1 | 8/2002 | Green |
| 2004/0221335 | A1 | 11/2004 | Shewmaker et al. |
| 2005/0106697 | A1 | 5/2005 | Cases et al. |
| 2005/0262588 | A1 | 11/2005 | Dehesh et al. |
| 2006/0053512 | A1 | 3/2006 | Bao et al. |
| 2006/0094088 | A1 | 5/2006 | Picataggio et al. |
| 2006/0206963 | A1 | 9/2006 | Voelker et al. |
| 2008/0268539 | A1 | 10/2008 | Singh et al. |
| 2009/0308041 | A1 | 12/2009 | Whitelaw et al. |
| 2010/0184130 | A1 | 7/2010 | Koprowski et al. |
| 2010/0221400 | A1 | 9/2010 | Chapman et al. |
| 2011/0015415 | A1 | 1/2011 | Singh et al. |
| 2011/0054198 | A1 | 3/2011 | Singh et al. |
| 2011/0190521 | A1 | 8/2011 | Damcevski et al. |
| 2011/0218348 | A1 | 9/2011 | Zhou et al. |
| 2011/0223311 | A1 | 9/2011 | Liu et al. |
| 2011/0314725 | A1 | 12/2011 | Petrie et al. |
| 2013/0164798 | A1 | 6/2013 | Vanhercke et al. |

FOREIGN PATENT DOCUMENTS

| | | |
|---|---|---|
| EP | 1837397 | 7/2008 |
| EP | 1944375 | 7/2008 |
| WO | WO 98/55631 | 12/1998 |
| WO | WO 99/49050 A2 | 9/1999 |
| WO | WO 99/67268 | 12/1999 |
| WO | WO 99/67403 | 12/1999 |
| WO | WO 00/01713 | 1/2000 |
| WO | WO 00/11176 | 3/2000 |
| WO | WO 00/32756 | 6/2000 |
| WO | WO 00/32793 | 6/2000 |
| WO | WO 00/36114 | 6/2000 |
| WO | WO 00/66750 | 10/2000 |
| WO | WO 00/66750 A1 | 10/2000 |
| WO | WO 00/66749 | 11/2000 |
| WO | WO 00/60095 | 12/2000 |
| WO | WO 2004/011671 | 2/2004 |
| WO | WO 2005/003322 | 1/2005 |
| WO | WO 2005/063988 | 7/2005 |
| WO | WO 2005/103253 | 11/2005 |
| WO | WO 2005/103253 A1 | 11/2005 |
| WO | WO 2007/103738 | 9/2007 |
| WO | WO 2008/025068 A1 | 3/2008 |
| WO | WO 2008/025068 | 6/2008 |
| WO | WO 2008/130248 | 10/2008 |
| WO | WO 2008/157226 | 12/2008 |
| WO | WO 2008/157827 | 12/2008 |
| WO | WO 2009/027335 | 3/2009 |
| WO | WO 03/078639 | 9/2009 |
| WO | WO 2009/129582 | 10/2009 |
| WO | WO 2009/129582 A1 | 10/2009 |
| WO | WO 2009/143397 | 11/2009 |
| WO | WO 2010/009499 | 1/2010 |
| WO | WO 2010/009500 | 1/2010 |
| WO | WO 2010/057246 | 5/2010 |
| WO | WO 2010/057246 A1 | 5/2010 |
| WO | WO 2012/000026 | 1/2012 |

OTHER PUBLICATIONS

U.S Appl. No. 13/129,940, filed May 18, 2011, Petrie et al.

U.S Appl. No. 13/011,773, filed Jan. 21, 2011, Liu et al.

U.S Appl. No. 13/171,032, filed Jun. 28, 2011, Petrie et al.

International Preliminary Report issued on Jan. 25, 2011 by the International Searching Authority (ISA/US) in connection with International Application No. PCT/AU2006/000930.

Written Opinion issued on Aug. 18, 2009 by the International Searching Authority (ISA/US) in connection with International Application No. PCT/AU2006/000930.

Bäumlein, H., et al., (1991) "A Novel Seed Protein Gene From Vicia faba is Developmentally Regulated in Transgenic Tobacco and *Arabidopsis* Plants," Molecular and General Genetics, 225(3): 459-467.

Domergue et al., In vivo characterization of the first acyl-CoA $\Delta^6$ -desaturase from a member of the plant kingdom, the microalga *Ostreococcus tauri*, Biochem J. 2005, 389, 483-490.

Lee, M., et al., (1998) "Identification of Non-theme Diiron Proteins That Catalyze Triple Bond and Epoxy Group Formation," Science, 280(5365): 915-918.

Needleman, S. B., & Wunsch, C. D. (1970). A general method applicable to the search for similarities in the amino acid sequence of two proteins. J. Mol. Biol., 48, 443-453.

Stålberg, K., et al., (1993) "Deletion Analysis of A 2S Seed Storage Protein Promoter of *Brassica napus* in Transgenic Tobacco," Plant Molecular Biology, 23(4): 671-683.

Trautwein, E.A., (2001) "n-3 Fatty Acids—Physiological and Technical Aspects for Their Use in Food," European Journal of Lipid Science and Technology, 103 (1) : 45-55.

Valvekens, D., et al., (1988) "*Agrobacterium tumetaciens* —Mediated Transformation of *Arabidopsis thaliana* Root Explants by Using Kanamycin Selection," Proceedings of the National Academy of Sciences of the United States of America, 85(15) 5536-5540.

van de Loo, F. J., Broun, P., Turner, S., & Somerville, C. (Jul. 1995). An oleate 12-hydroxylase from *Ricinus communis* L. is a fatty acyl desaturase homolog. Proc. Natl. Acad. Sci. USA, 92, 6743-6747.

File History of U.S. Patent No. 7,807,849, Singh et al., issued Oct. 5, 2010 (U.S. Appl. No. 11/112,882, filed Apr. 22, 2005).

File History of U.S. Patent Application Publication No. 2011/0015415, Singh, et al., published Jan. 20, 2011 (U.S. Appl. No. 12/661,978, filed Mar. 26, 2010).

File History of U.S. Patent No. 7,834,250, issued Nov. 16, 2010 (U.S. Appl. No. 11/587,092, filed Oct. 20, 2006) (Singh et al.).

File History of U.S. Patent No. 7,932,438, Singh et al., issued (U.S. Appl. No. 12/945,708, filed Nov. 12, 2010) (Singh et al.).

File History of U.S. Patent Application Publication No. 2011/0190521, published Aug. 4, 2011 (U.S. Appl. No. 12/310,645, filed Feb. 16, 2011) (Damcevski et al.).

File History of U.S. Appl. No. 12/989,405, filed May 16, 2011 (Zhou et al.).

File History of U.S. Patent No. 7,589,253, issued Sep. 15, 2009 (U.S. Appl. No. 09/981,124, filed Oct. 17, 2011) (Green et al.).

File History of U.S. Patent No. 7,834,248, issued Nov. 16, 2010 (U.S. Appl. No. 11/699,817, filed Jan. 30, 2007) (Green et al.).

File History of U.S. Patent Publication No. 2011-0314725, Petrie et al., published Dec. 29, 2011 (U.S. Appl. No. 13/171,032, filed Jun. 28, 2011).

Liu et al. (2002) "High-Stearic and High-Oleic Cottonseed Oils Produced by Hairpin RNA-Mediated Post-Transcriptional Gene Silencing." Plant Physiology, 129(4):1732-1743.

Taira et al. (1988) "Fatty Acid Composition of Indica Sinica Javanica and Japonica Groups of Nonglutinous Brown Rice" Journal of Agricultural and Food Chemistry; vol. 36 No. 1, 45-47.

Cherry, (1983) "Cottonseed Oil" J. Am, Oil Chem. Soc. 60: 360-367.

Dowd et al., (2004) "Gene Expression Profile Changes in Cotton Root and Hypocotyl Tissues in Response to Infection with *Fusarium oxysporum* f. sp. vasinfectum" Molecular Plant-Microbe Interactions. 17: 654-667.

Folch et al., (1957) "A Simple Method for the Isolation and Purification of total Lipides From Animal Tissues" J. Biol. Chem. 226: 497.

Fuller et al., (1966) "A Gas Chromatographic Method for Continuous Accelerated Study of $O_2$ Uptake in Fats" JAOCS. 43: 477-478.

Hutchins et al., (1968) "A New Process for the Selective Hydrogenation Cyclopropenoids in Cottonseed Oil" Journal of American Oil Chemists Society 45: 397-399.

Kargiotidou et al., (2008) "Low temperature and light regulate delta 12 fatty acid desaturases (FAD2) at a transcriptional level in cotton (*Gossypium hirsutum*)" Journal of Experimental Botany 2008 59(8): 2043-2056.

Liu et al., (1999) "Cloning and Sequence Analysis of a Novel Member (Accession No. Y10112) of the Microsomal w-6 Fatty Acid Desaturase Family from Cotton" Plant Physiol. (PGR 99-063) 120: 339.

Liu et al., (1999) "Molecular cloning and expression of a cDNA encoding a microsomal w-6 fatty acid desaturase from cotton (*Gossypium hirsutum*)" Australian Journal of Plant Physiology 26: 101-106.

(56) References Cited

OTHER PUBLICATIONS

Mojovic et al., (1993) "*Rhizopus arrhizus* lipase-catalyzed interesterification of the midfraction of palm oil to a cocoa butter equivalent fat" Enzyme Microb Technol. 15: 438-443.
Mounts et al., (1998) "Effect of Altered Fatty Acid Composition on Soybean Oil Stability" J Am. Oil Chem. Soc. 65: 624-628.
O'Brien, (2002) Cottonseed Oil, in: F.D. Gunstone (Ed.) Vegetable Oils in Food Technology: Composition, Properties and Uses. Blackwell Publishing, Oxford, pp. 203-230.
Pirtle et al., (2001) "Molecular cloning and functional expression of the gene for a cotton v-12 fatty acid desaturase (FAD2)" Biochim. Biophys. Acta 1522: 122-129.
Shenstone and Vickery, (1961) "Occurrence of Cyclo-Propene Acids in Some Plants of the Order Malvales" Nature 190: 68-169.
U.S. Appl. No. 13/171,032, filed Jun. 28, 2011, Petrie et al.
Aghoram, K., Wilson, R.F., Burton, J.W., Dewey, R.E. 2006. A mutation in a 3-keto-acyl-acp synthase ii gene is associated with elevated palmitic acid levels in soybean seeds. Crop Sci. 46:2453-2459.
International Preliminary Report on Patentability issued on Jan. 14, 2009 in connection with International Application No. PCT/AU2007/000977.
Jan. 9, 2013 Office Action issued in connection with U.S. Appl. No. 13/011,773.
Feb. 11, 2013 Response filed in connection with U.S. Appl. No. 13/011,773.
Apr. 9, 2013 Office Action issued in connection with U.S. Appl. No. 13/011,773.
Jul. 1, 2011 Office Action issued in connection with U.S. Appl. No. 12/309,276.
Sep. 1, 2011 Response filed in connection with U.S. Appl. No. 12/309,276.
Nov. 4, 2011 Office Communication issued in connection with U.S. Appl. No. 12/309,276.
Dec. 5, 2011 Response filed in connection with U.S. Appl. No. 12/309,276.
Jan. 12, 2012 Office Action issued in connection with U.S. Appl. No. 12/309,276.
Feb. 6, 2012 Petition filed in connection with U.S. Appl. No. 12/309,276.
Mar. 26, 2012 Decision on Petition issued in connection with U.S. Appl. No. 12/309,276.
Aug. 3, 2012 Office Action issued in connection with U.S. Appl. No. 12/309,276.
Dec. 3, 2012 Response filed in connection with U.S. Appl. No. 12/309,276.
Jan. 17, 2013 Office Action issued in connection with U.S. Appl. No. 12/309,276.
Apr. 17, 2013 Response filed in connection with U.S. Appl. No. 12/309,276.
May 6, 2013 Notice of Allowance issued in connection with U.S. Appl. No. 12/309,276.
Abdullah, R., Cocking, E. C., & Thompson, J. A. (1986) "Efficient plant regeneration from rice protoplasts through somatic embryogenesis" Biotechnology, 4, 1087-1090.
Agarwal et el. (2003) "Cottonseed Oil Quality, Utilization and Processing" CICR Technical Bulletin No. 25, pp. 1-16.
Akagi et al. (1995) "Nucleotide Sequence of a Stearoyl-Acel carrier Protein Desaturase cDNA from Developing Seeds of Rice" Plant Physiol. 108, 845-846.
Almeida and Allshire, (2005) "RNA silencing and genome regulation." Trends in Cell Biology, 15:251-258.
Anai et al. (2003) "Improvement of rice (*Oryza sativa* L.) seed oil quality through introduction of a soybean microsomal omega-3 fatty acid desaturase gene" Plant Cell Rep. 21,988-992.
Ascherio and Willett (1997) "Health effects of trans fatty acids" Am. J. Clin. Nutr. 66: 1006S-1010S.
Bao and Ohlrogge, (1999) "Supply of Fatty Acid is One Limiting Factor in the Accumulation of Triacylglycerol in Developing Embryos." Plant Physiology, 120:1057-1062.
Bligh and Dyer (1959) "A Rapid Method of Total Lipid Extraction and Purification" Canadian Journal of Biochemistry and Physiology 37:911-917.
Boggs et al. (1964) "Relation of Hexanal in Vapor Above Stored Potato Granules to Subjective Flavor Extimates." J. Food Sci. 29: 487-489.
Bonanome and Grundy (1988) "Effect of Dietary Stearic Acid on Plasma Cholesterol and Lipoprotein Levels" N. Engl. Med. 318:1244-1248.
Brandt et al., (1985) "Primary Structure of a B1 Hordein Gene from Barley" Carlsberg Res. Commun., 50:333-345.
Buhr et al. (2002) "Ribozyme termination of RNA transcripts down-regulate seed fatty acid genes in transgenic soybean" Plant J. 30: 155-163.
Cases at al., (1998) "Identification of a gene encoding an acyl CoA:diacylglycerol acyltransferase, a key enzyme in triacylglycerol synthesis" PNAS 95:13018-13023.
Cases et al., (2001) "Cloning of DGAT2, a second mammalian diacylglycerol acyltransferase, and related family members" J. Biol. Chem. 276(42):38870-38876.
Cao et al., (2003) "Properties of the Mouse Intestinal Acyl-CoA:Monoacylglycerol Acyltransferase, MGAT2" The Journal of Biological Chemistry, 278(28)23657-25669.
Champagne et al. (1995) "Stabilization of Brown Rice Products Using Ethanol Vapors as an Antioxidant Delivery System" Cereal Chem 72:255-258.
Chang et al., (1978) "Chemical Reactions Involved in the Deep-Fat Frying of Foods." Journal of American Oil Chemists' Society, 55:718-727.
Cheng et al., (2003) "Identification of Acyl Coenzyme A:Monoacylglycerol Acyltransferase 3, an Intestinal Specific Enzyme Implicated in Dietary Fat Absorption." The Journal of Biological Chemistry, 278(126):13611-13614.
Choudhury et al. (1980) "Lipids in Developing and Mature Rice Grain" Phytochemistry 19: 1063-1069.
Cicero et al. (2001) "Rice bran oil and [gamma]-oryzanol in the treatment of hyperlipoproteinaemias and other conditions" Phytotherapy Research; vol. 15 No. 4, 277-289.
Clapp et al., (1993) "The 16-Kilodalton N-Terminal Fragment of Human Prolactin is a Potent Inhibitor of Angiogenesis" Endocrinology, 133(3):1292-1299.
Calot et al., (1987) "Localization of sequences in wheat endosperm protein genes which confer tissue-specific expression in tobacco" The EMBO Journal, 6(12):3559-3564.
Comai et al., (2004) "Efficient discovery of DNA polymorphisms in natural populations by Ecotilling" The Plant Journal, 37:778-786.
Dougherty et al. (1995) "Effects of diets containing high or low amounts of stearic acid on plasma lipoprotein fractions and fecal fatty acid excretion of men" Am. J. Clin. Nutr. 61:1120-1128.
Dulermo and Nicaud (2011) "Involvement of the G3P shuttle and β-oxidation pathway in the control of TAG synthesis and lipid accumulation in *Yarrowia lipolytica*" Metab. Eng. 13:482-491.
Goffman et al., (2003) "Genetic Diversity for Lipid Content and Fatty Acid Profile in Rice Bran," Journal of the American Oil Chemists' Society 80:485-490.
Ha (2005) "Bioactive components in rice bran oil improve lipid profiles in rats fed on high-cholesterol diet" Nutrition research 25, 597-606.
Haseloff, J. and Gerlach, W.L., (1988) "Simple RNA Enzymes With New and Highly Specific Endoribonuclease Activities," Nature, 334: 585-591.
Henikoff et al., (2004) "Tilling. Traditional Mutagenesis Meets Functional Genomics." Plant Physiology, 2004, 135:630-636.
Hu et al. (1997) "Dietary Fat Intake and the Rist of Coronary Heart Disease in Women." N. Engl. J. Med. 337: 1491-1499.
Jako et al., (2001) "Seed-Specific Over-Expression of an *Arabidopsis* cDNA Encoding a Diacylglycerol Acyltransferase Enhances Seed Oil Content and Seed Weight" Plant Physiology, 126:861-874.
Jennings and Akoh (2000) "Lipase-Catalyzed Modification of Rice Bran Oil to Incorporate Capric Acid." Journal of Agricultural and Food Chemistry, 48:4439-4443.

(56) References Cited

OTHER PUBLICATIONS

Jones et al. (1995) "Palmitoyl-Acyl Carrier Protein (ACP) Thioesterase and the Evolutionary Origin of Plant Acyl-ACP Thioesterases." Plant Cell 7: 359-371.
Klahre et al. (2002) "High molecular weight RNAs and small interfering RNAs induce systemic posttranscriptional gene silencing in plants." PNAS 99(18): 11981-11986.
Lemieux B., (2000) "High Throughput Single Nucleotide Polymorphism Genotyping Technology." Current Genomics, 2000, 1:301-311.
Leonard et al. (1997) "*Cuphea wrightii* thioesterases have unexpected broad specificities on saturated fatty acids." Plant Molecular Biology, vol. 34, Issue 4: 669-679.
Li et al., (1997) "Comparison of promoters and selectable marker genes for use in Indica rice transformation." Molecular Breeding, 3:1-14.
Liu et al, (2002) "High-Oleic and High-Stearic Cottonseed Oils: Nutritionally Improved Cooking Oils Developed Using Gene Silencing." J. Am. Coll. Nutr. 21: 205S-211S.
Lu et al. (1993) "High efficiency retroviral mediated gene transduction into single isolated immature and replatable CD343+ hematopoietic stem/progenitor cells from human umbilical cord blood." J. Exp. Med., 178, 2089-2096.
Mensink and Katan (1990) "Effect of Dietary Trans Fatty Acids on High-Density and Low-Density Lipoprotein Cholesterol Levels in Healthy Subjects." N. Engl. J. Med. 323: 439-445.
Mikkilineni and Rocheford (2003) "Sequence variation and genomic organization of fatty acid desaturase-2 (fad2) and fatty acid desaturase-6 (fad6) cDNAs in maize." Theor. Applied Genetics, 106, 1326-1332.
Millar and Waterhouse (2005) "Plant and animal microRNAs: similarities and differences." Funct Integr Genomics, 2005, 5:129-135.
Miquel et al. (1992) "*Arabidopsis* mutants deficient in polyunsaturated fatty acid synthesis: Biochemical and genetic characterization of a plant oleoyl-phosphatidylcholine desaturase" Journal of Biological Chemistry; vol. 267 No. 3, 1502-1509.
Moghadasian and Frohlich (1999) "Effects of Dietary Phytosterols on Cholesterol Metabolism and Atherosclerosis: Clinical and Experimental Evidence." Am. J. Med. 107: 588-94.
Morrison (1988) "Lipids in Cereal Starches: A Review." J Cereal Sci. 8:1-15.
Most et al. (2005) "Rice bran oil, not fiber, lowers cholesterol in humans." Am J Clin Nutr 81:64-8.
Nielsen et al. (2004) Formation of Volatile Compounds in Model Experiments with Crude Leek (*Allium ampeloprasum* Var. Lancelot) Enzyme Extract and Linoleic Acid or Linolenic Acid. Journal of Agricultural and Food Chemistry 52:2315-2321.
Noakes and Clifton (1998) "Oil blends containing partially hydrogenated or interesterified fats: differential effects on plasma lipids." Am. J. Clin. Nutr. 98: 242-247.
O'Brien (2005) "Cottonseed Oil" Bailey's Industrial Oil and Fat Products, 6th Edition, edited by Fereidoon Shahidi.
Ohlrogge and Jaworski (1997) "Regulation of Fatty Acid Synthesis. Annu Rev Plant Physiol Plant Mol Biol." 48:109-136.
Perriman, R., et al., (1992) "Extended Target-Site Specificity for a Hammerhead Ribozyme," Gene, 113(2): 157-163.
Pirtle et al. (1999) "Characterization of a Palmitoyl-Acyl Carrier Protein Thioesterase (FatB1) in Cotton" Plant Cell Physiology 40:2 p. 155-163.
Radcliffe et al. (1997) "Serum Lipids in Rats Fed Diets Containing Rice Bran Oil or High-Linolenic Acid Safflower Oil." Biochemical Archives 13:87-95.
Resurreccion et al. (1979) "Nutrient Content and Distribution in Milling Fractions of Rice Grain." Journal of the Science of Food and Agriculture, 30: 475-481.
Roche and Gibney (2000) "Effect of long-chain n-3 polyunsaturated fatty acids on fasting and postprandial triacylglycerol metabolism." Am. J. Clin. Nutr. 71: 232S-237S.
Rukmini and Raghuram (1991) "Nutritional and Biochemical Aspects of the Hypolipidemic Action of Rice Bran Oil: A Review." Journal of the American College of Nutrition 10(6):593-601.
Senior I.J., (1998) "Uses of Plant Gene Silencing." Biotechnology & Genetic Engineering Reviews, Ed. Tombs, M.P., 15:79-119.
Shin et al. (1986) "Correlation Between Oxidative Deterioration of Unsaturated Lipid and n-Hexanal during Storage of Brown Rice." J. Food Sci. 51:460-463.
Shippy, R., et al., (1999) "The Hairpin Ribozyme—Discovery, Mechanism, and Development for Gene Therapy," Molecular Biotechnology, 12(1): 117-129.
Sivaraman et al. (2004) "Development of high oleic and low linoleic acid transgenics in a zero erucic acid *Brassica juncea* L. (Indian mustard) line by antisense suppression of the fad2 gene" Molecular Breeding, Kluwer Academic Publishers, DO; vol. 13 No. 1, 365-375.
Slade and Knauf, (2005) "Tilling moves beyond functional genomics into crop improvement." Transgenic Research, 14:109-115.
St Angelo et al. (1980) "Identification of Lipoxygenase-Linoleate Decomposition Products by Direct Gas Chromatography-Mass Spectrometry." J Lipids 1:45-49.
Stoutjesdijk et al. (2002) "hpRNA-mediated targeting of the *Arabidopsis* FAD2 gene gives highly efficient and stable silencing" Plant Physiology, American Society of Plant Physiologists, Rockville, MD, US; vol. 129, 1723-31.
Stoutjesdijk et al., (2000) "High-oleic acid Australian *Brassica napus* and *B. juncea* varieties produced by co-suppression of endogenous Δ12-desaturases." Biochem. Soc. Trans. 28: 938-940.
Suzuki et al. (1999) "Volatile Components in Stored Rice [*Oryza sativa* (L.)] of Varieties with and without Lipoxygenase-3 in Seeds." J. Agric. Food Chem. 47: 1119-1124.
Taira et al. (1989) "Fatty Acid Composition of Indica-Types and Japonica-Types of Rice Bran and Milled Rice" Journal of the American Oil Chemists' Society; vol. 66 No. 9, 1326-1329.
Taira et al. (1986) "Lipid Content and Fatty-Acid Composition of Indica and Japonica Types of Nonglutinous Brown Rice" Journal of Agriculture and Food Chemistry; vol. 34 No. 3, 542-545.
Thelen and Ohlrogge (2002) "Metabolic Engineering of Fatty Acid Biosynthesis in Plants." Metabolic Engineering 4: 12-21.
Theriault et al. (1999). "Tocotrienol: A Review of its Therapeutic Potential." Clin. Biochem. 32: 309-19.
Tholstrup et al. (1994) "Fat high in stearic acid favorably affects blood lipids and factor VII coagulant activity in comparison with fats high in palmitic acid or high in myristic and lauric acids." Am. J. Clin. Nutr. 59: 371-377.
Toriyama et al., "Haploid and diploid plant regeneration from protoplasts of anther callus in rice." Theor Appl Genet, 1986, 73:16-19.
Tsugita et al (1983) "Cooking Flavor and Texture of Rice Stored under Different Conditions." Agricultural and Biological Chemistry 47: 543-549.
Tsuzuki et al (2004) "Oxidation Rate of Conjugated Linoleic Acid and Conjugated Linolenic Acid is Slowed by Triacylglycerol Esterification and α-Tocopherol." Lipids 39:475-480.
Voelker et al. (1996) "Genetic engineering of a quantitative trait: metabolic and genetic parameters influencing the accumulation of laurate in rapeseed." Plant J. 9: 229-241.
Wagner et al. (1992) "Coupling of adenovirus to transferrin-polylysine/DNA complexes greatly enhances receptor-mediated gene delivery and expression of transfected genes." Proc. Natl. Acad. Sci. USA, 89, 6099-6103.
Wang et al., (1998) "Improved Vectors for *Agrobacterium tumefaciens*—Mediated Transformation of Monocot Plants." Acta Hort, 1998, 461:401-407.
Waterhouse, P.M., et al., (1998) "Virus Resistance and Gene Silencing in Plants Can Be Induced by Simultaneous Expression of Sense and Antisense RNA," Proceedings of the National Academy of Sciences of the United States of America, 95(23):13959-13964.
Weselake et al. (2009) "Increasing the flow of carbon into seed oil" Biotechnology Advances 27:866-878.
Williams et al. (1999) "Impaired Endothelial Function Following a Meal Rich in Used Cooking Fat." J. Am. Coll. Cardiol. 33:1050-1055.

(56) References Cited

OTHER PUBLICATIONS

Whitelaw et al. (1986) "A Rice FATB Insertional Mutant Exhibits Improved Growth and Reduced Photoinhibition at High Temperatures" Proceedings of the 55th Australian Cereal Chemistry Conference, 55th Australian Cereal Chemistry Conference, Jul. 3-7, 2008, Sydney Australia, Jul. 3, 2005, pates 101-104.
Whitelaw et al., (2004) "Investigation of lipid synthesis in the rice grain: modification of fatty acids in rice bran oil."In C.K. Black, J. F. Panozzo, and G.J. Rebetzke (Eds.), Cereals 2004: Proceedings of the 54th Australian Cereal Chemistry Conference and 11th Wheat Breeders Assembly, 21st-245th Sep. 2004, Canberra ACT, North Melbourne VIC: Cereal Chemistry Division, Royal Australian Chemical Institute, AU (pp. 418-420).
Wu et al. (1994) "A Mutant of Arabiwpsis Deficient in the Elongation of Palmitic Acid" Plant Physiol. 106: 143-150.
Wu et al. (1997) "Low-Temperature Damage and Subsequent Mutant *Arabidopsis* Exposed to Recovery of fab7 2° C." Plant Physiol. 1997) 11 3: 347-356.
Yasumatsu et al. (1966) "Studies on Cereals Part V Stale Flavor of Stored Rice." Agric. Biol. Chem. 30:483-486.
Yen et al., Identification of a gene encoding MGAT1, a monoacylglycerol acyltransferase. PNAS, 2002, 99(13):8512-8517.
Zhou et al. (2002) "Ageing of Stored Rice: Changes in Chemical and Physical Attributes." Journal of Cereal Science 35:65-78.
Zock et al. (1994) "Impact of myristic acid versus palmitic acid on serum lipid and piloprotein levels in healthy women and men." Arterioscler Thromb. 14: 567-575.
Connolly et al. (1998) GenBank Accession No. AC004236, NCBI, pp. 1-11.
Sharma et al., (2003) GenBank Accesion No. AC108870, NCBI, pp. 1-27.
Kim et al., (1999) GenBank Accesion No. AF213480, NCBI, p. 1.
Sasaki et al., (2001) GenBank Accession No. AP004047, NCBI, pp. 1-36.
Sasaki et al., (1999) GenBank Accession No. AP000399, NCBI, pp. 1-33.
Sasaki et al., (2001) Genbank Accession No. AP004236, NCBI, pp. 1-37.
Sasaki et al., (2002) GenBank Accession No. AP005168, NCBI, pp. 1-31.
Sasaki et al., (2002) GenBank Accession No. AP005291, NCBI, pp. 1-38.
Liu et al., (2005) GenBank Accession No. AY574036.
Liu et al., (2005) GenBank Accession No. AY574037.
Liu et al., (2005) GenBank Accession No. AY574038.
U.S. Appl. No. 13/841,641, Vanhercke et al., filed Mar. 15, 2013.
File History of U.S. Patent Publication No. 2011-0314725, Petrie et al., published Dec. 29, 2011 (U.S. Appl. No. 13/171,032.
File History of U.S. Patent Publication No. 2011-0223311, Liu et al., published Sep. 15, 2011 (U.S. Appl. No. 13/011,773, filed Jan. 21, 2011).
File History for U.S. Patent Publication No. 2009-0308041, Whitelaw et al., Dec. 17, 2009 (U.S. Appl. No. 12/309,276, filed Jul. 6, 2009).
File History of U.S. Patent Publication No. 2011-0229623, Liu et al., Sep. 22, 2011 (U.S. Serial No. 13/011,779, filed Jan. 21, 2011).
File History of U.S. Patent Application Publication No. 2013/0164798, Vanhercke et al., published Jun. 27, 2013 (U.S. Appl. No. 13/725,404, filed Dec. 21, 2013).
International Search Report issued on Sep. 8, 2009 in Connection with International Application No. PCT/AU2009/000929.
Written Opinion of the International Search Authority, issued on Sep. 8, 2009 in Connection with International Application No. PCT/AU2009/000929.
International Search Report issued by the International Searching Authority (ISA.AU) on Oct. 25, 2007 in connection with International Application No. PCT/AU2007/000977.
International Preliminary Report on Patentability issued on Jan. 14, 2009 in connection with PCT International Patent Application No. PCT/AU2007/000977.
English Translation of Jun. 26, 2013 Office Action, issued in connection with Chinese Patent Application No. 200980134226.8.
U.S. Appl. No. 14/021,173, filed Sep. 9, 2013 (Whitelaw et al.).
Aug. 8, 2013 Response, filed in connection with U.S. Appl. No. 13/011,773.
Andrianov et al. (2010) *Tobacco as a production platform for biofuel: overexpression of *Arabidopsis* DGAT and LEC2 genes increases accumulation and shifts the composition of lipids in green biomass' Plant Biotech. J. 8:277-287.
Alonso et al. (2010) "Catalytic conversion of biomass to biofuels" Green Chem. 12:1493-1513.
Awai at al., (2006) "A phosphatidic acid-binding protein of the chloroplast inner envelope membrane involved in lipid trafficking" PNAS 103(28):10817-22 .
Bouvier-Nave et al. (2000) "Expression in yeast and tobacco of plant cDNAs encoding acyl CoA:diacylglycerol acyltransferase" European Journal of Biochemistry/FEBS 267:85-96.
Broun et al. (1998) "A bifunctional oleate 12-hydroxylase: desaturase from *Lesquerella fenleri*." The Pant Journal, 13 (2) :201-210.
Burgal et al . , (2008) "Metabolic engineering of hydroxy fatty acid production in plants : RcDGAT2 drives dramatic increases in ricinoleate levels in seed oil" Plant Biotechnology Journal 6 (8) : 819-831.
Cernac and Benning (2004) "WRINKLED1 encodes an AP2/EREB domain protein involved in the control of storage compound biosynthesis in *Arabidopsis*" Plant J. 40:575-585.
Chappell et al (1998) "Vegetable Oil Production: Industry Profile" Preliminary Final Report, EPA contract 68-D4-0099, TRU Project # 7018-54, 1-1-5-26.
Durrett et al. (2008) "Plant triacylglycerols as feedstocks for the production of biofuels" Plant J. 54:593-607.
Eastmond, (2006) "Sugar-Dependent1 Encodes a Patatin Domain Triacylglycerol Lipase That Initiates Storage Oil Breakdown in Germinating *Arabidopsis* Seeds" The Plant Cell, vol. 18, 665-675.
Endalew et al. (2011) "Inorganic heterogeneous catalysts for biodiesel production from vegetable oils" Biomass and Bioenergy 35:3787-3809.
Ghosal et al. (2007) "*Saccharomyces cerevisiae* phospholipid:diacylglycerol acyl transferase (PDAT) devoid of its membrane anchor region is a soluble and active enzyme retaining its substrate specificities" Biochimica et Biophysica Acta 1771:1457-1463.
Gong and Jiang (2011) "Biodiesel production with microalgae as feedstock : from strains to biodiesel" Biotechnol. Lett. 33:1269-1284.
Greenwell et al. (2010) "Placing microalgae on the biofuels priority list: a review of the technological challenges" J. R. Soc. Interface 7:703-726.
Jain et al., (2000) "Enhancement of seed oil content by expression of glycerol-3-phosphate acyltransferase genes" Biochemical Society Transactions 28(6):958-961.
James et al (2010) "Disruption of the *Arabidopsis* CGI-58 homologue produces Chanarin-Dorfman-like lipid droplet accumulation in plants," 107(41):17833-17838 and supporting information pp. 1-3.
Karmakar et al. (2010) "Properties of various plants and animals feedstocks for biodiesel production" Bioresource Technology 101:7201-7210.
Kelly et al., (2011) "Seed Storage Oil Mobilization Is Important But Not Essential for Germination or Seedling Establishment in *Arabidopsis* " Plant Physiology, vol. 157, pp. 866-875.
Kinney (1996) Development of Genetically Engineered Soybean Oils for Food Applications. J. Food Lipids 3: 273-292.
Kodama et al. (1997) Structure, chromosomal location and expression of a rice gene encoding the microsome ω-3 fatty acid desaturase. Plant Molecular Biology 33:493-502.
Kohno-Murase at al. (2006). Production of trans-10, cis-12 conjugated linoleic acid in rice. Transgenic Research 15:95-100.
Kozeil et al. (1996) "Optimizing expression of transgenes with an emphasis on post-transcriptional events." Plant Molecular Biology, 32:393-405.
Langridge et al. , Trends in genetic and genome analysis in wheat: a review. Aust. J. Agric. Res., 2001, 52:1043-1077.

(56) References Cited

OTHER PUBLICATIONS

Lardizabal et al. ( 2001 ) "DGAT2 is a New Diacylglycerol Acyltransferase Gene Family" J. Biol. Chem. 276:38862-38869.
Lardizabal et al. (2008) "Expression of Umbelopsis ramanniana DGAT2A in Seed Increases Oil in Soybean" Plant Physiol. 148: 89-96.
Liu et al. (2010) "Producing biodiesel from high free fatty acids waste cooking oil assisted by radio frequency heating" Fuel 89:2735-2740.
Liu et al. (1997) EMBL Nucleotide Sequence Database as X97016.
Liu et al., Genetic modification of cotton seed oil using inverted-repeat gene-silencing techniques. Biochemical Society Transations, 2000, 28(6):927-929.
Liu et al., (1999) "Cloning and Sequence Analysis of a Novel Member (Accession No. Y10112) of the Microsomal w-6 Fatty Acid Desaturase Family from Cotton" Plant Physiol. (PGR 99-063) 120:339.
Lu et al.,(2011) "New frontiers in oilseed biotechnology: meeting the global demand for vegetable oils for food, feed, biofuel, and industrial applications" Current Opinion in Biotechnology, 22:252-259.
Maher and Bressler (2007) "Pyrolysis of triglyceride materials for the production of renewable fuels and chemicals" Bioresource Technology 98:2351-2368.
O'Brien, (2002) Cottonseed Oil. In: F.D. Gunstone (Ed.) Vegetable Oils in Food Technology: Composition, Properties and Uses. Blackwell Publishing, Oxford, pp. 203-230.
Okuley et al. *Arabidopsis* FAD2 Gene Encodes the Enzyme that is Essential for Polyunsaturated Lipid Synthesis, Plant Cell, 1994, 6:147-158.
Parthibane et al. (2012) "Oleosin is a Bifunctional Enzyme That Has Both Monoacylglycerol Acyltransferase and Phospholipase Activities" J. Biol. Chem. 287:1946-1954.
Perez-Vich et al. (1998) "Determination of Seed Oil Content and Fatty Acid Composition in Sunflower Through the Analysis of Intact Seeds, Husked Seeds, Meal and Oil by Near-Infrared Reflectance Spectroscopy" JAOCS 75:547-555.
Petrie et al. (2012) "Recruiting a New Substrate for Triacylglycerol Synthesis in Plants: The Monoacylglycerol Acyltransferase Pathway" PLoS One 7:e35214.
Pokharkar et al., (2008) "Synthesis and Characterizationof Fatty Acid Methyl Ester by In-Situ Transesterification in *Capparis deciduas* Seed" Leonardo Electronic Journal of Practices and Technologies 13:12-18.
Rajasekharan et al., (2006) "Monoacylglycerol as an intermediate in triacylglycerol biosynthesis in plants" International Symposium on Plant Lipids, Abstract.
Roston at al., (2012) "TGD1, -2, and -3 Proteins Involved in Lipid Trafficking Form ATP-binding Cassette (ABC) Transporter with Multiple Substrate-binding Proteins" The Journal of Biological Chemistry vol. 287, No. 25, pp. 21406-21415.
Sanjaya et al. (2011) "Increasing the energy density of vegetative tissues by diverting carbon from starch to oil biosynthesis in transgenic *Arabidopsis*" Plant Biotech. J. 9:874-883.
Sanjaya et al (2013) "Altered Lipid Composition and Enhanced Nutritional Value of *Arabidopsis* Leaves following Introduction of an Algal Diacylglycerol Acyltransferase 2" Plant Cell, 1-17.
Semwal et al. (2011) "Biodiesel production using heterogeneous catalysts" Bioresource Technology 102:2151-2161.
Sheikh et al (2002) "Fatty Acids Composition in Germinating Cotton Seedlings Affected by High Temperature Stress" Pakistan Journal of Applied Sciences 2:1 p. 97-99.
Shiina et al. (1997) "Identification of Promoter Elements Involved in Cytosolic Ca2+-Mediated Photoregulation of Maize cab-m1 Expression" Plant Physiol. 115:477-483.
Smith et al. (2000) "Total silencing by intron-spliced hairpin RNAs" Nature 407:319-320.
Slocombe et al (2009) "Oil accumulation in leaves directed by modification of fatty acid breakdown and lipid synthesis pathways" Plant Biotechnology Journal, 7, 694-703.
Srinivasan et al, (2007) "Heterologous expression of the Baby Boom AP2/ERF transcription factor enhances the regeneration capacity of tobacco (*Nicotiana tabacum* L.)" Planta 225:341-51.
Takeyama, H., et al., (1997) "Expression of the Eicosapentaenoic Acid Synthesis Gene Cluster From *Shewanella* sp. in a Transgenic Marine Cyanobacterium, *Synechococcus* sp.," Microbiology, 143(Pt 8): 2725-2731.
To et al., (2012) "Wrinkled Transcription Factors Orchestrate Tissue-Specific Regulation of Fatty Acid Biosynthesis in *Arabidopsis*" The Plant Cell, vol. 24: 5007-5023.
Vanhercke et al, (2012) "Maximizing lipid accumulation in vegetative plant tissues" 8th International Symposium on Biocatalysis and Agricultural Biotechnology.
Vanhercke et al. (2013) "Synergistic effect of WRI1 and DGAT1 coexpression on triacylglycerol biosynthesis in plants" FEBS Letters 587:364-369.
Vanhercke et al (2013) "Metabolic engineering of biomass for high energy density: oilseed-like triacylglycerol yields from plant leaves" Plant Biotechnol. J., doi: 10.1111/pbi.12131.
Wood et al. (2009) "A leaf-based assay using interchangeable design principles to rapidly assemble multistep recombinant pathways" Plant Biotech. J. 7: 914-924.
Xu et al., (2008) "Cloning and characterization of an acyl-CoA-dependent diacylglycerol acyltransferase 1 (DGAT1) gene from *Tropaeolum majus*, and a study of the functional motifs of the DGAT protein using site-directed mutagenesis to modify enzyme activity and oil content" Plant Biotechnology Journal 6, pp. 799-818.
Xu et al., (2008) "Lipid Trafficking between the Endoplasmic Reticulum and the Plastid in *Arabidopsis* Requires the Extraplastidic TGD4 Protein" The Plant Cell, vol. 20: 2190-2204.
Xu et al., (2005) "Mutation of the TGD1 Chloroplast Envelope Protein Affects Phosphatidate Metabolism in *Arabidopsis*" The Plant Cell, vol. 17, 3094-3110.
Xu et al., (2010) "Lipid Transport Mediated by *Arabidopsis* TGD Proteins is Unidirectional from the Endoplasmic Reticulum to the Plastid" Plant Cell Physiol, 51(6): 1019-1028.
Yang et al. (2010) "A distinct type of glycerol-3-phosphate acyltransferase with sn-2 preference and phosphatase activity producing 2-monoacylglycerol" PNAS 107:12040-12045.
Yang & Ohlrogge (2009) "Turnover of Fatty Acids during Natural Senescence of *Arabidopsis, Brachypodium*, and Switchgrass and in *Arabidopsis* b-Oxidation Mutants" Plant Physiology, 150, 1981-1989.
GenBank Accession No. BAC45173.1, Sasaki et al. (2002).
GenBank Accession No. BAC45170.1, Sasaki et al. (2002).

* cited by examiner

```
        10                          30                          50
TCTCTCCTTTCTCAATGCTGTGGTGGCGGCGCAACCCCTAACAAAGACGTGGGCTTGATT
S   L   L   S   Q   C   C   G   G   G   A   T   P   N   K   D   V   G   L   I
        70                          90                         110
TCTTCCTTCCGTGGATCCACCATTCAAGGCTTGATGGCTTCTTGCTTGGCTTTTGAGCCT
S   S   F   R   G   S   T   I   Q   G   L   M   A   S   C   L   A   F   E   P
       130                         150                         170
TGTGATGATTATTATTCCTCCAAAAATGGTAGCTTTTTCGGTCAAAATGGAAGCTTTTCA
C   D   D   Y   Y   S   S   K   N   G   S   F   F   G   Q   N   G   S   F   S
       190                         210                         230
TCTTTCTTCGGCTCCAAAAATGTTCCTTTCAATAAAAATCGCAAGCAAAAAAGGCTCAAT
S   F   F   G   S   K   N   V   P   F   N   K   N   R   K   Q   K   R   L   N
       250                         270                         290
CGACGAGCTCATCATTCTGGACAAGCCATGGCTATAGCTGTGCAACCCACAAGAGAGATT
R   R   A   H   H   S   G   Q   A   M   A   I   A   V   Q   P   T   R   E   I
       310                         330                         350
ACAACGAAGAAGAAGCCTCCTACGAAgCAAAGACGAGTGGTTGTGACTGGGATGGGAGTA
T   T   K   K   K   P   P   T   K   Q   R   R   V   V   V   T   G   M   G   V
       370                         390                         410
GTAACTCCGCTTGGACATGAGCCTGATGTTTTCTATAACAACCTGCTTGAGGGTGTTAGT
V   T   P   L   G   H   E   P   D   V   F   Y   N   N   L   L   E   G   V   S
       430                         450                         470
GGTATAAGTGAAATCGAGACTTTTGACTGCGCTCAGTTTCCGACAAGGATTGCTGGAGAG
G   I   S   E   I   E   T   F   D   C   A   Q   F   P   T   R   I   A   G   E
       490                         510                         530
ATCAAATCTTTCTCAACTGATGGATGGGTCGCACCGAAACTTTCCAAGAGGATGGACAAA
I   K   S   F   S   T   D   G   W   V   A   P   K   L   S   K   R   M   D   K
       550                         570                         590
TTCATGCTTTATTCTCTTACTGCCGGAAAGAAAGCTTTGCAAGATGGGGGAGTAAATGAA
F   M   L   Y   S   L   T   A   G   K   K   A   L   Q   D   G   G   V   N   E
       610                         630                         650
GATGTAATGGAGGAGTTAGATAAAACGAAATGCGGAGTTTTGATTGGTTCAGCAATGGGT
D   V   M   E   E   L   D   K   T   K   C   G   V   L   I   G   S   A   M   G
       670                         690                         710
GGCATGAAGGTTTTCAATGATGCGATTGAAGCTTTGAGGATCTCATACAGGAAGATGAAT
G   M   K   V   F   N   D   A   I   E   A   L   R   I   S   Y   R   K   M   N
       730                         750                         770
CCTTTTTGCGTACCGTTTGCTACAACAAATATGGGTTCTGCAATGCTTGCAATGGATTTG
P   F   C   V   P   F   A   T   T   N   M   G   S   A   M   L   A   M   D   L
       790                         810                         830
GGATGGATGGGTCCTAATTATTCAATCTCCACTGCATGTGCTACAAGCAACTTTTGCATA
G   W   M   G   P   N   Y   S   I   S   T   A   C   A   T   S   N   F   C   I
       850                         870                         890
TTAAATGCAGCAAACCATATCATTAGAGGCGAAGCTGATATGATGCTTTGTGGTGGCTCC
L   N   A   A   N   H   I   I   R   G   E   A   D   M   M   L   C   G   G   S
       910                         930                         950
GATGCAGCGATTATACCCATTGGTTTGGGGGGATTTGTGGCTTGTAGAGCGCTTTCTCAG
D   A   A   I   I   P   I   G   L   G   G   F   V   A   C   R   A   L   S   Q
       970                         990                        1010
AGGAACAATGATCCTACCAAAGCTTCACGCCCTTGGGATGCTAATCGCGATGGATTTGTC
R   N   N   D   P   T   K   A   S   R   P   W   D   A   N   R   D   G   F   V
```

Figure 3

```
        1030                      1050                      1070
ATGGGGGAAGGTGCTGGGGTTCTACTTTTGGAAGAATTGGAGCATGCTAAGAGGAGAGGT
M   G   E   G   A   G   V   L   L   L   E   E   L   E   H   A   K   R   R   G
        1090                      1110                      1130
GCGACTATCTATGCAGAATTCCTTGGTGGAAGCTTCACTTGTGATGCTTATCACATGACC
A   T   I   Y   A   E   F   L   G   G   S   F   T   C   D   A   Y   H   M   T
        1150                      1170                      1190
GAGCCTCACCCTGATGGTGTTGGTGTCATTCTCTGCATCGAAAAGGCCTTGGCTCACGCT
E   P   H   P   D   G   V   G   V   I   L   C   I   E   K   A   L   A   H   A
        1210                      1230                      1250
GGTGTATCTAGAGGAGATATAAACTATATTAATGCTCATGCTACATCGACACCAACTGGA
G   V   S   R   G   D   I   N   Y   I   N   A   H   A   T   S   T   P   T   G
        1270                      1290                      1310
GACATTAAAGAATACCAAGCTCTTCTTCATTGTTTTGGAGAAAATCCCGAGTTAAGGGTG
D   I   K   E   Y   Q   A   L   L   H   C   F   G   E   N   P   E   L   R   V
        1330                      1350                      1370
AACTCTACAAAATCAATGATTGGTCACCTACTAGGAGCTTCCGGTGCTGTGGAAGCTGTT
N   S   T   K   S   M   I   G   H   L   L   G   A   S   G   A   V   E   A   V
        1390                      1410                      1430
GCAACGGTACAGGCAATACGAACTGGTTGGGTTCATCCAAATATCAACCTGGAAAACCCG
A   T   V   Q   A   I   R   T   G   W   V   H   P   N   I   N   L   E   N   P
        1450                      1470                      1490
GATGTAGGAGTGGACACAAGTGTGCTTGTGGGGCCAAATAAAGAAAGATTGAACGTtAAG
D   V   G   V   D   T   S   V   L   V   G   P   N   K   E   R   L   N   V   K
        1510                      1530                      1550
GCGGCATTGTCGAATTCATTCGGGTTTGGCGGGCATAACTCATCGATCATTTTCGCCCCA
A   A   L   S   N   S   F   G   F   G   G   H   N   S   S   I   I   F   A   P
        1570                      1590                      1610
TACAAGTAAAAATAGTTCAACAGCTGCTCTCCCAGTGTTTTCTTACATTTGGCCGAAGAG
Y   K   *
        1630                      1650                      1670
TATCCCAGAAAATCCTcCTGTAGACAAAACATAACTCTGAAAGCGTTATTATTACGAAGT
        1690                      1710                      1730
AGTACGGTGGTGGCCGGTAGCAGAGCTCTAGAAAAAAAAAAACCTCCTACTGTTTCATAG
        1750                      1770                      1790
TTCAGTGTTTGTTTGGGAAGGTTTCGTTTCACTTAAACGTAGTAGCTACAATTGAGGTTT
        1810                      1830                      1850
TAGTGTTTGAGGCCACAGGGCCATTGAAGAACCAGTAAATGTAGTAATTTTTGTGCTCAT
        1870                      1890                      1910
GTAAAAGAAATGGCTTATATCAGTTGTTGTTTTTTTTTTTAATTAAAGCCAATTTGTAAT
        1930                      1950                      1970
GAATCCTGAATTGGCAGCAGGGTGGATGATTTTCTCATTTAATCTTCATGCAAAAGCTTG
        1990
TTTTCTACCTTAAAAAA
```

Figure 3 continued

```
        10                  30                  50
TCCAAGGCTCAATCGAGGTGTTGCCCGATCTGGACAAGCCATGGCTGTAGCTGTGGAACC
                                          M  A  V  A  V  E  P
        70                  90                 110
GGCGAGAGAGATCATGACAAAACAGAAACCTCCTACGAAGCAAAGACGTGTTGTAGTGAC
 A  R  E  I  M  T  K  Q  K  P  P  T  K  Q  R  R  V  V  V  T
       130                 150                 170
TGGGATGGGAGTAGTAACTCCACTTGGCCATGACCCCGATGTTTTTATAACAATTTGCT
 G  M  G  V  V  T  P  L  G  H  D  P  D  V  F  Y  N  N  L  L
       190                 210                 230
TGAGGGTGCTAGTGGTATAAGTGAAATTGAGGCTTTTGACTGTGCCCAGTTTCCAACCAG
 E  G  A  S  G  I  S  E  I  E  A  F  D  C  A  Q  F  P  T  R
       250                 270                 290
AATTGCCGGAGAGATCAAATCTTTATCGGCCGATGGATGGATAGCACCAAAACTATCCAA
 I  A  G  E  I  K  S  L  S  A  D  G  W  I  A  P  K  L  S  K
       310                 330                 350
AAGGATGGACAAATTCATGCTTTATATGCTTATTGCCGGAAAAAAAGCATTAGAAGACGG
 R  M  D  K  F  M  L  Y  M  L  I  A  G  K  K  A  L  E  D  G
       370                 390                 410
TGGAGTAACCGAAGATGTAATGGAGGAATTAGATAAAGAGAAATGCGGAGTTTTGATCGG
 G  V  T  E  D  V  M  E  E  L  D  K  E  K  C  G  V  L  I  G
       430                 450                 470
TTCGGCAATGGGTGGTATGAAGGTTTTCAATGATGCAATTGAAGCACTGAGGATTTCGTA
 S  A  M  G  G  M  K  V  F  N  D  A  I  E  A  L  R  I  S  Y
       490                 510                 530
TAGGAAAATGAATCCGTTTTGTGTACCATTTGCTACTACAAATATGGGTTCCGCAATGCT
 R  K  M  N  P  F  C  V  P  F  A  T  T  N  M  G  S  A  M  L
       550                 570                 590
TGCAATGGATTTGGGATGGATGGGTCCTAACTATTCGATCTCTACCGCATGTGCTACGAG
 A  M  D  L  G  W  M  G  P  N  Y  S  I  S  T  A  C  A  T  S
       610                 630                 650
CAACTTTTGTATCTTAAATGCAGCAAATCACATGATTAGAGGCGAAGCTGATATGATGCT
 N  F  C  I  L  N  A  A  N  H  M  I  R  G  E  A  D  M  M  L
       670                 690                 710
CTGTGGTGGCTCTGATGCAGCAATTATACCCATCGGGTTGGGAGGATTTGTTGCATGCAA
 C  G  G  S  D  A  A  I  I  P  I  G  L  G  G  F  V  A  C  K
       730                 750                 770
AGCACTGTCCAAGAGGAACGGTGATCCTACAAAAGCTTCACGTCCATGGGATGTTAATCG
 A  L  S  K  R  N  G  D  P  T  K  A  S  R  P  W  D  V  N  R
       790                 810                 830
TGACGGGTTTGTCATGGGGGAAGGTGCTGGGGTTCTGCTTTTAGAAGAGTTGGAGCATGC
 D  G  F  V  M  G  E  G  A  G  V  L  L  L  E  E  L  E  H  A
       850                 870                 890
TAAGAGGCGAGGAGCGACTATCTATGCAGAATTCCTCGGTGGTAGCTTCACTTGTGATGC
 K  R  R  G  A  T  I  Y  A  E  F  L  G  G  S  F  T  C  D  A
       910                 930                 950
TTATCACATGACGGAACCACACCCAGATGGAGTTGGTGTTGTTCGCTGCATAGAAAAGGC
 Y  H  M  T  E  P  H  P  D  G  V  G  V  V  R  C  I  E  K  A
       970                 990                1010
TTTGGCTCAGTCTGGAGTACCTCGAGAAGATATAAATTACATTAATGCTCATGCTACATC
 L  A  Q  S  G  V  P  R  E  D  I  N  Y  I  N  A  H  A  T  S
```

Figure 4

```
        1030                      1050                      1070
TACACCATCCGGAGACATTAAAGAGTACCAAGCTCTCCTACATTGTTTCGGCAAAAATCC
 T   P   S   G   D   I   K   E   Y   Q   A   L   L   H   C   F   G   K   N   P
        1090                      1110                      1130
CGAGTTAAGAGTGAACTCCACTAAGTCGATGATCGGTCACCTACTCGGAGCTGCCGGTGC
 E   L   R   V   N   S   T   K   S   M   I   G   H   L   L   G   A   A   G   A
        1150                      1170                      1190
TGTGGAAGCCATTGCAGCGGTACAGGCGATAAGAACTGGTTGGGTTCATCCAAATATCAA
 V   E   A   I   A   A   V   Q   A   I   R   T   G   W   V   H   P   N   I   N
        1210                      1230                      1250
CCTTGAAAACCCGGACCAAGAAGTGGACACAAATGTGCTCGTTGGACCAAAGAAAGAAAG
 L   E   N   P   D   Q   E   V   D   T   N   V   L   V   G   P   K   K   E   R
        1270                      1290                      1310
GTTGAATGTCAAGGCAGCTTTGTCCAATTCTTTCGGGTTTGGTGGCCACAACTCCTCGAT
 L   N   V   K   A   A   L   S   N   S   F   G   F   G   G   H   N   S   S   I
        1330                      1350                      1370
CATATTTGCTCCGTACAAGTAAAAAAAAAAAAGAACATAGTCCATGCATCGCTCGTACCGG
 I   F   A   P   Y   K   *
        1390                      1410                      1430
GTTACCGTAGCTGCTGTTGTACGTAAATTCTATCGGCTATTTGGTCAGGAAAAGTGTTAA
        1450                      1470                      1490
TATAGGTCAGCTACATCGTGCAGAAGACTCGAGAAACCTCGTCTATCGACAAACACCGGT
        1510                      1530                      1550
CCGGAAAAAGGGTTATCATAGGGAGAAAGATGATGTTTAAGAGTTCATTGTTGTGTTTTA
        1570                      1590                      1610
AAGATGTCATATTTTCTATTAAATTTTAAAGCTACGATGGGAAAAAAAAAAAAAAAAAAA

AAAAAAAA
```

Figure 4 continued

```
   1  CGTATTGCCT GTACCGTTGC AACAGCTTCC ACAGCACCGG AAGCTCCTAG
  51  TAGGTGACCA ATCATTGATT TTGTAGAGTT CACCCTTAAC TCGGGATTTT
 101  CTCCAAAACA ATGAAGAAGA GCTTGGTATT CTTTAATGTC TCCAGTTGGT
 151  GTCGATGTAG CATGAGCATT AATATAGTTT ATATCTCCTC TAGATACACC
 201  AGCGTGAGCC AAGGCCTTTT CGATGCAGAG AATGACACCA ACACCATCAG
 251  GGTGAGGCTC GGTCATGTGA TAAGCATCAC AAGTGAAGCT TCCACCAAGG
 301  AATTCTGCAT AGATAGTCGC ACCTCTCCTC TTAGCATGCT CCAATTCTTC
 351  CAAAAGTAGA ACCCCAGCAC CTTCCCCCAT GACAAATCCA TCGCGATTAG
 401  CCATGGCTAT AGCTGTGCAA CCCACAAGAG AGATTACAAC GAAGAAGAAG
      NcoI
 451  CCTCCTACGA AGCAAAGACG AGTGGTTGTG ACTGGGATGG GAGTAGTAAC
 501  TCCGCTTGGA CATGAGCCTG ATGTTTTCTA TAACAACCTG CTTGAGGGTG
 551  TTAGTGGTAT AAGTGAAATC GAGACTTTTG ACTGCGCTCA GTTTCCGACA
 601  AGGATTGCTG GAGAGATCAA ATCTTTCTCA ACTGATGGAT GGGTCGCACC
 651  GAAACTTTCC AAGAGGATGG ACAAATTCAT GCTTTATTCT CTTACTGCCG
 701  GAAAGAAAGC TTTGCAAGAT GGGGGAGTAA ATGAAGATGT AATGGAGGAG
 751  TTAGATAAAA CGAAATGCGG AGTTTTGATT GGTTCAGCAA TGGGTGGCAT
 801  GAAGGTTTTC AATGATGCGA TTGAAGCTTT GAGGATCTCA TACAGGAAGA
 851  TGAATCCTTT TTGCGTACCG TTTGCTACAA CAAATATGGG TTCTGCAATG
 901  CTTGCAATGG ATTTGGGATG GATGGGTCCT AATTATTCAA TCTCCACTGC
 951  ATGTGCTACA AGCAACTTTT GCATATTAAA TGCAGCAAAC CATATCATTA
1001  GAGGCGAAGC TGATATGATG CTTTGTGGTG GCTCCGATGC AGCGATTATA
1051  CCCATTGGTT TGGGGGGATT TGTGGCTTGT AGAGCGCTTT CTCAGAGGAA
1101  CAATGATCCT ACCAAAGCTT CACGCCCTTG GGATGCTAAT CGCGATGGAT
1151  TTGTCATGGG GGAAGGTGCT GGGGTTCTAC TTTTGGAAGA ATTGGAGCAT
1201  GCTAAGAGGA GAGGTGCGAC TATCTATGCA GAATTCCTTG GTGGAAGCTT
1251  CACTTGTGAT GCTTATCACA TGACCGAGCC TCACCCTGAT GGTGTTGGTG
1301  TCATTCTCTG CATCGAAAAG GCCTTGGCTC ACGCTGGTGT ATCTAGAGGA
1351  GATATAAACT ATATTAATGC TCATGCTACA TCGACACCAA CTGGAGACAT
1401  TAAAGAATAC CAAGCTCTTC TTCATTGTTT TGGAGAAAAT CCCGAGTTAA
1451  GGGTGAACTC TACAAAATCA ATGATTGGTC ACCTACTAGG AGCTTCCGGT
1501  GCTGTGGAAG CTGTTGCAAC GGTACAGGCA ATACG
```

Figure 6

SEQUENCE LISTING

```
<160> NUMBER OF SEQ ID NOS: 23

<210> SEQ ID NO 1
<211> LENGTH: 1997
<212> TYPE: DNA
<213> ORGANISM: Gossypium hirsutum

<400> SEQUENCE: 1

tctctccttt ctcaatgctg tggtggcggc gcaaccccta acaaagacgt gggcttgatt      60

tcttccttcc gtggatccac cattcaaggc ttgatggctt cttgcttggc ttttgagcct     120

tgtgatgatt attattcctc caaaaatggt agctttttcg gtcaaaatgg aagcttttca     180

tctttcttcg gctccaaaaa tgttcctttc aataaaaatc gcaagcaaaa aaggctcaat     240

cgacgagctc atcattctgg acaagccatg gctatagctg tgcaacccac aagagagatt     300

acaacgaaga agaagcctcc tacgaagcaa agacgagtgg ttgtgactgg gatgggagta     360

gtaactccgc ttggacatga gcctgatgtt ttctataaca acctgcttga gggtgttagt     420

ggtataagtg aaatcgagac ttttgactgc gctcagtttc cgacaaggat tgctggagag     480

atcaaatctt tctcaactga tggatgggtc gcaccgaaac tttccaagag gatggacaaa     540

ttcatgcttt attctcttac tgccggaaag aaagctttgc aagatggggg agtaaatgaa     600

gatgtaatgg aggagttaga taaaacgaaa tgcggagttt tgattggttc agcaatgggt     660

ggcatgaagg ttttcaatga tgcgattgaa gctttgagga tctcatacag gaagatgaat     720

ccttttttgcg taccgtttgc tacaacaaat atgggttctg caatgcttgc aatggatttg     780

ggatggatgg gtcctaatta ttcaatctcc actgcatgtg ctacaagcaa cttttgcata     840

ttaaatgcag caaaccatat cattagaggc gaagctgata tgatgctttg tggtggctcc     900

gatgcagcga ttatacccat tggtttgggg ggatttgtgg cttgtagagc gctttctcag     960
```

```
aggaacaatg atcctaccaa agcttcacgc ccttgggatg ctaatcgcga tggatttgtc   1020

atgggggaag gtgctggggt tctacttttg gaagaattgg agcatgctaa gaggagaggt   1080

gcgactatct atgcagaatt ccttggtgga agcttcactt gtgatgctta tcacatgacc   1140

gagcctcacc ctgatggtgt tggtgtcatt ctctgcatcg aaaaggcctt ggctcacgct   1200

ggtgtatcta gaggagatat aaactatatt aatgctcatg ctacatcgac accaactgga   1260

gacattaaag aataccaagc tcttcttcat tgttttggag aaaatcccga gttaagggtg   1320

aactctacaa aatcaatgat tggtcaccta ctaggagctt ccggtgctgt ggaagctgtt   1380

gcaacggtac aggcaatacg aactggttgg gttcatccaa atatcaacct ggaaaacccg   1440

gatgtaggag tggacacaag tgtgcttgtg gggccaaata aagaaagatt gaacgttaag   1500

gcggcattgt cgaattcatt cgggtttggc gggcataact catcgatcat tttcgcccca   1560

tacaagtaaa aatagttcaa cagctgctct cccagtgttt tcttacattt ggccgaagag   1620

tatcccagaa aatcctcctg tagacaaaac ataactctga aagcgttatt attacgaagt   1680

agtacggtgg tggccggtag cagagctcta gaaaaaaaaa aacctcctac tgtttcatag   1740

ttcagtgttt gtttgggaag gtttcgtttc acttaaacgt agtagctaca attgaggttt   1800

tagtgtttga ggccacaggg ccattgaaga accagtaaat gtagtaattt ttgtgctcat   1860

gtaaaagaaa tggcttatat cagttgttgt ttttttttt aattaaagcc aatttgtaat    1920

gaatcctgaa ttggcagcag ggtggatgat tttctcattt aatcttcatg caaaagcttg   1980

ttttctacct taaaaaa                                                  1997


<210> SEQ ID NO 2
<211> LENGTH: 522
<212> TYPE: PRT
<213> ORGANISM: Gossypium hirsutum

<400> SEQUENCE: 2

Ser Leu Leu Ser Gln Cys Cys Gly Gly Gly Ala Thr Pro Asn Lys Asp
1               5                   10                  15

Val Gly Leu Ile Ser Ser Phe Arg Gly Ser Thr Ile Gln Gly Leu Met
            20                  25                  30

Ala Ser Cys Leu Ala Phe Glu Pro Cys Asp Asp Tyr Tyr Ser Ser Lys
        35                  40                  45

Asn Gly Ser Phe Phe Gly Gln Asn Gly Ser Phe Ser Ser Phe Phe Gly
    50                  55                  60

Ser Lys Asn Val Pro Phe Asn Lys Asn Arg Lys Gln Lys Arg Leu Asn
65                  70                  75                  80

Arg Arg Ala His His Ser Gly Gln Ala Met Ala Ile Ala Val Gln Pro
                85                  90                  95

Thr Arg Glu Ile Thr Thr Lys Lys Lys Pro Pro Thr Lys Gln Arg Arg
            100                 105                 110

Val Val Val Thr Gly Met Gly Val Val Thr Pro Leu Gly His Glu Pro
        115                 120                 125

Asp Val Phe Tyr Asn Asn Leu Leu Glu Gly Val Ser Gly Ile Ser Glu
    130                 135                 140

Ile Glu Thr Phe Asp Cys Ala Gln Phe Pro Thr Arg Ile Ala Gly Glu
145                 150                 155                 160

Ile Lys Ser Phe Ser Thr Asp Gly Trp Val Ala Pro Lys Leu Ser Lys
                165                 170                 175

Arg Met Asp Lys Phe Met Leu Tyr Ser Leu Thr Ala Gly Lys Lys Ala
```

```
                180             185             190
Leu Gln Asp Gly Gly Val Asn Glu Asp Val Met Glu Glu Leu Asp Lys
            195                 200                 205

Thr Lys Cys Gly Val Leu Ile Gly Ser Ala Met Gly Gly Met Lys Val
210                 215                 220

Phe Asn Asp Ala Ile Glu Ala Leu Arg Ile Ser Tyr Arg Lys Met Asn
225                 230                 235                 240

Pro Phe Cys Val Pro Phe Ala Thr Thr Asn Met Gly Ser Ala Met Leu
                245                 250                 255

Ala Met Asp Leu Gly Trp Met Gly Pro Asn Tyr Ser Ile Ser Thr Ala
            260                 265                 270

Cys Ala Thr Ser Asn Phe Cys Ile Leu Asn Ala Ala Asn His Ile Ile
        275                 280                 285

Arg Gly Glu Ala Asp Met Met Leu Cys Gly Gly Ser Asp Ala Ala Ile
    290                 295                 300

Ile Pro Ile Gly Leu Gly Gly Phe Val Ala Cys Arg Ala Leu Ser Gln
305                 310                 315                 320

Arg Asn Asn Asp Pro Thr Lys Ala Ser Arg Pro Trp Asp Ala Asn Arg
                325                 330                 335

Asp Gly Phe Val Met Gly Glu Gly Ala Gly Val Leu Leu Leu Glu Glu
            340                 345                 350

Leu Glu His Ala Lys Arg Arg Gly Ala Thr Ile Tyr Ala Glu Phe Leu
        355                 360                 365

Gly Gly Ser Phe Thr Cys Asp Ala Tyr His Met Thr Glu Pro His Pro
    370                 375                 380

Asp Gly Val Gly Val Ile Leu Cys Ile Glu Lys Ala Leu Ala His Ala
385                 390                 395                 400

Gly Val Ser Arg Gly Asp Ile Asn Tyr Ile Asn Ala His Ala Thr Ser
                405                 410                 415

Thr Pro Thr Gly Asp Ile Lys Glu Tyr Gln Ala Leu Leu His Cys Phe
            420                 425                 430

Gly Glu Asn Pro Glu Leu Arg Val Asn Ser Thr Lys Ser Met Ile Gly
        435                 440                 445

His Leu Leu Gly Ala Ser Gly Ala Val Glu Ala Val Ala Thr Val Gln
    450                 455                 460

Ala Ile Arg Thr Gly Trp Val His Pro Asn Ile Asn Leu Glu Asn Pro
465                 470                 475                 480

Asp Val Gly Val Asp Thr Ser Val Leu Val Gly Pro Asn Lys Glu Arg
                485                 490                 495

Leu Asn Val Lys Ala Ala Leu Ser Asn Ser Phe Gly Phe Gly Gly His
            500                 505                 510

Asn Ser Ser Ile Ile Phe Ala Pro Tyr Lys
        515                 520

<210> SEQ ID NO 3
<211> LENGTH: 1628
<212> TYPE: DNA
<213> ORGANISM: Gossypium hirsutum

<400> SEQUENCE: 3

tccaaggctc aatcgaggtg ttgcccgatc tggacaagcc atggctgtag ctgtggaacc      60

ggcgagagag atcatgacaa aacagaaacc tcctacgaag caaagacgtg ttgtagtgac     120

tgggatggga gtagtaactc cacttggcca tgaccccgat gttttttata acaatttgct     180
```

-continued

```
tgagggtgct agtggtataa gtgaaattga ggcttttgac tgtgcccagt ttccaaccag    240

aattgccgga gagatcaaat ctttatcggc cgatggatgg atagcaccaa aactatccaa    300

aaggatggac aaattcatgc tttatatgct tattgccgga aaaaaagcat tagaagacgg    360

tggagtaacc gaagatgtaa tggaggaatt agataaagag aaatgcggag ttttgatcgg    420

ttcggcaatg ggtggtatga aggttttcaa tgatgcaatt gaagcactga ggatttcgta    480

taggaaaatg aatccgtttt gtgtaccatt tgctactaca aatatgggtt ccgcaatgct    540

tgcaatggat ttgggatgga tgggtcctaa ctattcgatc tctaccgcat gtgctacgag    600

caacttttgt atcttaaatg cagcaaatca catgattaga ggcgaagctg atatgatgct    660

ctgtggtggc tctgatgcag caattatacc catcgggttg ggaggatttg ttgcatgcaa    720

agcactgtcc aagaggaacg gtgatcctac aaaagcttca cgtccatggg atgttaatcg    780

tgacgggttt gtcatggggg aaggtgctgg ggttctgctt ttagaagagt tggagcatgc    840

taagaggcga ggagcgacta tctatgcaga attcctcggt ggtagcttca cttgtgatgc    900

ttatcacatg acggaaccac acccagatgg agttggtgtt gttcgctgca tagaaaaggc    960

tttggctcag tctggagtac ctcgagaaga tataaattac attaatgctc atgctacatc   1020

tacaccatcc ggagacatta aagagtacca agctctccta cattgtttcg gcaaaaatcc   1080

cgagttaaga gtgaactcca ctaagtcgat gatcggtcac ctactcggag ctgccggtgc   1140

tgtggaagcc attgcagcgg tacaggcgat aagaactggt tgggttcatc caaatatcaa   1200

ccttgaaaac ccggaccaag aagtggacac aaatgtgctc gttggaccaa agaaagaaag   1260

gttgaatgtc aaggcagctt tgtccaattc tttcgggttt ggtggccaca actcctcgat   1320

catatttgct ccgtacaagt aaaaaaaaaa agaacatagt ccatgcatcg ctcgtaccgg   1380

gttaccgtag ctgctgttgt acgtaaattc tatcggctat ttggtcagga aaagtgttaa   1440

tataggtcag ctacatcgtg cagaagactc gagaaacctc gtctatcgac aaacaccggt   1500

ccggaaaaag ggttatcata gggagaaaga tgatgtttaa gagttcattg ttgtgtttta   1560

aagatgtcat attttctatt aaattttaaa gctacgatgg gaaaaaaaaa aaaaaaaaaa   1620

aaaaaaaa                                                            1628


<210> SEQ ID NO 4
<211> LENGTH: 433
<212> TYPE: PRT
<213> ORGANISM: Gossypium hirsutum

<400> SEQUENCE: 4

Met Ala Val Ala Val Glu Pro Ala Arg Glu Ile Met Thr Lys Gln Lys
1               5                   10                  15

Pro Pro Thr Lys Gln Arg Arg Val Val Val Thr Gly Met Gly Val Val
            20                  25                  30

Thr Pro Leu Gly His Asp Pro Asp Val Phe Tyr Asn Asn Leu Leu Glu
        35                  40                  45

Gly Ala Ser Gly Ile Ser Glu Ile Glu Ala Phe Asp Cys Ala Gln Phe
    50                  55                  60

Pro Thr Arg Ile Ala Gly Glu Ile Lys Ser Leu Ser Ala Asp Gly Trp
65                  70                  75                  80

Ile Ala Pro Lys Leu Ser Lys Arg Met Asp Lys Phe Met Leu Tyr Met
                85                  90                  95

Leu Ile Ala Gly Lys Lys Ala Leu Glu Asp Gly Gly Val Thr Glu Asp
            100                 105                 110
```

Val Met Glu Glu Leu Asp Lys Glu Lys Cys Gly Val Leu Ile Gly Ser
        115                 120                 125

Ala Met Gly Gly Met Lys Val Phe Asn Asp Ala Ile Glu Ala Leu Arg
130                 135                 140

Ile Ser Tyr Arg Lys Met Asn Pro Phe Cys Val Pro Phe Ala Thr Thr
145                 150                 155                 160

Asn Met Gly Ser Ala Met Leu Ala Met Asp Leu Gly Trp Met Gly Pro
                165                 170                 175

Asn Tyr Ser Ile Ser Thr Ala Cys Ala Thr Ser Asn Phe Cys Ile Leu
                180                 185                 190

Asn Ala Ala Asn His Met Ile Arg Gly Glu Ala Asp Met Met Leu Cys
            195                 200                 205

Gly Gly Ser Asp Ala Ala Ile Ile Pro Ile Gly Leu Gly Gly Phe Val
210                 215                 220

Ala Cys Lys Ala Leu Ser Lys Arg Asn Gly Asp Pro Thr Lys Ala Ser
225                 230                 235                 240

Arg Pro Trp Asp Val Asn Arg Asp Gly Phe Val Met Gly Glu Gly Ala
                245                 250                 255

Gly Val Leu Leu Leu Glu Glu Leu Glu His Ala Lys Arg Arg Gly Ala
                260                 265                 270

Thr Ile Tyr Ala Glu Phe Leu Gly Gly Ser Phe Thr Cys Asp Ala Tyr
            275                 280                 285

His Met Thr Glu Pro His Pro Asp Gly Val Gly Val Val Arg Cys Ile
        290                 295                 300

Glu Lys Ala Leu Ala Gln Ser Gly Val Pro Arg Glu Asp Ile Asn Tyr
305                 310                 315                 320

Ile Asn Ala His Ala Thr Ser Thr Pro Ser Gly Asp Ile Lys Glu Tyr
                325                 330                 335

Gln Ala Leu Leu His Cys Phe Gly Lys Asn Pro Glu Leu Arg Val Asn
                340                 345                 350

Ser Thr Lys Ser Met Ile Gly His Leu Leu Gly Ala Ala Gly Ala Val
            355                 360                 365

Glu Ala Ile Ala Ala Val Gln Ala Ile Arg Thr Gly Trp Val His Pro
370                 375                 380

Asn Ile Asn Leu Glu Asn Pro Asp Gln Glu Val Asp Thr Asn Val Leu
385                 390                 395                 400

Val Gly Pro Lys Lys Glu Arg Leu Asn Val Lys Ala Ala Leu Ser Asn
                405                 410                 415

Ser Phe Gly Phe Gly Gly His Asn Ser Ser Ile Ile Phe Ala Pro Tyr
                420                 425                 430

Lys

<210> SEQ ID NO 5
<211> LENGTH: 1535
<212> TYPE: DNA
<213> ORGANISM: Gossypium hirsutum

<400> SEQUENCE: 5
cgtattgcct gtaccgttgc aacagcttcc acagcaccgg aagctcctag taggtgacca     60
atcattgatt ttgtagagtt cacccttaac tcgggatttt ctccaaaaca atgaagaaga    120
gcttggtatt ctttaatgtc tccagttggt gtcgatgtag catgagcatt aatatagttt    180
atatctcctc tagatacacc agcgtgagcc aaggcctttt cgatgcagag aatgacacca    240
acaccatcag ggtgaggctc ggtcatgtga taagcatcac aagtgaagct tccaccaagg    300

```
aattctgcat agatagtcgc acctctcctc ttagcatgct ccaattcttc caaaagtaga    360
accccagcac cttcccccat gacaaatcca tcgcgattag ccatggctat agctgtgcaa    420
cccacaagag agattacaac gaagaagaag cctcctacga agcaaagacg agtggttgtg    480
actgggatgg gagtagtaac tccgcttgga catgagcctg atgttttcta taacaacctg    540
cttgagggtg ttagtggtat aagtgaaatc gagacttttg actgcgctca gtttccgaca    600
aggattgctg gagagatcaa atctttctca actgatggat gggtcgcacc gaaactttcc    660
aagaggatgg acaaattcat gctttattct cttactgccg gaaagaaagc tttgcaagat    720
gggggagtaa atgaagatgt aatggaggag ttagataaaa cgaaatgcgg agttttgatt    780
ggttcagcaa tgggtggcat gaaggttttc aatgatgcga ttgaagcttt gaggatctca    840
tacaggaaga tgaatccttt ttgcgtaccg tttgctacaa caaatatggg ttctgcaatg    900
cttgcaatgg atttgggatg gatgggtcct aattattcaa tctccactgc atgtgctaca    960
agcaactttt gcatattaaa tgcagcaaac catatcatta gaggcgaagc tgatatgatg   1020
ctttgtggtg gctccgatgc agcgattata cccattggtt tgggggggatt tgtggcttgt   1080
agagcgcttt ctcagaggaa caatgatcct accaaagctt cacgcccttg ggatgctaat   1140
cgcgatggat ttgtcatggg ggaaggtgct ggggttctac ttttggaaga attggagcat   1200
gctaagagga gaggtgcgac tatctatgca gaattccttg gtggaagctt cacttgtgat   1260
gcttatcaca tgaccgagcc tcaccctgat ggtgttggtg tcattctctg catcgaaaag   1320
gccttggctc acgctggtgt atctagagga gatataaact atattaatgc tcatgctaca   1380
tcgacaccaa ctggagacat taaagaatac caagctcttc ttcattgttt tggagaaaat   1440
cccgagttaa gggtgaactc tacaaaatca atgattggtc acctactagg agcttccggt   1500
gctgtggaag ctgttgcaac ggtacaggca atacg                              1535
```

<210> SEQ ID NO 6
<211> LENGTH: 1362
<212> TYPE: DNA
<213> ORGANISM: Gossypium hirsutum

<400> SEQUENCE: 6

```
caaaaccaac acgccttctt tgcctcgtgt ttcatcacct ggcgttaaac tgctttcttt     60
aaaaccaaca aaatgggtgc cgggtgggta ggatgccaat tgacgggtat aaaggaggaa    120
aatcgaggct cggtcaatcg agttccgatc gagaagcctc cgtttacgct cggtcagatc    180
aagcaagcca ttccgcccca ctgttttcgc cgctccctcc ttcgatcctt ctcctacgtg    240
gtccatgacc tatgcttagc ctctctcttt tactacattg caacatcata ttttcacttt    300
ctcccacaac ccttttccta cattgcttgg cctgtctatt gggttctcca aggttgcatc    360
ctcaccggtg tttgggtcat cgcacacgaa tgcggtcacc acgctttcag tgactaccaa    420
tgggttgacg acaccgtcgg gttgatcctt cactccgccc ttttagtccc gtacttctcg    480
tggaaaatca gtcaccgccg tcaccactcg aacaccggtt ccatggagcg tgacgaagta    540
ttcgtgccca aacccaagtc taaattatca tgctttgcga aatacttcaa caatccaccc    600
ggtcgagttc tctctcttgt agtcacattg actcttggtt ggcctatgta cttagccttc    660
aacgtttcgg gtcgatacta tgatcgatta gcttcccact ataaccctta cggccccatt    720
tactccgaac gcgagaggct acaagtttac atctccgatg ctggtatagt tgcggtaatt    780
tatgtacttt ataagattgc tgcaacaaaa gggctggctt ggcttttatg cacttatggg    840
```

-continued

```
gtacctctac ttattgtgaa tgccttcctt gtgttgatca cctacttgca acatactcac    900

tcggcattgc cgcattacga ctcgtctgaa tgggattggt ttcgaggagc attgtcgacg    960

attgatcgag attacggggt gttgaacaaa gtgttccata acatcaccga tacgcatgtg   1020

gctcatcacc tcttctcaac gatgccacat tatcatgcaa tggaggccac taaagcaatc   1080

aaaccgatac tcggcaagta ttatcctttc gacgggacac cgatttataa ggcaatgtgg   1140

agggaggcaa aagagtgcct ttacgtcgag gctgacgttg gtggtggtgg tagcaaaggt   1200

gtttttggt atcgtaacaa gttctaaaga cagaccaact gcctgatagc tggccggcaa   1260

aatcgacgta aaacgtactt attagactag tgttaactag ggaagttaat aatggtagga   1320

aaatgtggaa tagctgccta gtagttttat gtattaagtg tt                      1362


<210> SEQ ID NO 7
<211> LENGTH: 384
<212> TYPE: PRT
<213> ORGANISM: Gossypium hirsutum

<400> SEQUENCE: 7

Met Gly Ala Gly Trp Val Gly Cys Gln Leu Thr Gly Ile Lys Glu Glu
1               5                   10                  15

Asn Arg Gly Ser Val Asn Arg Val Pro Ile Glu Lys Pro Pro Phe Thr
            20                  25                  30

Leu Gly Gln Ile Lys Gln Ala Ile Pro Pro His Cys Phe Arg Arg Ser
        35                  40                  45

Leu Leu Arg Ser Phe Ser Tyr Val Val His Asp Leu Cys Leu Ala Ser
    50                  55                  60

Leu Phe Tyr Tyr Ile Ala Thr Ser Tyr Phe His Phe Leu Pro Gln Pro
65                  70                  75                  80

Phe Ser Tyr Ile Ala Trp Pro Val Tyr Trp Val Leu Gln Gly Cys Ile
                85                  90                  95

Leu Thr Gly Val Trp Val Ile Ala His Glu Cys Gly His His Ala Phe
            100                 105                 110

Ser Asp Tyr Gln Trp Val Asp Asp Thr Val Gly Leu Ile Leu His Ser
        115                 120                 125

Ala Leu Leu Val Pro Tyr Phe Ser Trp Lys Ile Ser His Arg Arg His
    130                 135                 140

His Ser Asn Thr Gly Ser Met Glu Arg Asp Glu Val Phe Val Pro Lys
145                 150                 155                 160

Pro Lys Ser Lys Leu Ser Cys Phe Ala Lys Tyr Phe Asn Asn Pro Pro
                165                 170                 175

Gly Arg Val Leu Ser Leu Val Val Thr Leu Thr Leu Gly Trp Pro Met
            180                 185                 190

Tyr Leu Ala Phe Asn Val Ser Gly Arg Tyr Tyr Asp Arg Leu Ala Ser
        195                 200                 205

His Tyr Asn Pro Tyr Gly Pro Ile Tyr Ser Glu Arg Glu Arg Leu Gln
    210                 215                 220

Val Tyr Ile Ser Asp Ala Gly Ile Val Ala Val Ile Tyr Val Leu Tyr
225                 230                 235                 240

Lys Ile Ala Ala Thr Lys Gly Leu Ala Trp Leu Leu Cys Thr Tyr Gly
                245                 250                 255

Val Pro Leu Leu Ile Val Asn Ala Phe Leu Val Leu Ile Thr Tyr Leu
            260                 265                 270

Gln His Thr His Ser Ala Leu Pro His Tyr Asp Ser Ser Glu Trp Asp
        275                 280                 285
```

Trp Phe Arg Gly Ala Leu Ser Thr Ile Asp Arg Asp Tyr Gly Val Leu
    290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Lys Tyr Tyr Pro Phe Asp Gly Thr Pro Ile Tyr
            340                 345                 350

Lys Ala Met Trp Arg Glu Ala Lys Glu Cys Leu Tyr Val Glu Ala Asp
        355                 360                 365

Val Gly Gly Gly Gly Ser Lys Gly Val Phe Trp Tyr Arg Asn Lys Phe
    370                 375                 380

<210> SEQ ID NO 8
<211> LENGTH: 1386
<212> TYPE: DNA
<213> ORGANISM: Gossypium hirsutum

<400> SEQUENCE: 8
tgcttcgtgt ttcatcaacc tggcgttaaa ctgctttctt taaagccagc aaaatgggtg 60
ccggtggtag gatgccaatt gacggtataa aggaggaaaa tcgaggctcg gtcaatcgag 120
ttccgatcga gaagcctccg tttacgctcg gtcagatcaa gcaagccatt ccgcccccact 180 gttttcgccg ctccctcctt cgatccttct cctacgtggt ccatgaccta tgcttagcct 240
ctttctttta ctacattgca acatcatatt ttcactttct cccacaaccc ttttcctaca 300
ttgcttggcc tgtctattgg gttctccaag gttgcatcct caccggtgtt tgggtcatcg 360
cacacgagtg gggtcaccac gctttcagag actaccaatg ggttgacgac accgtcgggt 420
tgatccttca ttccgccctt ttagtcccgt acttctcgtg gaaaatcagt caccgccgtc 480
accactcgaa caccggttcc atggagcgtg acgaagtatt cgtgcccaaa cccaagtcta 540
aattatcatg ctttgcgaaa tacttaaaca atccacccgg tcgagttcta tctcttgtag 600
tcacattgac tcttggttgg cctatgtact tagccttcaa cgtttcgggt cgatactatg 660
atcgattagc ttcccactat aacccttatg gccccattta ctccgatcgc gagaggctac 720
aagtttacat ctccgatact ggtatatttg cggtaattta tgtactttat aagattgctg 780
caacaaaagg gctggcttgg cttttatgca cttatggggt gcctctactt attgtgaatg 840
ccttccttgt gttgatcacc tacttgcaac atactcactc ggcattgccg cattatgact 900
cgtccgaatg ggattggttg cgaggagcat tgtcgacgat ggatcgagat ttcggggtgt 960
tgaacaaagt gttccataac atcaccgata cgcatgttgc tcatcacctc ttctcaacga 1020
tgccacatta tcatgcaatg gaggccacta aagcaatcaa accaatactc ggcaagtatt 1080
atcctttcga cgggacaccg atttacaagg caatgtggag ggaggcaaaa gagtgccttt 1140
acgttgagcc tgacgttggt ggtggtggtg gtggtagcaa aggtgttttt tggtatcgta 1200
acaagttcta aagaccgacc aactgcctga tagctggccg gcgaaatcaa cgtaaaacgt 1260
acttattaga ctagtgttaa ctagggaagt taataattaa tggtaggaaa atgtggaata 1320
gttgcctagt agttttatgt attaagtgtt gtattaataa actatatggt agaaaaaaaa 1380
aaaaaa 1386

<210> SEQ ID NO 9
<211> LENGTH: 385
<212> TYPE: PRT

<213> ORGANISM: Gossypium hirsutum

<400> SEQUENCE: 9

```
Met Gly Ala Gly Gly Arg Met Pro Ile Asp Gly Ile Lys Glu Glu Asn
1               5                   10                  15

Arg Gly Ser Val Asn Arg Val Pro Ile Glu Lys Pro Pro Phe Thr Leu
            20                  25                  30

Gly Gln Ile Lys Gln Ala Ile Pro Pro His Cys Phe Arg Arg Ser Leu
        35                  40                  45

Leu Arg Ser Phe Ser Tyr Val Val His Asp Leu Cys Leu Ala Ser Phe
    50                  55                  60

Phe Tyr Tyr Ile Ala Thr Ser Tyr Phe His Phe Leu Pro Gln Pro Phe
65                  70                  75                  80

Ser Tyr Ile Ala Trp Pro Val Tyr Trp Val Leu Gln Gly Cys Ile Leu
                85                  90                  95

Thr Gly Val Trp Val Ile Ala His Glu Trp Gly His His Ala Phe Arg
            100                 105                 110

Asp Tyr Gln Trp Val Asp Asp Thr Val Gly Leu Ile Leu His Ser Ala
        115                 120                 125

Leu Leu Val Pro Tyr Phe Ser Trp Lys Ile Ser His Arg Arg His His
    130                 135                 140

Ser Asn Thr Gly Ser Met Glu Arg Asp Glu Val Phe Val Pro Lys Pro
145                 150                 155                 160

Lys Ser Lys Leu Ser Cys Phe Ala Lys Tyr Leu Asn Asn Pro Pro Gly
                165                 170                 175

Arg Val Leu Ser Leu Val Val Thr Leu Thr Leu Gly Trp Pro Met Tyr
            180                 185                 190

Leu Ala Phe Asn Val Ser Gly Arg Tyr Tyr Asp Arg Leu Ala Ser His
        195                 200                 205

Tyr Asn Pro Tyr Gly Pro Ile Tyr Ser Asp Arg Glu Arg Leu Gln Val
    210                 215                 220

Tyr Ile Ser Asp Thr Gly Ile Phe Ala Val Ile Tyr Val Leu Tyr Lys
225                 230                 235                 240

Ile Ala Ala Thr Lys Gly Leu Ala Trp Leu Leu Cys Thr Tyr Gly Val
                245                 250                 255

Pro Leu Leu Ile Val Asn Ala Phe Leu Val Leu Ile Thr Tyr Leu Gln
            260                 265                 270

His Thr His Ser Ala Leu Pro His Tyr Asp Ser Ser Glu Trp Asp Trp
        275                 280                 285

Leu Arg Gly Ala Leu Ser Thr Met Asp Arg Asp Phe Gly Val Leu Asn
    290                 295                 300

Lys Val Phe His Asn Ile Thr Asp Thr His Val Ala His His Leu Phe
305                 310                 315                 320

Ser Thr Met Pro His Tyr His Ala Met Glu Ala Thr Lys Ala Ile Lys
                325                 330                 335

Pro Ile Leu Gly Lys Tyr Tyr Pro Phe Asp Gly Thr Pro Ile Tyr Lys
            340                 345                 350

Ala Met Trp Arg Glu Ala Lys Glu Cys Leu Tyr Val Glu Pro Asp Val
        355                 360                 365

Gly Gly Gly Gly Gly Gly Ser Lys Gly Val Phe Trp Tyr Arg Asn Lys
    370                 375                 380

Phe
385
```

<210> SEQ ID NO 10
<211> LENGTH: 743
<212> TYPE: DNA
<213> ORGANISM: Gossypium hirsutum
<220> FEATURE:
<221> NAME/KEY: misc_feature
<222> LOCATION: (571)..(571)
<223> OTHER INFORMATION: n is a, c, g, or t

<400> SEQUENCE: 10

```
atggtttacc cacgcgtccg gtagaacatg ttggtgaaga atatattgag gagttttaca     60

gatgctgtga ccaattactg aaagaagatg gactttttgt tcttcagttc atatctatcc    120

cagaagagct ttccaaagaa atccagcaaa cagcaggttt tctaaaggaa tatatattcc    180

ccggtggaac cctgctttct ttggatagga atttatcagc catggctgct gcaacaagat    240

tcagtgtgga gcatgtggaa aatataggaa tgagttatta ccacacactg agatggtgga    300

gaaaactttt cctggaaaac acaagcaaag ttctagctct gggattcgac gagaagttca    360

tgaggacatg ggaatactat ttcgattact gcgctgccgg ttttaagaca ggaaccctta    420

tagattacca ggttgtattt tcgcgggccg gaaatttcgg tacactcgga gatccataca    480

aaggtttccc ttctgcatac tccttcatgg atgattgaac aaagtgtggt tgaacattga    540

tccaaagaag caaacaaaat tatcaccaca ntgccagtgt taagaacaac ctatctccct    600

agtccctact tttctttatt atggctatgt ttgcaatgca agaataagca aacattgtaa    660

tgtcaataaa gtttgcactt ttgtagactg gatgggatgt tatcaatgaa gtacctagtt    720

tataagtaaa aaaaaaaaaa aga                                            743
```

<210> SEQ ID NO 11
<211> LENGTH: 2884
<212> TYPE: DNA
<213> ORGANISM: Gossypium hirsutum

<400> SEQUENCE: 11

```
gcacaaggta aagcagtgta ccggcggcag tgatggaagt ggccgtgatc ggaggtggga     60

taaaagggtt gctttcggcc tacgtactgg tcaaagccgg cgtggacgtg gtggtttacg    120

agaaagaaga acaattaggc ggccatgcaa agactgttaa cttcgacgcc gttgatttag    180

accttggctt cttgtttctc aatccagcaa gatatgcaac actattgcat atgttcgaca    240

gccttggtgt tgatgtagaa acatccgatg tttcattctc tataagccat gacaaaggca    300

acaatggcta tgaatggtgc agccaatatg gattttccaa ttactttgct caaaagaaga    360

aactgttgaa ccctttcaat tggcaaagcc tcagagagat catcaaattc ggcaatgatg    420

tcgaaagtta ccttggatca cttgagaaca acccagacat tgatcgtact gagaccttgg    480

gacagtttat aaactcaaag ggctactctg aaaattttca aaacacttat ctggctccta    540

tatgtggttc aatgtggtca agctccaagg aagatgttac gagcttttca gctttttcca    600

tcctttcatt ttgccgtact catcatttgt accagctatt tgggcagtca cagtggttga    660

ctatcaaagg gcactcacat tttgttaaaa gggttaggga agtgctggag actaaaggtt    720

gtcaatttaa actcggttgt gaagtacaat ctgttttgcc cgttgataat ggtaccgcca    780

tggtctgtgg agatggtttc caagaaactt acaatggatg cataatggct gttgatgctc    840

ccactgccct aaaattatta ggaaaccaag caacatttga agaaacaaga gtactgggtg    900

ctttccaata tgctaccagt gatattttcc ttcaccagga cagtacttta atgccacaaa    960

acaaatcagc ttggagtgca ttgaattttc tcaatagtag caaaaataat gcattcttaa   1020
```

```
catactggct caatgcacta cagaatattg ggaaaacaag tgagccattt tttgtgactg   1080

tcaatccaga ccataccccg aagaatacct tacttaagtg gtcaaccggc catgcaatts   1140

cctctgttgc tgcatcaaaa gcttcacttg agcttggtca gattcaggga aagagaggaa   1200

tctggttctg tggctatgac ttcaatcagg atgaactaaa ggctggtatg gatgctgcac   1260

atggtatctt gggaaagcat tcttctgttc cgcccagtcc aaagaatatg tcaccctctt   1320

taccaaagaa tatgtcaccc tctttcatgg aaacaacggc acgcctcttt gttaccaaat   1380

tctttcaaca atatatatct atgggctgcg taattttttt agaggaagga ggcagaattt   1440

tcactttcaa aggaaacatg gaaaagtgtc ctcttaaaac agttctgaaa gtgcataatc   1500

ctcagtttta ctggaggatc atgaaagaag ctgatatagg ccttgcagac gcatatatcc   1560

atggagattt ttcttttctt gatgaaaatg aaggccttct taatcttttc cggattcttg   1620

ttgccaataa agagaactca gctgcctcag ggtcgactaa aagaaggact tggtggtcgc   1680

ctgctctgtt aacagctagt atatcatctg ccaagtattt tgtgaagcat ctcttaagac   1740

aaaatactat tacacaagct cgtaggaaca tttctcgtca ttatgatctg agtaatgaac   1800

ttttctctct atacttgggc aaaatgatgc aatactcttc tggagtcttt aggacaggag   1860

aagaacattt ggacgttgca cagcgaagaa aaatcagttc tctaattgag aaaacaagga   1920

tagagaaatg gcatgaagtt ctagacattg ggtgcggttg ggaagcttta gctattgaaa   1980

ctgtgaaaag aacaggatgc aaatatactg gcatcactct atcagaacag caactgaaat   2040

atgctcaaga aaaagtgaag gaagctggac tcgaggataa catcaaaata cttctctgtg   2100

actatcgcca gttacctaag gaacaccaat ttgacagaat catatctgta gagatggtag   2160

aacatgttgg tgaagaatat attgaggaat tttacagatg ctgtgatcaa ttactgaaag   2220

aagatggact tttcgttctt cagttcatat ctatcccaga ggagctttcc aaagaaatcc   2280

agcaaacagc tggttttctt aaggaatata tattccctgg tggaaccctg ctttctttgg   2340

ataggaattt atcagccatg gctgctgcaa caagattcag tgtggagcat gtggaaaaca   2400

taggaatgag ttattaccac acactgagat ggtggagaaa acttttcctg aaaaacacaa   2460

gcaaagttct ggctttgggg ttcgacgaga agttcatgcg gacatgggaa tactatttcg   2520

attactgtgc tgctggtttt aagacaggaa cccttataga ttaccaggtt gtattttctc   2580

gagccggtaa tttcggtaca cttggagatc catacaaagg tttcccttct gcatattcct   2640

tcatggatga ttgaacaaag tgtttgaata tatgatcacc atacaatgat tcaaccagct   2700

ggatcaaact ggtaccagtg tttacctagt cccctgcttt tgtttagtta tggttttcgt   2760

ttcgttgcga aaaagaaaaa agcaaataat gtatgttaat aatgaaatgt ttgtatctgg   2820

tatatctata ctggttggat tttatgtatg gagatctgtt tctttttaaa aaaaaaaaaa   2880

aaaa                                                                 2884
```

```
<210> SEQ ID NO 12
<211> LENGTH: 873
<212> TYPE: PRT
<213> ORGANISM: Gossypium hirsutum
<220> FEATURE:
<221> NAME/KEY: misc_feature
<222> LOCATION: (370)..(370)
<223> OTHER INFORMATION: Xaa can be any naturally occurring amino acid

<400> SEQUENCE: 12

Met Glu Val Ala Val Ile Gly Gly Gly Ile Lys Gly Leu Leu Ser Ala
1               5                   10                  15
```

```
Tyr Val Leu Val Lys Ala Gly Val Asp Val Val Val Tyr Glu Lys Glu
            20                  25                  30

Glu Gln Leu Gly Gly His Ala Lys Thr Val Asn Phe Asp Ala Val Asp
        35                  40                  45

Leu Asp Leu Gly Phe Leu Phe Leu Asn Pro Ala Arg Tyr Ala Thr Leu
    50                  55                  60

Leu His Met Phe Asp Ser Leu Gly Val Asp Val Glu Thr Ser Asp Val
65                  70                  75                  80

Ser Phe Ser Ile Ser His Asp Lys Gly Asn Asn Gly Tyr Glu Trp Cys
                85                  90                  95

Ser Gln Tyr Gly Phe Ser Asn Tyr Phe Ala Gln Lys Lys Lys Leu Leu
            100                 105                 110

Asn Pro Phe Asn Trp Gln Ser Leu Arg Glu Ile Ile Lys Phe Gly Asn
        115                 120                 125

Asp Val Glu Ser Tyr Leu Gly Ser Leu Glu Asn Asn Pro Asp Ile Asp
    130                 135                 140

Arg Thr Glu Thr Leu Gly Gln Phe Ile Asn Ser Lys Gly Tyr Ser Glu
145                 150                 155                 160

Asn Phe Gln Asn Thr Tyr Leu Ala Pro Ile Cys Gly Ser Met Trp Ser
                165                 170                 175

Ser Ser Lys Glu Asp Val Thr Ser Phe Ser Ala Phe Ser Ile Leu Ser
            180                 185                 190

Phe Cys Arg Thr His His Leu Tyr Gln Leu Phe Gly Gln Ser Gln Trp
        195                 200                 205

Leu Thr Ile Lys Gly His Ser His Phe Val Lys Arg Val Arg Glu Val
    210                 215                 220

Leu Glu Thr Lys Gly Cys Gln Phe Lys Leu Gly Cys Glu Val Gln Ser
225                 230                 235                 240

Val Leu Pro Val Asp Asn Gly Thr Ala Met Val Cys Gly Asp Gly Phe
                245                 250                 255

Gln Glu Thr Tyr Asn Gly Cys Ile Met Ala Val Asp Ala Pro Thr Ala
            260                 265                 270

Leu Lys Leu Leu Gly Asn Gln Ala Thr Phe Glu Glu Thr Arg Val Leu
        275                 280                 285

Gly Ala Phe Gln Tyr Ala Thr Ser Asp Ile Phe Leu His Gln Asp Ser
    290                 295                 300

Thr Leu Met Pro Gln Asn Lys Ser Ala Trp Ser Ala Leu Asn Phe Leu
305                 310                 315                 320

Asn Ser Ser Lys Asn Asn Ala Phe Leu Thr Tyr Trp Leu Asn Ala Leu
                325                 330                 335

Gln Asn Ile Gly Lys Thr Ser Glu Pro Phe Phe Val Thr Val Asn Pro
            340                 345                 350

Asp His Thr Pro Lys Asn Thr Leu Leu Lys Trp Ser Thr Gly His Ala
        355                 360                 365

Ile Xaa Ser Val Ala Ala Ser Lys Ala Ser Leu Glu Leu Gly Gln Ile
    370                 375                 380

Gln Gly Lys Arg Gly Ile Trp Phe Cys Gly Tyr Asp Phe Asn Gln Asp
385                 390                 395                 400

Glu Leu Lys Ala Gly Met Asp Ala Ala His Gly Ile Leu Gly Lys His
                405                 410                 415

Ser Ser Val Pro Pro Ser Pro Lys Asn Met Ser Pro Ser Leu Pro Lys
            420                 425                 430
```

```
Asn Met Ser Pro Ser Phe Met Glu Thr Thr Ala Arg Leu Phe Val Thr
        435                 440                 445

Lys Phe Phe Gln Gln Tyr Ile Ser Met Gly Cys Val Ile Phe Leu Glu
    450                 455                 460

Glu Gly Gly Arg Ile Phe Thr Phe Lys Gly Asn Met Glu Lys Cys Pro
465                 470                 475                 480

Leu Lys Thr Val Leu Lys Val His Asn Pro Gln Phe Tyr Trp Arg Ile
                485                 490                 495

Met Lys Glu Ala Asp Ile Gly Leu Ala Asp Ala Tyr Ile His Gly Asp
            500                 505                 510

Phe Ser Phe Leu Asp Glu Asn Glu Gly Leu Leu Asn Leu Phe Arg Ile
        515                 520                 525

Leu Val Ala Asn Lys Glu Asn Ser Ala Ala Ser Gly Ser Thr Lys Arg
    530                 535                 540

Arg Thr Trp Trp Ser Pro Ala Leu Leu Thr Ala Ser Ile Ser Ser Ala
545                 550                 555                 560

Lys Tyr Phe Val Lys His Leu Leu Arg Gln Asn Thr Ile Thr Gln Ala
                565                 570                 575

Arg Arg Asn Ile Ser Arg His Tyr Asp Leu Ser Asn Glu Leu Phe Ser
            580                 585                 590

Leu Tyr Leu Gly Lys Met Met Gln Tyr Ser Ser Gly Val Phe Arg Thr
        595                 600                 605

Gly Glu Glu His Leu Asp Val Ala Gln Arg Arg Lys Ile Ser Ser Leu
    610                 615                 620

Ile Glu Lys Thr Arg Ile Glu Lys Trp His Glu Val Leu Asp Ile Gly
625                 630                 635                 640

Cys Gly Trp Gly Ser Leu Ala Ile Glu Thr Val Lys Arg Thr Gly Cys
                645                 650                 655

Lys Tyr Thr Gly Ile Thr Leu Ser Glu Gln Gln Leu Lys Tyr Ala Gln
            660                 665                 670

Glu Lys Val Lys Glu Ala Gly Leu Glu Asp Asn Ile Lys Ile Leu Leu
        675                 680                 685

Cys Asp Tyr Arg Gln Leu Pro Lys Glu His Gln Phe Asp Arg Ile Ile
    690                 695                 700

Ser Val Glu Met Val Glu His Val Gly Glu Glu Tyr Ile Glu Glu Phe
705                 710                 715                 720

Tyr Arg Cys Cys Asp Gln Leu Leu Lys Glu Asp Gly Leu Phe Val Leu
                725                 730                 735

Gln Phe Ile Ser Ile Pro Glu Glu Leu Ser Lys Glu Ile Gln Gln Thr
            740                 745                 750

Ala Gly Phe Leu Lys Glu Tyr Ile Phe Pro Gly Gly Thr Leu Leu Ser
        755                 760                 765

Leu Asp Arg Asn Leu Ser Ala Met Ala Ala Ala Thr Arg Phe Ser Val
    770                 775                 780

Glu His Val Glu Asn Ile Gly Met Ser Tyr Tyr His Thr Leu Arg Trp
785                 790                 795                 800

Trp Arg Lys Leu Phe Leu Lys Asn Thr Ser Lys Val Leu Ala Leu Gly
                805                 810                 815

Phe Asp Glu Lys Phe Met Arg Thr Trp Glu Tyr Tyr Phe Asp Tyr Cys
            820                 825                 830

Ala Ala Gly Phe Lys Thr Gly Thr Leu Ile Asp Tyr Gln Val Val Phe
        835                 840                 845

Ser Arg Ala Gly Asn Phe Gly Thr Leu Gly Asp Pro Tyr Lys Gly Phe
```

850 855 860

Pro Ser Ala Tyr Ser Phe Met Asp Asp
865 870

<210> SEQ ID NO 13
<211> LENGTH: 2827
<212> TYPE: DNA
<213> ORGANISM: Gossypium hirsutum

<400> SEQUENCE: 13
gtcacggcgg cagtgatgga agtggcggtg atcggaggtg ggataaaagg gttggtttcg 60
gcctacgtac tggtcaaagc cggcgtggac gtggtggttt acgagaaaga agagcaatta 120
ggcggccatg cgaagactgt taacttcgac gccgttgact tagaccttgg cttcttgttt 180
cttaatcctg caagatatgc aacactgttg gatataatcg acagccttgg tgttgatgta 240
gaaacatccg atgtttcatt ctctataagc catgacaaag gcaacaatgg ctatgaatgg 300
tgcagtcaat atggattttc caattacttt gcacaaaaga agaaactgtt gaaccctttc 360
aattggcaaa accttagaga gatcatcaga ttcagcaacg atgtcgaaag ttaccttgga 420
tcacttgaga acaacccaga cattgatcgt actgagacct tgggacagtt tataaaatca 480
aagggctact ctgaaaattt tcaaaacact tacctggctc ctatatgtgg ttcaatgtgg 540
tcaagctcca aggaagatgt tatgagcttt tcagcatttt ccatcctttc attttgccgt 600
actcatcatt tgtaccagca atttgggcag ccacagtggt tgactatcaa agggcactca 660
cattttgtta aaagggttag ggaagtgctg gagactaaag gttgtcaatt taaactcggt 720
tgtgaagtac aatctgtttt gcctgctgat aatggtacca ccatggtctg tggagatggt 780
ttccaagaaa cttacaatgg atgcataatg gctgttgatg ctcccactgc cctaaaatta 840
ttaggaaacc aagcaacatt tgaagaaaca agagtactgg gtgctttcca atatgctacc 900
agtgatattt tccttcaccg ggacagtact ttaatgccac aaaacaaatc agcttggagt 960
gcattgaatt ttctcaatag tagcaaaaat aatgcattct taacatactg gctcaatgca 1020
ctacagaata ttgggaaaac aagtgagcca ttttttgtga ctgtcaatcc agaccatacc 1080
ccgaagaata ccttgcttaa gtggtcgact ggccatgcaa ttccctctgt tgctgcatca 1140
aaagcttcac ttgagcttgg tcagattcag gggaagagag gaatctggtt ctgtggctat 1200
gacttcaatc aggatgaact aaaggctggt atggatgctg cacatggtat cttgggaaag 1260
cattcttctg ttctgcatag tccaaagagt atgtcaccct ctttcatgga aacaacggca 1320
cgcctctttg ttactaaatt ctttcaacaa tatatatcta tgggctgtgt aatttttctta 1380 gaggaaggag gcagaatttt cactttcaaa ggaaacatgg aaaagtgtcc tcttaaaaca 1440
gttctgaaag tacataatcc tcagttttac tggaggatca tgaaagaagc tgatataggc 1500
cttgcagatg catatatcca tggagatttt tcttttcttg atgaaactga aggccttctt 1560
aatcttttcc ggattcttgt tgccaataaa gagaactcag ctgcctcagg gtcgaataaa 1620
agaaggactt ggtggtcacc tgctctgtta acagctagta tatcatctgc aaagtatttt 1680
gtgaagcatc tcttgagaca aaatactatt acacaagctc gtaggaacat ttctcgtcat 1740
tatgatctga gtaatgaact tttcactcta tacttgggca aaatgatgca atactcttct 1800
ggagtcttta ggacgggaga agaacatttg gacgttgcac agcgtagaaa aatcagttct 1860
ctaattgaga aagcaaggat agagaaacgg cacgaagttc tcgacattgg gtgcggttgg 1920
ggaagcttag ctattgaaac tgtgaaaaga acaggatgca aatatactgg catcactcta 1980

-continued

```
tcagaacagc aactgaaata tgctcaagaa aaagtgaagg aagctggact ccaggataac   2040

atcaaaatac ttctctgtga ctatcgccag ttacctaagg aacaccaatt tgacagaatc   2100

atatctgtag agatggtaga acatgttggt gaagaatata ttgaggagtt ttacagatgc   2160

tgtgaccaat tactgaaaga agatgggctt tttgttcttc agttcatatc tatcccagaa   2220

gagctttcca aagaaatcca gcaaacagca ggtttttctaa aggaatatat attccctgga   2280

ggaaccctgc tttctttgga taggaattta tcagccatgg ctgctgcaac aagattcagt   2340

gtggagcatg tggaaaatat aggaatgagt tattaccaca cactgagatg gtggagaaaa   2400

cttttcctgg aaaacacaag caaagttcta gctctggggt tcgacgagaa gttcatgagg   2460

acatgggaat actatttcga ttactgcgct gccggtttta agacaggaac tcttatagat   2520

taccaggttg tattttcaag ggccggaaat ttcggtacac tcggagatcc atacaaaggt   2580

ttcccttctg catattcctt catggatgat tgaacaaagt gtggttgaac attgatccaa   2640

agaagcaaac aaaattatca ccacatgcca gtgttaagaa caacctatct ccctagtccc   2700

tacttttgtt tattatggct atgtttgcaa tgcaagaata agcaaacatt gtaatgttaa   2760

taaagtttgc acttttgtag actggatgga tgttatcaat gaagtaccta gtttataaaa   2820

aaaaaaa                                                              2827
```

```
<210> SEQ ID NO 14
<211> LENGTH: 865
<212> TYPE: PRT
<213> ORGANISM: Gossypium hirsutum

<400> SEQUENCE: 14

Met Glu Val Ala Val Ile Gly Gly Gly Ile Lys Gly Leu Val Ser Ala
1               5                   10                  15

Tyr Val Leu Val Lys Ala Gly Val Asp Val Val Val Tyr Glu Lys Glu
            20                  25                  30

Glu Gln Leu Gly Gly His Ala Lys Thr Val Asn Phe Asp Ala Val Asp
        35                  40                  45

Leu Asp Leu Gly Phe Leu Phe Leu Asn Pro Ala Arg Tyr Ala Thr Leu
    50                  55                  60

Leu Asp Ile Ile Asp Ser Leu Gly Val Asp Val Glu Thr Ser Asp Val
65                  70                  75                  80

Ser Phe Ser Ile Ser His Asp Lys Gly Asn Asn Gly Tyr Glu Trp Cys
                85                  90                  95

Ser Gln Tyr Gly Phe Ser Asn Tyr Phe Ala Gln Lys Lys Lys Leu Leu
            100                 105                 110

Asn Pro Phe Asn Trp Gln Asn Leu Arg Glu Ile Ile Arg Phe Ser Asn
        115                 120                 125

Asp Val Glu Ser Tyr Leu Gly Ser Leu Glu Asn Asn Pro Asp Ile Asp
    130                 135                 140

Arg Thr Glu Thr Leu Gly Gln Phe Ile Lys Ser Lys Gly Tyr Ser Glu
145                 150                 155                 160

Asn Phe Gln Asn Thr Tyr Leu Ala Pro Ile Cys Gly Ser Met Trp Ser
                165                 170                 175

Ser Ser Lys Glu Asp Val Met Ser Phe Ser Ala Phe Ser Ile Leu Ser
            180                 185                 190

Phe Cys Arg Thr His His Leu Tyr Gln Gln Phe Gly Gln Pro Gln Trp
        195                 200                 205

Leu Thr Ile Lys Gly His Ser His Phe Val Lys Arg Val Arg Glu Val
    210                 215                 220
```

-continued

```
Leu Glu Thr Lys Gly Cys Gln Phe Lys Leu Gly Cys Glu Val Gln Ser
225                 230                 235                 240

Val Leu Pro Ala Asp Asn Gly Thr Thr Met Val Cys Gly Asp Gly Phe
                245                 250                 255

Gln Glu Thr Tyr Asn Gly Cys Ile Met Ala Val Asp Ala Pro Thr Ala
            260                 265                 270

Leu Lys Leu Leu Gly Asn Gln Ala Thr Phe Glu Glu Thr Arg Val Leu
        275                 280                 285

Gly Ala Phe Gln Tyr Ala Thr Ser Asp Ile Phe Leu His Arg Asp Ser
    290                 295                 300

Thr Leu Met Pro Gln Asn Lys Ser Ala Trp Ser Ala Leu Asn Phe Leu
305                 310                 315                 320

Asn Ser Ser Lys Asn Asn Ala Phe Leu Thr Tyr Trp Leu Asn Ala Leu
                325                 330                 335

Gln Asn Ile Gly Lys Thr Ser Glu Pro Phe Phe Val Thr Val Asn Pro
            340                 345                 350

Asp His Thr Pro Lys Asn Thr Leu Leu Lys Trp Ser Thr Gly His Ala
        355                 360                 365

Ile Pro Ser Val Ala Ala Ser Lys Ala Ser Leu Glu Leu Gly Gln Ile
    370                 375                 380

Gln Gly Lys Arg Gly Ile Trp Phe Cys Gly Tyr Asp Phe Asn Gln Asp
385                 390                 395                 400

Glu Leu Lys Ala Gly Met Asp Ala Ala His Gly Ile Leu Gly Lys His
                405                 410                 415

Ser Ser Val Leu His Ser Pro Lys Ser Met Ser Pro Ser Phe Met Glu
            420                 425                 430

Thr Thr Ala Arg Leu Phe Val Thr Lys Phe Phe Gln Gln Tyr Ile Ser
        435                 440                 445

Met Gly Cys Val Ile Phe Leu Glu Glu Gly Gly Arg Ile Phe Thr Phe
    450                 455                 460

Lys Gly Asn Met Glu Lys Cys Pro Leu Lys Thr Val Leu Lys Val His
465                 470                 475                 480

Asn Pro Gln Phe Tyr Trp Arg Ile Met Lys Glu Ala Asp Ile Gly Leu
                485                 490                 495

Ala Asp Ala Tyr Ile His Gly Asp Phe Ser Phe Leu Asp Glu Thr Glu
            500                 505                 510

Gly Leu Leu Asn Leu Phe Arg Ile Leu Val Ala Asn Lys Glu Asn Ser
        515                 520                 525

Ala Ala Ser Gly Ser Asn Lys Arg Arg Thr Trp Trp Ser Pro Ala Leu
    530                 535                 540

Leu Thr Ala Ser Ile Ser Ser Ala Lys Tyr Phe Val Lys His Leu Leu
545                 550                 555                 560

Arg Gln Asn Thr Ile Thr Gln Ala Arg Arg Asn Ile Ser Arg His Tyr
                565                 570                 575

Asp Leu Ser Asn Glu Leu Phe Thr Leu Tyr Leu Gly Lys Met Met Gln
            580                 585                 590

Tyr Ser Ser Gly Val Phe Arg Thr Gly Glu Glu His Leu Asp Val Ala
        595                 600                 605

Gln Arg Arg Lys Ile Ser Ser Leu Ile Glu Lys Ala Arg Ile Glu Lys
    610                 615                 620

Arg His Glu Val Leu Asp Ile Gly Cys Gly Trp Gly Ser Leu Ala Ile
625                 630                 635                 640
```

Glu Thr Val Lys Arg Thr Gly Cys Lys Tyr Thr Gly Ile Thr Leu Ser
645 650 655

Glu Gln Gln Leu Lys Tyr Ala Gln Glu Lys Val Lys Glu Ala Gly Leu
660 665 670

Gln Asp Asn Ile Lys Ile Leu Leu Cys Asp Tyr Arg Gln Leu Pro Lys
675 680 685

Glu His Gln Phe Asp Arg Ile Ile Ser Val Glu Met Val Glu His Val
690 695 700

Gly Glu Glu Tyr Ile Glu Glu Phe Tyr Arg Cys Cys Asp Gln Leu Leu
705 710 715 720

Lys Glu Asp Gly Leu Phe Val Leu Gln Phe Ile Ser Ile Pro Glu Glu
725 730 735

Leu Ser Lys Glu Ile Gln Gln Thr Ala Gly Phe Leu Lys Glu Tyr Ile
740 745 750

Phe Pro Gly Gly Thr Leu Leu Ser Leu Asp Arg Asn Leu Ser Ala Met
755 760 765

Ala Ala Ala Thr Arg Phe Ser Val Glu His Val Glu Asn Ile Gly Met
770 775 780

Ser Tyr Tyr His Thr Leu Arg Trp Trp Arg Lys Leu Phe Leu Glu Asn
785 790 795 800

Thr Ser Lys Val Leu Ala Leu Gly Phe Asp Glu Lys Phe Met Arg Thr
805 810 815

Trp Glu Tyr Tyr Phe Asp Tyr Cys Ala Ala Gly Phe Lys Thr Gly Thr
820 825 830

Leu Ile Asp Tyr Gln Val Val Phe Ser Arg Ala Gly Asn Phe Gly Thr
835 840 845

Leu Gly Asp Pro Tyr Lys Gly Phe Pro Ser Ala Tyr Ser Phe Met Asp
850 855 860

Asp
865

<210> SEQ ID NO 15
<211> LENGTH: 2912
<212> TYPE: DNA
<213> ORGANISM: Gossypium hirsutum

<400> SEQUENCE: 15
tccctatctc catttactat tttcttctct cttcttcttc tttcgaacca ttttcagagt 60
tcataaattc agggttttgt tttttttttg ggtgtagtga aataaaggat gaaaatagca 120
gtgataggag gagggataag tggggtggta tcagcctata ctttagccaa agccggtgca 180
aatgtagtgc tttacgagaa agaagagtat ttgggaggcc attccaagac cgttcacttc 240
gatggtgttg atttagacct tggtttcatg gtttttaatc gcgttacata tccaaatatg 300
atggagttgt ttgagagcct tgggattgat atggaaccat ttgatatgtc actctcagtg 360
agccttaatg aaggcaaagg ctgtgaatgg ggcagccgta atggcctttc ggccttgttt 420
gcccaaaaat ccaacctctt caatccttac ttttggcaaa tgcttagaga aattctcaaa 480
ttcaagaatg atgttattag ttatcttgaa ttgctcgaaa acaacccgga tattgaccgt 540
aatgaaacat tgggacagtt cataaaatca aagggttact ctgatttatt tcagaaggct 600
tatctggtgc ctgtatgtgg ttcaatatgg tcatgcccta cagaaagagt tatggatttt 660
tcagctttct ctattctttc attttgccgc aatcatcatc tacttcagat ctttggacga 720
ccacagtgga tgaccgttcg atggcgttca catcgttacg tcaataaggt tagagaagag 780

-continued

```
ctggagagta caggttgtca aataagaact ggttgcgagg tgcattctgt tttgagtgat    840
gctgaaggtt gcactgtatt atgtggagat gactctcacg agttatatca agggtgcata    900
atggctgttc atgcaccata tgctttgaga ttgttaggga atcaagcaac atatgatgaa    960
tcaacagtgc ttggcgcttt ccaatatgtc tatagtgata tttatcttca tcgtgacaaa   1020
aatttaatgc ccaaaaaccc agcagcatgg agtgcatgga attttcttgg aagtacagac   1080
aagaatgtat ctttgacata ctggcttaat gtgcttcaga atctaggaga aacaagccta   1140
cccttttttgg tcactctcaa tccagattat acaccaaaac acaccttgct taagtggaga   1200
acaggccatc cagtaccatc tgttgctgca acaaaagctt ctcttgagct tgatcggatt   1260
caagggaaga gaggaatttg gttttgtgga gcatacctgg gctatggctt ccatgaagat   1320
ggattaaagg ctgggatgat tgctgcaaac ggtctgctgg gaaaaagttg taatattctg   1380
agcaatccaa agcatatggt gccctctctg atggaaacag gggcacgtct tttgttact   1440
agattcctca gtcattttat atcaaccggc tgtgtgattt tattggaaga aggtggcact   1500
atgtttacct ttgaaggaac tagcaataag tgttctctaa aaactgtaat taaagttcac   1560
agtccacatt tttattggaa ggttatgaca gaggcagatt taggccttgc agattcatat   1620
atcaatgggg atttttcttt tgttgataaa aaagacggtc tgctgaacct tgtaatgatt   1680
cttattgcca acagagattt gatttcttcc aactcaaaac ttagtaagaa aaggggttgg   1740
tggacaccat tgttgtttac agctggtcta acatcagcaa agtatttctt caagcatgtc   1800
ttaagacaaa atactcttac acaagctcgt aggaacattt ctcgccatta cgacytgagt   1860
aatgaccttt ttgcactctt cttggatgag acaatgacat actcttgtgc agtatttaag   1920
acagaagatg aggatttgaa agatgcacaa cacagaaaga tctctctttt gattgaaaaa   1980
gcaagaattg atagcaagca tgaaattctt gagattggat gtggttgggk aagcttagct   2040
attgaggttg tcaaacgaac tggatgcaaa tataccggca ttactttatc cgaagagcaa   2100
ctcaaacttg cagaaaaaag agtgaaggaa gctggacttc aggaaaatat aagatttcaa   2160
ctctgtgact atcgacaact acctagcacc tacaagtatg acagaattat atcgtgtgag   2220
atgatagaag ctgttggcca tgaatacatg gaggacttct tcggttgctg tgaatcagtg   2280
ttagcagatg atggacttct tgttttacag ttcatatcaa taccagagga acggtacaat   2340
gaatacaggc gaagctcgga tttcatcaag gaatacatct tccctggtgg atgcttacct   2400
tctctggcta ggataacaac agccatgaat gctgcgtcca aactctgtgt ggagcatgtg   2460
gaaaacatcg gacttcatta ctaccaaacg cttagatatt ggagaaagaa tttcttggag   2520
aaacagagca aaatccatgc cttgggattc aatgacaagt tcatccggac atgggaatac   2580
tattttgatt attgtgctgc tggtttcaag tccaatactc ttggtaatta ccaggttgta   2640
ttttctcggc ctggaaatgt agttgcactt ggcaacccat acaaagactt cccctcagct   2700
tcttaattat ttattttctc cttatttcaa tcgtaccata gccataattt gagcttgttg   2760
aaaactgatg ctacacgttt ggtttcattc aaatatggta tttgagtgca tatctataca   2820
ttgatgaatg taattctggc ttgcctcgta ggaacttgcc agcaggatta tctttttaca   2880
tggacattta ttttaattct ctgttcaaat tt                                 2912
```

<210> SEQ ID NO 16
<211> LENGTH: 865
<212> TYPE: PRT
<213> ORGANISM: Gossypium hirsutum
<220> FEATURE:
<221> NAME/KEY: misc_feature
<222> LOCATION: (641)..(641)
<223> OTHER INFORMATION: Xaa can be any naturally occurring amino acid

<400> SEQUENCE: 16

Met Lys Ile Ala Val Ile Gly Gly Gly Ile Ser Gly Val Val Ser Ala
1 5 10 15

Tyr Thr Leu Ala Lys Ala Gly Ala Asn Val Val Leu Tyr Glu Lys Glu
20 25 30

Glu Tyr Leu Gly Gly His Ser Lys Thr Val His Phe Asp Gly Val Asp
35 40 45

Leu Asp Leu Gly Phe Met Val Phe Asn Arg Val Thr Tyr Pro Asn Met
50 55 60

Met Glu Leu Phe Glu Ser Leu Gly Ile Asp Met Glu Pro Phe Asp Met
65 70 75 80

Ser Leu Ser Val Ser Leu Asn Glu Gly Lys Gly Cys Glu Trp Gly Ser
85 90 95

Arg Asn Gly Leu Ser Ala Leu Phe Ala Gln Lys Ser Asn Leu Phe Asn
100 105 110

Pro Tyr Phe Trp Gln Met Leu Arg Glu Ile Leu Lys Phe Lys Asn Asp
115 120 125

Val Ile Ser Tyr Leu Glu Leu Leu Glu Asn Asn Pro Asp Ile Asp Arg
130 135 140

Asn Glu Thr Leu Gly Gln Phe Ile Lys Ser Lys Gly Tyr Ser Asp Leu
145 150 155 160

Phe Gln Lys Ala Tyr Leu Val Pro Val Cys Gly Ser Ile Trp Ser Cys
165 170 175

Pro Thr Glu Arg Val Met Asp Phe Ser Ala Phe Ser Ile Leu Ser Phe
180 185 190

Cys Arg Asn His His Leu Leu Gln Ile Phe Gly Arg Pro Gln Trp Met
195 200 205

Thr Val Arg Trp Arg Ser His Arg Tyr Val Asn Lys Val Arg Glu Glu
210 215 220

Leu Glu Ser Thr Gly Cys Gln Ile Arg Thr Gly Cys Glu Val His Ser
225 230 235 240

Val Leu Ser Asp Ala Glu Gly Cys Thr Val Leu Cys Gly Asp Asp Ser
245 250 255

His Glu Leu Tyr Gln Gly Cys Ile Met Ala Val His Ala Pro Tyr Ala
260 265 270

Leu Arg Leu Leu Gly Asn Gln Ala Thr Tyr Asp Glu Ser Thr Val Leu
275 280 285

Gly Ala Phe Gln Tyr Val Tyr Ser Asp Ile Tyr Leu His Arg Asp Lys
290 295 300

Asn Leu Met Pro Lys Asn Pro Ala Ala Trp Ser Ala Trp Asn Phe Leu
305 310 315 320

Gly Ser Thr Asp Lys Asn Val Ser Leu Thr Tyr Trp Leu Asn Val Leu
325 330 335

Gln Asn Leu Gly Glu Thr Ser Leu Pro Phe Leu Val Thr Leu Asn Pro
340 345 350

Asp Tyr Thr Pro Lys His Thr Leu Leu Lys Trp Arg Thr Gly His Pro
355 360 365

Val Pro Ser Val Ala Ala Thr Lys Ala Ser Leu Glu Leu Asp Arg Ile
370 375 380

Gln Gly Lys Arg Gly Ile Trp Phe Cys Gly Ala Tyr Leu Gly Tyr Gly
385 390 395 400

```
Phe His Glu Asp Gly Leu Lys Ala Gly Met Ile Ala Ala Asn Gly Leu
                405                 410                 415

Leu Gly Lys Ser Cys Asn Ile Leu Ser Asn Pro Lys His Met Val Pro
            420                 425                 430

Ser Leu Met Glu Thr Gly Ala Arg Leu Phe Val Thr Arg Phe Leu Ser
        435                 440                 445

His Phe Ile Ser Thr Gly Cys Val Ile Leu Leu Glu Glu Gly Gly Thr
    450                 455                 460

Met Phe Thr Phe Glu Gly Thr Ser Asn Lys Cys Ser Leu Lys Thr Val
465                 470                 475                 480

Ile Lys Val His Ser Pro His Phe Tyr Trp Lys Val Met Thr Glu Ala
                485                 490                 495

Asp Leu Gly Leu Ala Asp Ser Tyr Ile Asn Gly Asp Phe Ser Phe Val
            500                 505                 510

Asp Lys Lys Asp Gly Leu Leu Asn Leu Val Met Ile Leu Ile Ala Asn
        515                 520                 525

Arg Asp Leu Ile Ser Ser Asn Ser Lys Leu Ser Lys Lys Arg Gly Trp
    530                 535                 540

Trp Thr Pro Leu Leu Phe Thr Ala Gly Leu Thr Ser Ala Lys Tyr Phe
545                 550                 555                 560

Phe Lys His Val Leu Arg Gln Asn Thr Leu Thr Gln Ala Arg Arg Asn
                565                 570                 575

Ile Ser Arg His Tyr Asp Leu Ser Asn Asp Leu Phe Ala Leu Phe Leu
            580                 585                 590

Asp Glu Thr Met Thr Tyr Ser Cys Ala Val Phe Lys Thr Glu Asp Glu
        595                 600                 605

Asp Leu Lys Asp Ala Gln His Arg Lys Ile Ser Leu Leu Ile Glu Lys
    610                 615                 620

Ala Arg Ile Asp Ser Lys His Glu Ile Leu Glu Ile Gly Cys Gly Trp
625                 630                 635                 640

Xaa Ser Leu Ala Ile Glu Val Val Lys Arg Thr Gly Cys Lys Tyr Thr
                645                 650                 655

Gly Ile Thr Leu Ser Glu Glu Gln Leu Lys Leu Ala Glu Lys Arg Val
            660                 665                 670

Lys Glu Ala Gly Leu Gln Glu Asn Ile Arg Phe Gln Leu Cys Asp Tyr
        675                 680                 685

Arg Gln Leu Pro Ser Thr Tyr Lys Tyr Asp Arg Ile Ile Ser Cys Glu
    690                 695                 700

Met Ile Glu Ala Val Gly His Glu Tyr Met Glu Asp Phe Phe Gly Cys
705                 710                 715                 720

Cys Glu Ser Val Leu Ala Asp Asp Gly Leu Leu Val Leu Gln Phe Ile
                725                 730                 735

Ser Ile Pro Glu Glu Arg Tyr Asn Glu Tyr Arg Arg Ser Ser Asp Phe
            740                 745                 750

Ile Lys Glu Tyr Ile Phe Pro Gly Gly Cys Leu Pro Ser Leu Ala Arg
        755                 760                 765

Ile Thr Thr Ala Met Asn Ala Ala Ser Lys Leu Cys Val Glu His Val
    770                 775                 780

Glu Asn Ile Gly Leu His Tyr Tyr Gln Thr Leu Arg Tyr Trp Arg Lys
785                 790                 795                 800

Asn Phe Leu Glu Lys Gln Ser Lys Ile His Ala Leu Gly Phe Asn Asp
                805                 810                 815
```

-continued

```
Lys Phe Ile Arg Thr Trp Glu Tyr Tyr Phe Asp Tyr Cys Ala Ala Gly
            820                 825                 830

Phe Lys Ser Asn Thr Leu Gly Asn Tyr Gln Val Val Phe Ser Arg Pro
        835                 840                 845

Gly Asn Val Val Ala Leu Gly Asn Pro Tyr Lys Asp Phe Pro Ser Ala
    850                 855                 860

Ser
865


<210> SEQ ID NO 17
<211> LENGTH: 22
<212> TYPE: DNA
<213> ORGANISM: Artificial
<220> FEATURE:
<223> OTHER INFORMATION: Primer

<400> SEQUENCE: 17

atggtgggtg cgtcttcctc tt                                              22


<210> SEQ ID NO 18
<211> LENGTH: 23
<212> TYPE: DNA
<213> ORGANISM: Artificial
<220> FEATURE:
<223> OTHER INFORMATION: Primer

<400> SEQUENCE: 18

cactacaaca tagaaggtat gtg                                             23


<210> SEQ ID NO 19
<211> LENGTH: 30
<212> TYPE: DNA
<213> ORGANISM: Artificial
<220> FEATURE:
<223> OTHER INFORMATION: Primer

<400> SEQUENCE: 19

ccatggctaa tcgcgatgga tttgtcatgg                                      30


<210> SEQ ID NO 20
<211> LENGTH: 28
<212> TYPE: DNA
<213> ORGANISM: Artificial
<220> FEATURE:
<223> OTHER INFORMATION: Primer

<400> SEQUENCE: 20

ccatggctct tcggccaaat gtaagaaa                                        28


<210> SEQ ID NO 21
<211> LENGTH: 26
<212> TYPE: DNA
<213> ORGANISM: Artificial
<220> FEATURE:
<223> OTHER INFORMATION: Primer

<400> SEQUENCE: 21

cccgggcgta ttgcctgtac cgttgc                                          26


<210> SEQ ID NO 22
<211> LENGTH: 6541
<212> TYPE: DNA
<213> ORGANISM: Gossypium hirsutum

<400> SEQUENCE: 22
```

-continued

```
aattatttaa tggaaaaatt aatttattta aattaataaa taatgtctat tctgggttgg     60
attaaattat aaagtgttag gttaaaagtc caaaaagcac ttataatttg actcgataca    120
agagagcctc aaaacccttc atagtaatca ttagggatga aaaccttagt aaaataacta    180
gggttagcca cccctctctc ctagttcaac taagagattg tttttctatt aaataggcat    240
taaatgcatt ctactaattc aactagagtt tcacttcctc tccctataaa tagatgacac    300
cgatagggct aaaaatagaa gaatttatat acaactttga gatcttgtta tctacccgaa    360
aatagtgaga atttattttt aagtataaat tttattttcc gatagtaaca attctactgg    420
tttctataag agagatatat ttactttcca actgaaagta aaggaactat tattggttct    480
gtgtttgatt caaaattatt tgagcccatg ctcgaagtag ttcatggtcg agaatagcag    540
agaaggtcat tcggttgaaa gctaggaatg tctaggatcc gcctagccca aaacacaggt    600
actattttgg gaaaaaaagt ttattgttat aaatatcaca aaccggctcg gttttcaaaa    660
ttttgttttt ttgttgtaca aaccactttc gaaccaaatt ttttccaata tgagtagcat    720
aaggagttga gctataggtc ggtcagtgga aaggtaagga agactttgag gtaattcatt    780
tagatgatta cgactatgtt cttggcttga atatccttgg caagattaat gctctattgg    840
ttccttttgc tggtggcata tgtatcttgg acacttgtta acgacaatgt gttgtgctgg    900
tggatcatga tgagaaatga ggagccaagg tattgtcgac aattcaacta gctaaagatg    960
tttattttgg ataaaaacat tgacttggta gatcgaagtg ctacaaagac ccccttagaa   1020
atgctagagg tgaaaaaaac caatataaag cttgttgagt tatcagtgag gttaccactt   1080
atgagagagg tgggttgtgt attgggcttc gtgggaaaag tggtgatgca agttggacag   1140
ttaaatcaag taaatgttac aagcaaggta catctcaaac actttcttag tgttctacat   1200
tatgacttac tgttgtcttg gaaaaaacac atgaaccctt tttcagttct gaagtgggta   1260
agctgagggg cttacaaacc aaagttggca ttaatactca aggttaactc agtgttcaat   1320
atgggcatgc ctaagcctat ttgtgtaaat caaggggatc cgaccaaggt aagtcacaat   1380
tggggcaagt aagagcggtg agctctttca atcgagatgt tcgaaagaga gaaatggttt   1440
gacttagacg acggtagaga cataagttga ggcaaaggtt ccgaaggaag ggactaccta   1500
acatagacaa tagtaaggaa tcgacccgag gcattgaggt cgtttcaaga tgagtcaaac   1560
tagtgtcatt ccgaggacac aacgaggatt cgtgagaatg ggtgaaaaag aatgtcacgg   1620
actgtggatc gaagcccatg acaaatgcac atagaacgtc ccatggaggt taattgatta   1680
aatgaggctt atttaatcca catgaactgg catggtttgt gaaatacata aagaagctca   1740
tctacttgaa ccttagtagc cctatggacc actccagtaa aactagagtt accatggtta   1800
atatttgtaa tcttaaaaga taagattgta tagagtttaa atccttcaga actttcatct   1860
tgtagataga ctttaatctc gactatcgat gtgatttaaa ttgaccgtta gatttggggg   1920
agctcaacta taaataaagg tcttcccccct catttgtaat catttagttg tttttcttca   1980
aagtaatata acacttttga gagcatttac ttaaacactt agtgtgttta gttttcttgt   2040
ggcttttctg ttcatttttt gcttctttgc ttgaaagttt gtttcaattt tattttagtg   2100
ccttagaaaa tttctattgt taattttcat ctttcgagag ttaggctgac ttaggcaaat   2160
ttaaagctaa gtttcgtgat ttcaagttgt ttcttaaaaa gaagctttca aatctacaat   2220
ggatagctat tactctattg tctaggaact tctcattttt cagttgcatt tgattttcct   2280
ttcgattcat gttctactct aagttcctta caacatttca tatgtttaaa gagagattta   2340
```

```
ttttagaaag aatgatttag aaattctatc attagttttt cgttttccct ttgtagtatg   2400
aaactgaaag caaattagta gaaaataata aaaattgaaa aagaaaactt gatttttttt   2460
gggaaaatgt aaaaataatt tttagaaata aaatatatta aaccatttta tatttttaaa   2520
tattttatat aatttttttt attttgaaga aaattttaat ttttagtgaa taattttaat   2580
ttttagtgaa tttatataaa tttcaaattt taaaaaaaaa ttgataagag attatttcca   2640
tgaaaagtaa aataaaatgg aagaattgct cataagggat tgagctagca atcaaaggtt   2700
aataaataga cacgtggcat cccctgattg gtcagtgtgc catgtcatca attttttaac   2760
ggattaagat taagtatctt tactattaac aagattaaat atctgaaatt ttgtttatat   2820
attacataca taaataatta tttttatcta atataaaaat aaattgatgt atttatttct   2880
ttaaatgtgt atgacttaaa ttaaaattaa agtttcaagt atatatttga accacaatta   2940
gagtttcatg tatataatta cactaaatta aagttcatat aattgcacat taaatcaaaa   3000
ttcatatgta attttaaaat tcaccccttt ctttaaatat tcattttatt ttttatattc   3060
aaacttgtca ttatattcac aactgtcacc tgacatttaa tttaagagaa aggattgtat   3120
gaaataggga cattattacg ttccaatagt tttgtgccca ttaacatttt catcctgaat   3180
ttcaagattt tcatttggat ttgatttttt tcaggacgaa attgttgaaa ttcagaataa   3240
aaataatgat ataatataca actattaaaa acagtggtgg atctagggga ctcgcaggac   3300
cccgaccccc ctaaaataga aaattattca tttaaggctt ttaaaaattt taaaatttta   3360
aattaataaa aataaaatta cactttaacc tcttaaaaat aataaaaatt taatttaata   3420
ctttaaaatt ataaaaatat taactattaa aatttaaaat ttaattttag ctcccaacat   3480
aaatttttga cttcacccct aatcacacgg taattctttc ttttattcga aagaaaggat   3540
ggtccacgta attaaactgc cattgcatgt tttcttgcca ccactagtct agtctactgc   3600
acagtgtgtg tttaagctag aggtgatcat gggttgggct acccggcccg acctgacggt   3660
ccgtccgaaa aataagaggg ttcgggtaaa aatataggct cgaaatatgg gtttgagtaa   3720
aaaatgaggc ccggttagaa aacaggctgg gcctcgagta aaactttttt tctcgggcct   3780
ggcccgaatt atgtattaaa tatatatttt ttatttttaa tcaaatatac ttttttaatc   3840
aaatatatat taaatatata ctttttagt gttgtaaatt ttaatatggg tcggcccggg   3900
ccgagctcgg gcttagcaat tttttccggg tcggacttgg ataaattttt aggctcatat   3960
ttcgggccgg gtcgaatccg acctaaaaaa taagcataaa attttgtctt ggatccagcc   4020
caaatctagc ccgacccata atcacctcta gtttaagctt cttcttttct ttctttcttt   4080
ctttctttct ttcttttttt tttttaacat taaaaatatg tagagaaaat cagcaattaa   4140
aacaaaagtt agggctaatg tgttaaagta gcaccaataa agtatccctc tcaagtgaag   4200
tctttcacac ttgcaaacaa aaataattaa aagacagagg agtctataaa gttaaaagcc   4260
gtccaaaacc caaaccagga aaggcaaacg aaaagaaaaa atggctttga attttaatgc   4320
catcgcctcg aaatctcaga agctcccttg ctttgctctt ccaccaaagg ccacccttag   4380
atctcccaag ttttccatga tctccaccat tccttctggc tccaagttag tgtctttctt   4440
tcttttcttt ttggctggcg ttttattcat tattgtaata acttgatcat tctcgcctat   4500
aatcatggat cataaccttt tcttcttctt cttcttcttc ttcttctttt acttaaagct   4560
gattttgaat ctgggttttt gttgttttgt ctaactgaca tggctttcag gacttctctt   4620
ttatgatatc tcacaatctt aacgttcttg ttgtttaatg gcctctaatc attgttatga   4680
tgagatttga acttttacaa attatgatat tgttgtcttt gaatccttgg taataatgat   4740
```

```
gatgtatgag tatgagaatg aaagtaatcc caaagttggt ttatttttac tgaacacaga   4800
gaggttggga atctgaaaaa gcctttcacg cctccaaagg aggtgcctgt tcagatcacc   4860
cactccatgc cgcctcacaa gattgagatc tttaaatctt tggagggctg ggctgagaac   4920
aacattctga ctcacctcaa accagttgag aaatgttggc aacccgccga ctttcttcca   4980
gatcctaatt ctgatggatt tcatgagcaa gtcaaagagc ttagggaaag ggcaaaggag   5040
atcccagatg attactttgt agttttggtt ggtgatatga tcaccgagga agccctttca   5100
acttatcaaa caatgcttaa taccttggat ggaactcgtg atgagacagg tgctagcctt   5160
accccttggg ccatttggac cagggcttgg actgctgaag aaaacaggca tggtgatctg   5220
cttaataagt atctctactt gtctgggaga gtggacatga ggcaaattga gaggacaatc   5280
cagtacttga ttggatcggg aatggtaaga ataacatact tgctacacag tttaggagga   5340
tgattgagtg attgacattt aattactctt ttcaatttct aagaaaggaa aacagacaag   5400
catgcaagat gtcattattt tctttttata cagttccaat ctgtcattgt taaactaaac   5460
tctttcttct gtataacgat aggatcctca tacagagaat agtccttacc gaggattcat   5520
atatacttcg ttccaagaaa gggcaacttt tatttcccat gggaatacag gcaggctggc   5580
taaggagtat ggggatatta acttggctca aatttgtggt agcattgcct cagatgagaa   5640
gcgccacgag acagcctata ccaaaatcgt tgaaaagctg tttgagattg atcctgatga   5700
aacagtcctg gcatttgctg acatgatgaa gaagaaaatc gccatgccgg ctgagttcat   5760
ctatgatggc agagattata acttatttga ccactactca gctgttgccc aaagaatcgg   5820
ggtttacact gctaaggact atgttgatat agtagagcac ctggtggatc gatggaaggt   5880
gaaggagcta gctgggcttt cagccgaggg gcgtaaagct caggactact tgtgttcact   5940
tccttcgaga attagaaggt tagaggagag agcgcaagaa aaggccaagg aagcacccag   6000
tgtcccattc agttggatat ttgatagaga agtgaaactt taggtcatga aatacagtta   6060
agactcctgc aatgcatttg aggaaacaaa cacgaagaag ctgaatgcca acttctcttt   6120
atatatccga tgtaatagag gttgtatatg taacaggagg aattgcgtgg ctttggttag   6180
ggtagcacat gttttctgga tgtgttgtgt ccttaaaaaa taatgccgat agcggcagct   6240
gtgatagttt tagatgtttg ttttcataat gtctgttata tcgttgtacg agtagtatgt   6300
gttgtttttg ttgaaacaat cttcatatct tagtgataaa tgataatgct gtgtagtcat   6360
agtttttagt ttgcaataaa aaattccttc tcgatattgg gttagttttg ttttgaatgg   6420
caaaacctac tttacatacc ttcaacatct agcgttgtca ctgtagaaaa cgcaagtggt   6480
aaatttcaag ctgtagatcg tactttttct tacacgagta acacagttca gctaattaga   6540
g                                                                   6541
```

<210> SEQ ID NO 23
<211> LENGTH: 396
<212> TYPE: PRT
<213> ORGANISM: Gossypium hirsutum

<400> SEQUENCE: 23

```
Met Ala Leu Asn Phe Asn Ala Ile Ala Ser Lys Ser Gln Lys Leu Pro
1               5                   10                  15

Cys Phe Ala Leu Pro Pro Lys Ala Thr Leu Arg Ser Pro Lys Phe Ser
            20                  25                  30

Met Ile Ser Thr Ile Pro Ser Gly Ser Lys Glu Val Gly Asn Leu Lys
        35                  40                  45
```

-continued

```
Lys Pro Phe Thr Pro Pro Lys Glu Val Pro Val Gln Ile Thr His Ser
    50                  55                  60

Met Pro Pro His Lys Ile Glu Ile Phe Lys Ser Leu Glu Gly Trp Ala
65                  70                  75                  80

Glu Asn Asn Ile Leu Thr His Leu Lys Pro Val Glu Lys Cys Trp Gln
                85                  90                  95

Pro Ala Asp Phe Leu Pro Asp Pro Asn Ser Asp Gly Phe His Glu Gln
            100                 105                 110

Val Lys Glu Leu Arg Glu Arg Ala Lys Glu Ile Pro Asp Asp Tyr Phe
        115                 120                 125

Val Val Leu Val Gly Asp Met Ile Thr Glu Glu Ala Leu Ser Thr Tyr
    130                 135                 140

Gln Thr Met Leu Asn Thr Leu Asp Gly Thr Arg Asp Glu Thr Gly Ala
145                 150                 155                 160

Ser Leu Thr Pro Trp Ala Ile Trp Thr Arg Ala Trp Thr Ala Glu Glu
                165                 170                 175

Asn Arg His Gly Asp Leu Leu Asn Lys Tyr Leu Tyr Leu Ser Gly Arg
            180                 185                 190

Val Asp Met Arg Gln Ile Glu Arg Thr Ile Gln Tyr Leu Ile Gly Ser
        195                 200                 205

Gly Met Asp Pro His Thr Glu Asn Ser Pro Tyr Arg Gly Phe Ile Tyr
    210                 215                 220

Thr Ser Phe Gln Glu Arg Ala Thr Phe Ile Ser His Gly Asn Thr Gly
225                 230                 235                 240

Arg Leu Ala Lys Glu Tyr Gly Asp Ile Asn Leu Ala Gln Ile Cys Gly
                245                 250                 255

Ser Ile Ala Ser Asp Glu Lys Arg His Glu Thr Ala Tyr Thr Lys Ile
            260                 265                 270

Val Glu Lys Leu Phe Glu Ile Asp Pro Asp Glu Thr Val Leu Ala Phe
        275                 280                 285

Ala Asp Met Met Lys Lys Lys Ile Ala Met Pro Ala Glu Phe Ile Tyr
    290                 295                 300

Asp Gly Arg Asp Tyr Asn Leu Phe Asp His Tyr Ser Ala Val Ala Gln
305                 310                 315                 320

Arg Ile Gly Val Tyr Thr Ala Lys Asp Tyr Val Asp Ile Val Glu His
                325                 330                 335

Leu Val Asp Arg Trp Lys Val Lys Glu Leu Ala Gly Leu Ser Ala Glu
            340                 345                 350

Gly Arg Lys Ala Gln Asp Tyr Leu Cys Ser Leu Pro Ser Arg Ile Arg
        355                 360                 365

Arg Leu Glu Glu Arg Ala Gln Glu Lys Ala Lys Glu Ala Pro Ser Val
    370                 375                 380

Pro Phe Ser Trp Ile Phe Asp Arg Glu Val Lys Leu
385                 390                 395
```

VEGETABLE OILS AND USES THEREFOR

This application is a continuation-in-part of PCT International Application No. PCT/AU2009/000930, filed Jul. 21, 2009, and claims the benefit of U.S. Provisional Application No. 61/135,621, filed Jul. 21, 2008, the contents of all of which are hereby incorporated by reference into this application.

This application incorporates-by-reference nucleotide and/or amino acid sequences which are present in the file named "110121_0687_79599_B_SequenceListing_DES.txt," which is 73 kilobytes in size, and which was created Jan. 21, 2011 in the IBM-PC machine format, having an operating system compatibility with MS-Windows, which is contained in the text file filed Jan. 21, 2011 as part of this application.

FIELD

The present specification relates to the production of plants comprising oil having modified fatty acid compositions. The specification describes such vegetable oils having inter alia increased levels of palmitic and stearic acid.

BACKGROUND

The major components of vegetable oils used in the food industry are the saturated fatty acids, palmitic acid (C16:0) and stearic acid (C18:0), the monounsaturated fatty acid, oleic acid (C18:1) and the polyunsaturated fatty acids, linoleic acid (C18:2) and α-linolenic acid (C18:3). These fatty acids are present in the oils mostly in form of triacylglycerols, in which three fatty acids are esterified to a glycerol molecule. Small amounts of diacyglycerols, monoacylglycerols, phospholipids and free fatty acids may also be present in vegetable oils, along with components such as sterols etc.

The number, position, and conformation of carbon-carbon double bonds in the fatty acid present in the triacylglycerols of the oil influences its physical properties such as melting temperature and other chemical properties as well as its nutritional value, and the applications to which it may be put, particularly in the food industry. For example, the presence of a carbon double bond in a monounsaturated fatty acid or polyunsaturated fatty acid lowers its melting temperature, compared to the melting temperature of a saturated fatty acid of the same carbon chain length, such that the C-18 unsaturated fatty acids, oleic acid, linoleic acid, and linolenic acid, are all liquid at ambient temperature.

Additionally, the susceptibility of a fatty acid to oxidation increases proportionately with the number of carbon double bonds present in the fatty acid molecule, greatly reducing the suitability of oils containing polyunsaturated fatty acids to applications involving the use of prolonged heat in the presence of oxygen, such as cooking and other food service applications, or in non-food applications such as use in the production of cosmetics, pharmaceuticals and candles. For applications that require solid fat components such as in solid cooking fats, shortenings, or margarines, it is necessary to have moderately high levels of saturated fatty acids, or the functionally equivalent trans-fatty acids. Trans-fatty acids have carbon double bonds in the trans-orientation rather than the naturally-occurring cis-orientation.

Currently, many oils high in unsaturated fatty acids are subjected to chemical hydrogenation, to improve their suitability in cooking and food service applications. However, undesirable trans-fatty acids may be produced in this process.

The nutritional quality of vegetable oils depends on the content of both saturated fatty acids and trans fatty acids (Wollett and Dietshy, *Amer. J. Clin. Nutr.* 60: 991-96, 1994). The contribution of high levels of some saturated fatty acids in the diet, particularly palmitic acid, to increased blood cholesterol, and more particularly to increased low density lipoprotein (LDL), is well-established. Elevated LDL in the blood has been associated with an enhanced risk of cardiovascular disease in humans. Moreover, trans-fatty acids also elevate LDL cholesterol in a manner similar to palmitic acid. However, not all saturated fatty acids are associated with elevated cholesterol. For example, stearic acid is reported to have neutral effects on blood cholesterol (Wollett and Dietshy, 1994 (supra)). In this respect, the high melting temperature of stearic acid (approximately 70° C.) also makes it particularly suitable in solid fat applications. Accordingly, because of its neutral effects on blood cholesterol levels, a high stearic acid-containing oil is a desirable substitute for partially-hydrogenated plant oils currently used in margarine production.

The oil obtained from seeds of the *Theobroma cacao* plant has an unusual composition that provides several highly desirable properties in the food, particularly confectionary, industries such as chocolate manufacture. The oil typically has about 40% or more stearic acid as well as about 36% oleic acid. More than 50% of the TAG in the oil is oleo-distearin, having one oleic acid molecule and two stearic acid molecules esterified in the TAG. The oil has high levels of palmitic acid in addition to stearic and oleic acids, often esterified on symmetrical triacylglycerols such as sn-1,3 distearoyl sn-2 oleoyl acyl glycerol (SOS), sn-1 palmitoyl sn-2 oleoyl sn-3 stearoyl acyl glycerol (POS), and sn-1,3 dipalmitoyl sn-2 oleoyl acyl glycerol (POP). This composition provides a sharp melting point at about 35° C., with softening at 30-32° C. At only slightly lower temperatures, below about 20° C., the oil is a solid with brittle fracture properties. The oil, also known as "cocoa butter" is in demand and has a high value.

The unreliability and price fluctuation of cocoa butter supply has made the confectionary industry search for a more reliable source of alternative plant fat which can be used as a substitute for cocoa butter. The most common cocoa butter equivalents to date have been made by interesterification of palm oil, palm mid-fraction and oils derived from some tropical oil-bearing plants, such as illipe (*Shorea stenoptera*), Shea (*Butyrospermum parrkii*), sal (*Shorea robusta*) and kokum (*Garcinia indica*) which contain high level of stearic acid, but insufficient level of palmitic acid. These tropical seed lipids are currently used as the stearic acid donor. The major TAG in the mid-fraction from palm oil is POP and its interesterification with these high-stearic tropical oils using a 1,3-specific lipase can produce TAG's that resemble the fatty acid composition and TAG structures of cocoa butter (Mojovic et al., *Enzyme Microb Technol.* 15: 438-443, 1993). As these tropical fats are generally expensive, the industry has also been producing cocoa butter substitute through hydrogenation and fractionation of common vegetable oils, including cottonseed oil. In this approach, the undesirable health effect of trans fatty acids resulted from the hydrogenation process are a serious impediment for the industry.

Isolated and purified vegetable oils such as cottonseed oil are composed mostly (>95%) of triacylglycerols (TAGs) that are synthesized and deposited during seed development. TAG molecules consist of three fatty acids esterified to a glycerol backbone at the sn-1, sn-2 and sn-3 positions. Briefly, the de novo biosynthesis of fatty acids in cotton seed, as in other oilseeds, occurs in the stroma of plastids during development and growth of the seeds, ie. before maturation. Fatty acids are then exported from the plastids in the form of acyl-CoA thioesters to the cytoplasmic endomembrane systems (endoplasmic reticulum, ER) where modification of fatty acids occurs after transfer of the acyl groups from the CoA thioesters to phospholipids by acyltransferases. This is followed by TAG assembly and storage in the oleosomes.

The biotin-containing enzyme acetyl-CoA carboxylase (ACCase) catalyses the first committed step in the pathway by activating acetyl-CoA to the three carbon intermediate, malonyl-CoA, by addition of a carboxyl group. The malonyl group is then transferred from CoA to an acyl-carrier protein (ACP), which serves as the carrier for the growing fatty acid chain. Malonyl-ACP is reacted with a second acetyl-CoA condensing enzyme, ketoacyl-ACP synthase III (KASIII), resulting in a four carbon chain. The repeated process of adding two-carbon units on the elongated fatty acid chain is catalyzed by KASI leading to the formation of palmitoyl-ACP. KASII catalyzes the elongation of palmitoyl-ACP to stearoyl-ACP. A soluble stearoyl-ACP Δ9-desaturase introduces the first double bond into stearoyl-ACP to convert it to oleoyl-ACP in the plastid. The extended, saturated fatty acyl chain and the monounsaturated oleate are cleaved off the ACP by a specific thioesterase enzyme, FatB or FatA, respectively, enabling them to exit the plastid and enter the cytoplasm. Saturated fatty acids released into the cytoplasm are not further modified. However, oleic acid can be further modified on the endoplasmic reticulum (ER) membranes by the action of membrane-bound desaturases. Phosphatidylcholine (PC)-bound acyl chains serve as a substrate for ER localized, lipid modifying enzymes, such as fatty acid desaturase 2 (FAD2) which introduces a double bond into oleic acid on the sn-2 position of PC to produce linoleic acid. All the modified and unmodified fatty acyl groups then form a pool while attached to CoA. In cotton, but not in other temperate zone oilseeds, oleic acid may be used as substrate for cyclopropanation catalysed by cyclopropane fatty acid synthase to produce dihydrosterculic acid. This fatty acid is subsequently desaturated to produce sterculic acid and then α-oxidased to produce malvalic acids. Finally fatty acyl groups are incorporated into storage lipids via the Kennedy pathway by the sequential esterification of glycerol-3-phosphate by the action of a series of TAG assembly enzymes.

The enzyme ketoacyl-ACP synthase II (KASII) (EC 2.3.1.41) catalyzes the elongation of palmitoyl-ACP to stearoyl-ACP. The ketoacyl-ACP synthases are often referred to as condensing enzymes of the KAS family. KASI, II and III differ in their chain length specificities, KASI elongates C4:0 to C16:0, while KASII elongates C16:0 to C18:0 (FIG. 1).

Cottonseed oil, which is widely used as a vegetable oil for food applications, produced by conventional (wild-type) upland cotton (*G. hirsutum*) typically contains approximately 26% palmitic acid (range 22-28%), 1-2% stearic acid, 15% oleic acid (range 13-18%) and 58% linoleic acid (range 52-60%) (Cherry, *J. Am. Oil Chem. Soc.* 60: 360-367, 1983; O'Brien, Cottonseed Oil. In: F. D. Gunstone (Ed.) Vegetable Oils in Food Technology Composition, Properties and Uses. Blackwell Publishing, Oxford, pp. 203-230, 2002). Unhydrogenated cottonseed oil also contains low levels (0.5-1%) of cyclopropane (CPA) or cyclopropene (CPE) fatty acids, mainly malvalic (MVL), sterculic (STC) and dihydrosterculic acids (DHS) (Shenstone and Vickery, *Nature* 190: 68-169, 1961; Cherry, 1983 (supra)) These fatty acids accumulate almost exclusively in the embryonic axes of cottonseed. CPA and CPE are not found at detectable levels in major oilseed crops other than cotton, including in palm oil, soybean, corn, canola, mustard, sunflower, safflower, peanut, linseed, other *Brassicas* etc.

The first committed step to produce these uncommon fatty acids is catalysed by a cyclopropane fatty acid synthase (CPA-FAS) which adds a methylene group across the double bond of oleic acid to produce DHS (FIG. 2). In cotton, most of the DHS is desaturated by the enzyme CPA desaturase to produce STC, most of which is further modified by α-oxidation to form MVL (FIG. 2). MVL is the predominant cyclopropenoid fatty acid in wild-type cottonseed oil.

The relatively high level of saturated fatty acids, mainly palmitic acid, in cottonseed oil compared to oils from most other temperate zone oilseed crops contributes to the oxidative stability of cottonseed oil by offsetting the greater instability of the other, unsaturated fatty acid components. It also imparts the high melting point required for making such products as margarine and shortening. Except for palm oil, cottonseed contains the highest palmitic acid level (26%) among the major commodity vegetable oils. Cottonseed oil also contains a high level of linoleic acid which is oxidatively unstable and therefore limits the shelf life of the oil and makes it unsuitable for some food applications.

Conventional cottonseed oil is therefore often processed by partial hydrogenation during which the polyunsaturated linoleic acid is transformed into more stable monounsaturated (oleic) and saturated (stearic) fatty acids. Partial hydrogenation results in a number of structural changes to a fraction of the fatty acids, including the shifting of a double bond. This may lead to the production of trans fatty acids (TFA) which are isomers of the naturally occurring unsaturated fatty acids, such as elaidic acid which is the trans-isomer of oleic acid. Oleic and elaidic acids contain the same number of atoms (C18:1), with a double bond in the same location, but it is the conformation of the double bond that sets them apart. TAG containing elaidic acid, with the trans double bond configuration, has a much higher melting point than oleic acid. Partial hydrogenation also converts cyclopropanoic or cyclopropenoic fatty acids to branched chain fatty acids by opening up the cyclopropane ring, producing a branched fatty acid with a additional methyl group attached to C9 or C10 of the fatty acid carbon chain.

Compared with polyunsaturated fatty acids, oleic acid is more stable towards oxidation both at ambient storage temperatures and at the high temperatures used in cooking and frying of food. Studies with a number of vegetable oils such as safflower and soybean oils indicate that high-oleic vegetable oils are slower to develop rancidity during storage, or to oxidatively decompose during frying or other use, compared to oils that contain high amounts of polyunsaturated fatty acids (Fuller et al., *J. Food Sci.* 31: 477-480, 1966; Mounts et al., *J. Am. Oil Chem. Soc.* 65: 624-628, 1998).

It is known that malvalic and sterculic acids are potent inhibitors of animal Δ9-stearoyl-CoA desaturase. Although the CPA and CPE fatty acids are not stable and are mostly eliminated during oil processing, particularly by hydrogenation, the residual oil in the meal and the whole cottonseed used in the feed industry could exert negative effects on animal health. Feeding farmed animals with excess amounts of cottonseed is thought to possibly cause a number of health problems for animals and may affect the quality of animal products, such as the hardening of fats in egg yolk and milk (Johnson et al., *Nature* 214: 1244-1245, 1967; Roehm et al., *Lipids* 5: 80-84, 1970). Methods have been developed to inactivate cyclopropenoid fatty acids through specialised partial hydrogenation processes. Merker and Mattil, 1965 reported a hydrogenation process in which malvalic and sterculic acids were selectively reduced to their dihydro or tetrahydro derivatives, by means of a nickel catalyst, without significant reduction of the linoleic acid or trans acid formation. Hutchins et al., *Journal of American Oil Chemists Society* 45: 397-399, 1968 showed selective hydrogenation of the cyclopropenoid groups in cottonseed oil by means of a packed-bed reactor and nickel catalysts under milder conditions. However, these hydrogenation processes add additional costs for processing of the oil and are not desirable.

In the 1970's, the cotton breeding program of the Acala SJ series in California (Cherry, 1983 (supra)) reduced palmitic acid from 23.3 to 22.7%, increased oleic acid from 16.6% to 17.3% and reduced total cyclic fatty acids from 0.9% to 0.8% in cottonseed oil. However, compared to achievements in other oilseed crops, these changes were only minor, reflecting the narrow genetic base of elite cotton varieties as a result of persistent selection on traits other than oil quality.

Four different cDNAs encoding FAD2 were isolated from cotton (Liu et al., *Australian Journal of Plant Physiology* 26: 101-106, 1999a; Liu et al., *Plant Physiol.* 120: 339, 1999b; Pirtle et al., *Biochim. Biophys. Acta* 1522: 122-129, 2001, all herein incorporated by reference), among which ghFAD2-1 was determined to play a major role in the production of linoleic acid in cottonseed oil. Analysis of gene expression suggested that the ghFAD2-1 gene was specifically expressed in developing seeds, with maximal expression during the middle maturity stage of seed development (Liu et al., 1999a (supra)).

U.S. Pat. No. 6,974,898 (herein incorporated by reference) describes the generation of cottonseed oil containing up to 77% oleic acid by downregulation of microsomal Δ12 desaturase (FAD2) by RNAi methods. Palmitic acid levels in the oils were reduced.

Furthermore, novel oils having approximately equal proportions of palmitic, stearic and oleic would have considerable potential for use as a cocoa butter substitute.

There is therefore a need to increase the levels of palmitic and stearic acid levels in vegetable oils for particular uses.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. Each embodiment is to be applied mutatis mutandis to every other embodiment unless expressly stated otherwise.

As used herein the singular forms "a", "an" and "the" include plural aspects unless the context clearly dictates otherwise. Thus, for example, reference to "a mutation" includes a single mutation, as well as two or more mutations; reference to "an agent" includes one agent, as well as two or more agents; and so forth.

Bibliographic details of the publications referred to by author in this specification are collected at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The term "derived from" indicates that the specified integer is obtained from a specific source although not necessarily directly from that source.

The designation of exemplary amino acid sequences is set out in Table 7 after the Examples.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of sequence identifiers is provided in Table 6 after the Examples. A sequence listing is provided after the claims.

Genes and other genetic material (eg RNA, nucleic acid constructs etc) are represented herein in italics while their proteinaceous expression products are represented in non-italicised form.

Representative examples of the nucleic acid and amino acid sequences of the present invention are provided in the sequence listing and are further described in Table 6 and in the Examples.

In one embodiment, the present invention provides a method of producing modified seedoil, comprising the steps of: (i) obtaining seed from a plant; (ii) extracting the oil from the seed; and (iii) recovering the seedoil, wherein the seedoil has a modified fatty acid composition such that 28% to 80% of the total fatty acid content in the seedoil is palmitic acid, 0% to 16% is palmitoleic acid, 0% to 4% is C16:2 fatty acid, 3% to 33% is stearic acid, 1% to 40% is oleic acid, 4% to 50% is linoleic acid and 0% to 10% is linolenic acid.

In another embodiment of the method the seedoil has a composition characterized by any one, two, three, four, five or all six of the group consisting of: i) 28% to 50%, preferably 28% to 45%, more preferably 28% to 40%, of the total fatty acid content in the seedoil is palmitic acid; ii) 0% to 8%, preferably 1% to 6%, of the total fatty acid content in the seedoil is palmitoleic acid; iii) 0% to 2% of the total fatty acid content in the seedoil is C16:2 fatty acid; iv) 4% to 33%, preferably 4% to 31%, more preferably 4% to 29% of the total fatty acid content in the seedoil is stearic acid; v) 4% to 11%, preferably 5% to 11%, of the total fatty acid content in the seedoil is linoleic acid; and vi) 0% to 8%, preferably 0% to 6%, more preferably 0% to 4% or 0% to 3%, of the total fatty acid content in the seedoil is linolenic acid. It would be appreciated that each and every possible combination of these six elements is included in this aspect of the invention.

In another embodiment, 0.1% to 1%, preferably 0.1% to 0.5%, of the total fatty acid content in the seedoil is cyclopropane fatty acid or cyclopropene fatty acid or a combination of these. In some embodiments, the cyclopropane or cyclopropene fatty acid is malvalic acid, sterculic acid, dihydrosterculic acid or any combination of two of these or all three of these.

In some embodiments, 0.1% to 1% of the total fatty acid content in the seedoil is a branched fatty acid which is a fatty acid with a C18 chain with a methyl group attached to C9 or C10. In other embodiments less than 0.5%, preferably less than 0.1%, of the total fatty acid content is a branched fatty acid at C9 or C10. In some embodiments, less than 0.5%, preferably less than 0.1%, of the total fatty acid content is a trans fatty acid. In some embodiments, the trans fatty acid is elaidic acid. In other embodiments, less than 0.5%, preferably less than 0.1%, of the oil is cholesterol. In further embodiments, at least 95% of the fatty acid is esterified in the form of triacylglycerols. In another embodiment, the oil comprises sterols, preferably β-sitosterol, stigmasterol and/or campesterol. The level of the sterols, in total, may be 0.5% to 2.5% by weight of the oil.

In some embodiments of the method, step (i) further comprises harvesting the seed from a plant. In other embodiments, step (ii) comprises crushing the seed. In other embodiments, step (iii) comprises purifying the seedoil.

The present invention has been illustrated using cotton plants, cottonseeds and cotton seed oil. However the invention extends to other angiosperms, their seeds and their seedoils such as, without limitation, cotton seed oil, palm oil, soybean oil, corn oil, mustard seed oil, sunflower seed oil, safflower oil, peanut oil, linseed and other *Brassicas* oil. In a particular embodiment, the seedoil is cottonseed oil.

In another embodiment, the invention provides a seedoil having a modified fatty acid composition, wherein the seedoil has a fatty acid composition such that 28% to 80% of the total fatty acid content in the seedoil is palmitic acid, 0% to 16% is palmitoleic acid, 0% to 4% is C16:2 fatty acid, 3% to 33% is stearic acid, 1% to 40% is oleic acid, 4% to 50% is linoleic acid and 0% to 10% is linolenic acid.

In some embodiments, seedoil has a composition characterized by any one, two, three, four, five or all six of the group consisting of: i) 28% to 50% of the total fatty acid content in the seedoil is palmitic acid; ii) 0% to 8% of the total fatty acid content in the seedoil is palmitoleic acid; iii) 0% to 2% of the total fatty acid content in the seedoil is C16:2 fatty acid; iv) 4% to 33% of the total fatty acid content in the seedoil is stearic acid; v) 4% to 11% of the total fatty acid content in the seedoil is linoleic acid; and vi) 0% to 8% of the total fatty acid content in the seedoil is linolenic acid. In preferred embodiments, the seedoil has a composition as described in paragraph 0033.

In another embodiment, 0.1% to 1% of the total fatty acid content in the seedoil is cyclopropane fatty acid or cyclopropene fatty acid or a combination of these. In some embodiments, the cyclopropane or cyclopropene fatty acid is malvalic acid, sterculic acid, dihydrosterculic acid or any combination of two of these or all three of these. In other embodiments, 0.1% to 1% of the total fatty acid content in the seedoil is a branched fatty acid which is a fatty acid with a C18 chain with a methyl group attached to C9 or C10. In other embodiments, less than 0.5%, preferably less than 0.1%, of the total fatty acid content is a branched fatty acid at C9 or C10. In other embodiments, less than 0.5%, preferably less than 0.1%, of the total fatty acid content is a trans fatty acid. In some embodiments, the trans fatty acid is elaidic acid. In other embodiments, less than 0.5%, preferably less than 0.1%, of the oil is cholesterol. In further embodiments, at least 95% of the fatty acid is esterified in the form of triacylglycerols. In another embodiment, the oil comprises sterols, preferably β-sitosterol, stigmasterol and/or campesterol. The level of the sterols, in total, may be 0.5% to 2.5% by weight of the oil.

In another embodiment, the specification describes a seed having a modified fatty acid composition in its seedoil, wherein the seedoil has a fatty acid composition such that 28% to 80% of the total fatty acid content in the seedoil is palmitic acid, 0% to 16% is palmitoleic acid, 0% to 4% is C16:2 fatty acid, 3% to 33% is stearic acid, 1% to 40% is oleic acid, 4% to 50% is linoleic acid and 0% to 10% is linolenic acid.

In some embodiments, the seedoil has a composition characterized by any one, two, three, four, five or all six of the group consisting of: i) 28% to 50% of the total fatty acid content in the seedoil is palmitic acid; ii) 0% to 8% of the total fatty acid content in the seedoil is palmitoleic acid; iii) 0% to 2% of the total fatty acid content in the seedoil is C16:2 fatty acid; iv) 4% to 33% of the total fatty acid content in the seedoil is stearic acid; v) 4% to 11% of the total fatty acid content in the seedoil is linoleic acid; and vi) 0% to 8% of the total fatty acid content in the seedoil is linolenic acid. In preferred embodiments, the seedoil has a composition as described in paragraph 0033.

In another embodiment, the seed as described herein is transgenic for a genetic construct which encodes an RNA molecule which inhibits expression of a gene encoding KASII.

In some embodiments, the RNA comprises a contiguous sequence of nucleotides encoding a sequence having at least 65%, preferably at least 70%, identity to the sequence set forth in SEQ ID NO: 1 or that hybridizes thereto under conditions of moderate stringency, or comprises a contiguous sequence of nucleotides which encodes the amino acid set forth in SEQ ID NO: 2 or a sequence having at least 65%, preferably at least 70%, identity thereto.

In some examples, the seed is a monocotyledonous seed. However, in other embodiments of this invention the seed is a dicotyledonous seed. In an illustrative example, the species of plant is *Gossypium hirsutum* or *Gossypium barbadense.*

As described herein, in some embodiments, the seed further has a reduced level of gossypol, wherein the level of gossypol in the seed is reduced by at least 10% relative to the level of gossypol in cottonseed of cotton variety Coker.

In some embodiments, the seed is other than *Arabidopsis thaliana.*

In another embodiment, the present specification provides methods of producing the herein disclosed seeds, comprising harvesting seed from a plant and optionally ginning the harvested product, thereby producing the seed.

In another embodiment, the specification describes a method of producing a plant with modified fatty acid composition in its seedoil, comprising sowing the herein disclosed seeds and allowing the seed to grow into the plant.

In another embodiment, the specification provides a plant which is capable of producing the herein disclosed seeds.

In another embodiment, the specification provides cotton lint obtained from the subject cotton plant.

In yet another embodiment, the specification provides a method of identifying seed which has a modified fatty acid composition in its seedoil, comprising: (i) obtaining transgenic seed; (ii) determining the fatty acid composition of the oil of the seed; and (iii) if the fatty acid composition is such that 28% to 80% of the total fatty acid content in the seedoil is palmitic acid, 0% to 16% is palmitoleic acid, 0% to 4% is C16:2 fatty acid, 3% to 33% is stearic acid, 1% to 40% is oleic acid, 4% to 50% is linoleic acid and 0% to 10% is linolenic acid, selecting the seed.

In some embodiments, the seedoil has a composition characterized by any one, two, three, four, five or all six of the group consisting of: i) 28% to 50% of the total fatty acid content in the seedoil is palmitic acid; ii) 0% to 8% of the total fatty acid content in the seedoil is palmitoleic acid; iii) 0% to 2% of the total fatty acid content in the seedoil is C16:2 fatty acid; iv) 4% to 33% of the total fatty acid content in the seedoil is stearic acid; v) 4% to 11% of the total fatty acid content in the seedoil is linoleic acid; and vi) 0% to 8% of the total fatty acid content in the seedoil is linolenic acid. In preferred embodiments, the seedoil has a composition as described in paragraph 0033.

In some embodiments, the method further comprises preparation of a genetic construct suitable for expression in the seed during seed development, transformation of a plant cell with the genetic construct and regeneration of a transgenic plant prior to step (i). In some embodiments, step (i) comprises the obtaining of multiple independent transgenic seeds each of which contains a genetic construct which is the same in each transgenic seed, wherein the fatty acid composition of the seedoil of each of the multiple independent transgenic seeds is determined.

In still another embodiment, the present invention provides a nucleic acid molecule encoding an RNA molecule which is capable of inhibiting expression of a gene encoding KASII in developing seed of a plant.

In some embodiments, the RNA comprises a contiguous sequence of nucleotides encoding a sequence having at least 65% identity, preferably at least 70% identity, to the sequence set forth in SEQ ID NO: 1 or its complement, or that hybridizes thereto under conditions of moderate stringency, or comprises a contiguous sequence of nucleotides which encodes the amino acid set forth in SEQ ID NO: 2 or a sequence having 65% identity, preferably at least 70% identity thereto, or a functional fragment or variant of either of these.

In some embodiments, the nucleic acid molecule comprises an inverted repeat of nucleotides encoding all or part of the coding region of KASII-A gene set forth in SEQ ID NO: 1. In other embodiments, the inverted repeat comprises the sequence set forth in SEQ ID NO: 5 or a functional fragment or variant comprising a sequence having 95% identity thereto.

In some embodiments, the nucleic acid further encodes one or more RNA molecules which together are capable of inhibiting expression of a gene/s encoding polypeptide/s selected from one, two or three of the following: (i) FAD-2; (ii) SAD-1; (iii) CPA-FAS-2; (iv) SAD-1 and FAD-2; (v) SAD-1 and FAD-2 and CPA; and (vi) SAD-1 and FAD-2 and FATB in developing seed of a plant.

In other embodiments, the nucleic acid encodes one or more RNA molecules which together are capable of inhibiting expression of genes encoding KASII, FAD2 and SAD-1 in developing seed of a plant.

In some embodiments, the plant is cotton and the genes are ghFAB-1 (KASII), ghFAD2-1, ghSAD-1 and optionally further includes ghCPA-FAS-2.

In other embodiments, the RNA molecule is ghFAB-1, ghFAD2-1, ghSAD-1 and optionally further includes ghCPA-FAS-2.

In relation to this aspect, in some embodiments, the RNA molecule comprises 27 contiguous nucleotides which are identical in sequence to 27 contiguous nucleotides of the transcribed sequence, or its complement, of one of the genes. In other embodiments, at least one of the RNA molecules is a microRNA which comprises 21 contiguous nucleotides which are identical in sequence to 21 contiguous nucleotides of the complement of the transcribed sequence of one of the genes.

The present invention provides a genetic construct comprising the herein described nucleic acid molecules, and cells and plants comprising same.

In a particular embodiment, the present specification provides for the use of the nucleic acid molecule to reduce expression of FAB-1, FAD2, and SAD-1 genes in developing seed of a plant, and optionally further to reduce expression of CPA-FAS-2 gene in developing seed of a plant.

The above summary is not and should not be seen in any way as an exhaustive recitation of all embodiments of the present invention.

In a further embodiment the invention provides a process for producing seed oil, comprising the steps of:

(i) obtaining cotton seed, safflower seed or *Brassicas* seed, wherein in the oil of the seed about 28% to about 80% by weight of the total fatty acid content is palmitic acid, 0% to about 16% is palmitoleic acid, 0% to about 4% is C16:2 fatty acid, about 3% to about 33% is stearic acid, about 1% to about 40% is oleic acid, about 4% to about 50% is linoleic acid, and 0% to about 10% is linolenic acid;

(ii) extracting the oil from the seed; and (iii) recovering the seed oil.

Thus, in the process of the invention 0% to about 16% of the total fatty acid content may be palmitoleic acid; 0% to about 4% of the total fatty acid content may be C16:2 fatty acid; and/or about 30% to about 80% of the total fatty acid content may be C16 fatty acid.

Further, in the process of invention at least 95% of the total fatty acid content in the seed oil may be in the form of triacylglycerols; the cotton seed, safflower seed or *Brassicas* seed may have a reduced level of FAB-1 protein; step (ii) may comprises crushing the seed; and/or step (iii) may comprise purifying the seed oil.

In yet a further embodiment of the invention cotton seed, safflower seed or *Brassicas* seed is provided, wherein in such seed the seed oil contains about 28% to about 80% of the total fatty acid content as C16 fatty acid, about 3% to about 33% as stearic acid, about 1% to about 40% as oleic acid, about 4% to about 50% as linoleic acid, and 0% to about 10% as linolenic acid.

Thus, seeds of the invention may contain 0% to about 16% of the total fatty acid content of the seed as palmitoleic acid; 0% to about 4% of the total fatty acid content as C16:2 fatty acid; and/or about 30% to about 80% of the total fatty acid content as C16 fatty acid.

Further, the seed of the invention may contain at least 95% of the total fatty acid content in the oil of the seed in the form of triacylglycerols; and/or the seed may have a reduced level of FAB-1 protein.

In yet another embodiment the invention provides a seed oil selected from the group consisting of cotton seed oil, safflower seed oil or *Brassicas* seed oil, wherein in the seed oil about 28% to about 80% of total fatty acid content is C16 fatty acid, about 3% to about 33% is stearic acid, about 1% to about 40% is oleic acid, about 4% to about 50% is linoleic acid and 0% to about 10% is linolenic acid. Thus, the seed oil of the invention may contain 0% to about 16% of the total fatty acid content as palmitoleic acid; 0% to about 4% of the total fatty acid content as C16:2 fatty acid; and/or about 30% to about 80% of the total fatty acid content as C16 fatty acid. In addition, the seed oil of the invention may contain about 0.1% to about 1% of the total fatty acid content as a branched fatty acid with a C18 chain with a methyl group attached at position C9 or C10; or less than 0.5%, of the total fatty acid content is a fatty acid with a C18 chain branched at position C9 or C10.

In respect to the invention a "C16 fatty acid" includes a fatty acid which has 16 carbons in its acyl chain. Illustrative C16 fatty acids include C16:0, C16:1, C16:2 and C16:1+5, the last of which is described, for example, in PCT International Publication No. WO 2008/025068 (Example 8), the disclosure of which is hereby incorporated by reference in its entirety.

BRIEF DESCRIPTION OF THE DRAWINGS

FIG. 3 is a representation of the cDNA sequence from ghKASII-A and its predicted encoded amino acid sequence.

FIG. 4 is a representation of the cDNA sequence from ghKASII-B and its predicted encoded amino acid sequence.

FIG. 6 is a representation of the DNA sequence of the inverted repeat of a 400-bp region of ghKASII-A and its intervening spacer. The repeated DNA sequences are underlined. The NcoI site where the repeated sequence was inserted is in bold.

DETAILED DESCRIPTION

Definitions

The term "oil" as used herein in relation to plants refers to the water insoluble fraction of the plant or seed that comprises mainly fatty acids in the form of triacylglycerols (TAGs). Oils are often characterized as being liquid at room, body or ambient temperature however this quality is a function at least in part of the number, position and conformation of carbon-carbon double bonds in the fatty acid molecules. In accordance with the present invention the term "oil" includes compositions comprising fatty acids and/or TAGs that are solid at room, body or ambient temperature.

Figure 1:
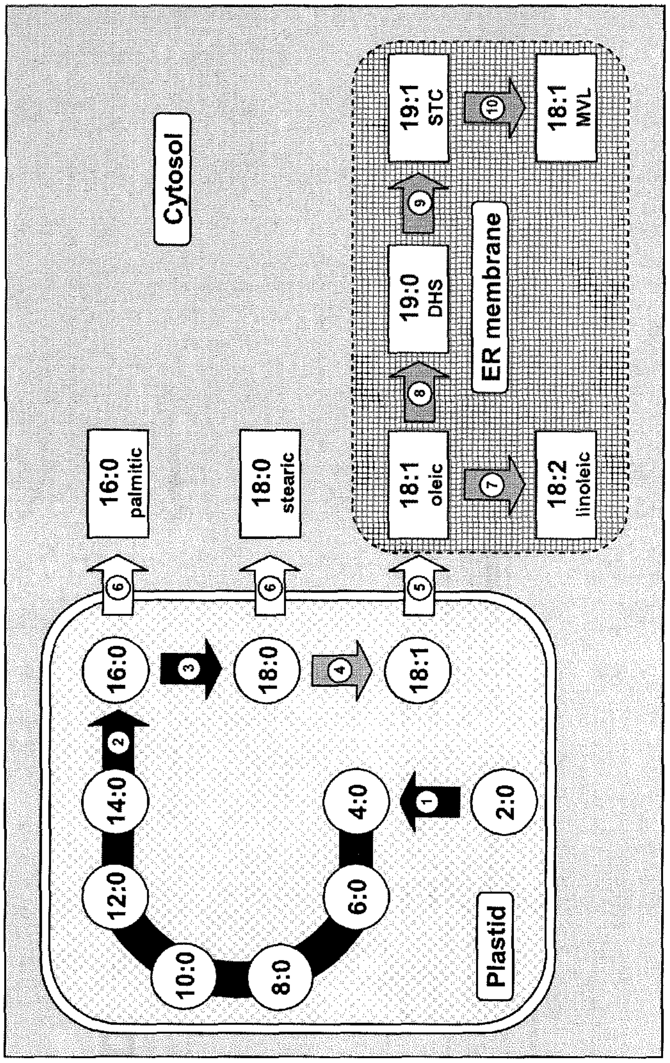
FIG. 1 is a schematic diagram of fatty acid biosynthesis in developing cottonseed showing important enzymatic steps: 1. keto-acyl synthase III (KASIII), 2. keto-acyl synthase I (KASI), 3. keto-acyl synthase II (KASII), 4. Δ9-stearoyl-ACP desaturase (SAD), 5. oleoyl-ACP thioesterase, 6. acyl-ACP thioesterase, 7. Δ12-oleoyl-lipid desaturase (FAD2), 8. cyclopropane fatty acid synthase (CPA-FAS), 9. cyclopropane fatty acid desaturase (CPA-FAD), 10. α-oxidase. DHS: dihydrosterculic acid; STC, sterculic acid; MVL, malvalic acid.
Figure 2:
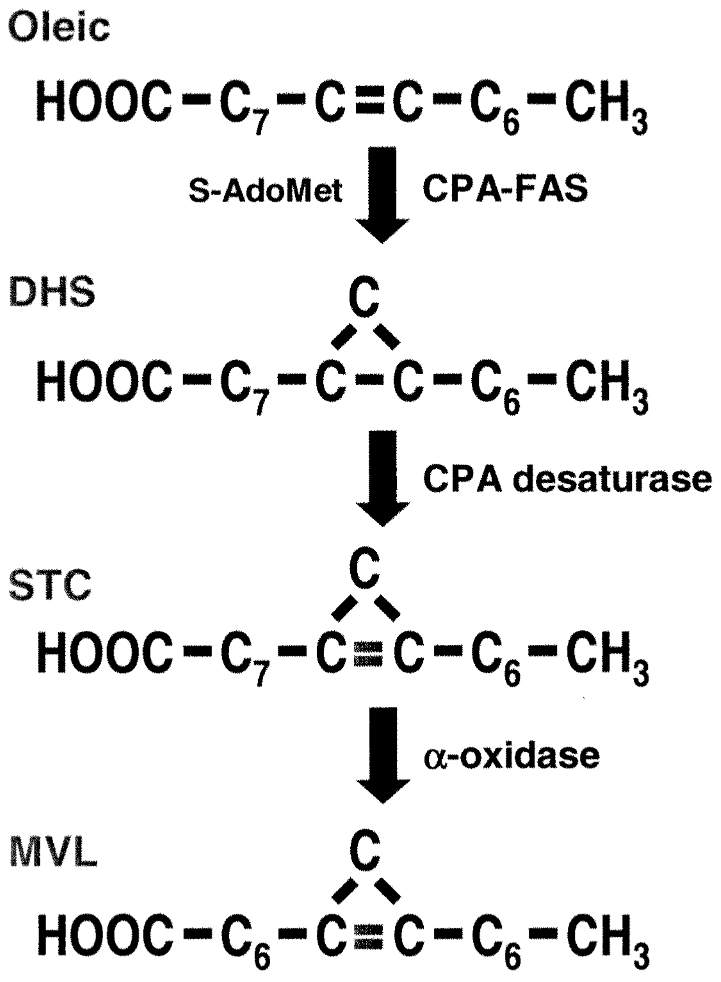
FIG. 2 is a schematic representation of biosynthesis of cyclopropane (CPA) and cyclopropene (CPE) fatty acids in developing cottonseed. Oleic acid is the fatty acid substrate for cyclopropane fatty acid synthase (CPA-FAS). S-adenosyl-L-methionine is the methylene donor and the cyclopropanation of oleic acid is catalysed by CPA-FAS, producing dihydrosterculic acid (DHS). DHS can be further modified by desaturation by the enzyme CPA desaturase to produce sterculic acid (STC). Subsequently, malvalic acid (MVL) is produced by α-oxidation of STC catalysed by an oxidase.

Of particular interest in the present invention is the plant enzyme, ketoacyl-ACP synthase (KASII or FAB-1) (EC2.3.1.41) that catalyses the elongation of palmetoyl-ACP (C16:0) to stearoyl-ACP (C18:0) (step 3 in FIG. 1). The activity of KASII or FAB-1 polypeptides may be determined by assessing the conversion of, or the ratio of, C16:0 to C18:0 in a sample.

Seedoil as used herein means oil obtained from seed of a plant, preferably an oilseed plant, wherein at least 90% of the fatty acid in the seedoil is esterified in the form of TAG. It may be obtained by extraction of the oil from the seed, for example by crushing the seed and, optionally, solvent extraction to isolate more of the oil and/or to purify the oil. It may or may not have been degummed, decolourized, deodorized, its pH adjusted, hydrolysed, or any other procedures well known in the art have been carried out, but it has not been fractionated or hydrogenated to substantially change the fatty acid composition, Genes The present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A "gene encoding KASII", "FAB-1 gene" or the like as used herein refers to a nucleotide sequence encoding KASII in a seed-bearing plant, which is expressed in developing seed of the plant. A "cotton FAB-1 gene", "ghFAB-1 gene" or the like as used herein refers to a nucleotide sequence encoding KASII in cotton, which is expressed in developing cottonseed. A ghFAB-1 gene can readily be distinguished from genes encoding other KAS proteins or other proteins by those skilled in the art, in particular from KASI and KASIII genes, for example the FAB-1 gene is distinct from the nucleotide sequence of KASIII from *Arabidopsis thaliana* (Accession No. NP_001031221) and from the nucleotide sequence of KASI of *Arabidopsis thaliana* (Accession No. NP_199441) Cotton FAB-1 genes include the naturally occurring alleles or variants existing in cotton, including those encoded by the A and D genomes of tetraploid cotton, as well as non-naturally occurring variants which may be produced by those skilled in the art of gene modification. An example of a second gene encoding cotton KASII has the nucleotide sequence shown herein as SEQ ID NO: 3, encoding a protein with amino acid sequence SEQ ID NO: 4, which has about 92% identity to SEQ ID NO: 2. In a preferred embodiment, a ghFAB-1 gene refers to a nucleic acid molecule, which may be present in or isolated from cotton or derived therefrom, comprising nucleotides having a sequence having at least 90% identity to the protein coding region of the cDNA sequence shown in SEQ ID NO:1.

A "FAD2 gene", "FAD2 gene" or the like as used herein refers to a nucleotide sequence encoding oleoyl-Δ12-desaturase in a plant, which is expressed in developing seed of the plant.

A "cotton FAD2-1 gene", "ghFAD2-1 gene" or the like as used herein refers to a nucleotide sequence encoding oleoyl-Δ12-desaturase in cotton, which is expressed in developing cottonseed. A ghFAD2-1 gene can readily be distinguished from genes encoding other oleoyl-Δ12-desaturases or other proteins by those skilled in the art, in particular from a ghFAD2-2 gene, for example Accession No. Y10112 Cotton FAD2-1 genes include the naturally occurring alleles or variants existing in cotton, including those encoded by the A and D genomes of tetraploid cotton, as well as non-naturally occurring variants which may be produced by those skilled in the art of gene modification. An example of a naturally occurring variant of cotton ghFAD2-1 is the sequence shown herein as SEQ ID NO: 8, which has about 96% identity along its full length to SEQ ID NO: 6. In a preferred embodiment, a ghFAD2-1 gene refers to a nucleic acid molecule, which may be present in or isolated from cotton or derived therefrom, comprising nucleotides having a sequence having at least 90% identity to the protein coding region of the cDNA sequence shown in SEQ ID NO: 6.

A "gene encoding SAD-1", "SAD-1 gene" or the like as used herein refers to a nucleotide sequence encoding stearoyl-Δ9-desaturase in a plant, which is expressed in developing seed of the plant.

A "cotton SAD-1 gene", "ghSAD-1 gene" or the like as used herein refers to a nucleotide sequence encoding stearoyl-Δ9-desaturase in cotton, which is expressed in developing cottonseed. A ghSAD-1 gene can readily be distinguished from genes encoding other stearoyl-Δ9-desaturase or other proteins by those skilled in the art. Cotton SAD-1 genes include the naturally occurring alleles or variants existing in cotton, including those encoded by the A and D genomes of tetraploid cotton, as well as non-naturally occurring variants which may be produced by those skilled in the art of gene modification. In a preferred embodiment, a ghSAD-1 gene refers to a nucleic acid molecule, which may be present in or isolated from cotton or derived therefrom, comprising nucleotides having a sequence having at least 90% identity to the protein coding region of the cDNA sequence shown in SEQ ID NO: 22 (Accession No. AJ132636 and corrected versions thereof).

A "cotton CPA-FAS-2 gene", "ghCPA-FAS-2 gene" or the like as used herein refers to a nucleotide sequence encoding CPA fatty acid synthase in cotton, which is expressed in developing cottonseed. A ghCPA-FAS-2 gene can readily be distinguished from genes encoding other CPA fatty acid synthases or other proteins by those skilled in the art, in particular from a ghCPA-FAS-1, for example SEQ ID NO: 11, or from a ghCPA-FAS-3 gene, for example SEQ ID NO: 15. Cotton CPA-FAS-2 genes include the naturally occurring alleles or variants existing in cotton, including those encoded by the A and D genomes of tetraploid cotton, as well as non-naturally occurring variants which may be produced by those skilled in the art of gene modification. In a preferred embodiment, a ghCPA-FAS-2 gene refers to a nucleic acid molecule, which may be present in or isolated from cotton or derived therefrom, comprising nucleotides having a sequence having at least 90% identity to the protein coding region of the cDNA sequence shown in SEQ ID NO: 13.

A genomic form or clone of a gene containing the transcribed region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or for integration into the host genome.

As used herein, a "chimeric gene" refers to any gene that is not a native gene in its native location. Typically a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule" refers to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. These include gene sequences found in that cell so long as the introduced gene contains some modification (e.g. a mutation, the presence of a selectable marker gene, etc.) relative to the naturally-occurring gene. Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Polynucleotides

The present invention refers to various polynucleotides. As used herein, a "polynucleotide" or "nucleic acid" or "nucleic acid molecule" means a polymer of nucleotides, which may be DNA or RNA or a combination thereof, and includes mRNA, cRNA, cDNA, tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid".

By "isolated" is meant material that is substantially or essentially free from components that normally accompany it in its native state. As used herein, an "isolated polynucleotide" or "isolated nucleic acid molecule" means a polynucleotide which is at least partially separated from, preferably substantially or essentially free of, the polynucleotide sequences of the same type with which it is associated or linked in its native state. For example, an "isolated polynucleotide" includes a polynucleotide which has been purified or separated from the sequences which flank it in a naturally occurring state, e.g., a DNA fragment which has been removed from the sequences which are normally adjacent to the fragment. Preferably, the isolated polynucleotide is also at least 90% free from other components such as proteins, carbohydrates, lipids etc. The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably connected to the nucleotide sequence.

The present invention refers to use of oligonucleotides. As used herein, "oligonucleotides" are polynucleotides up to 50 nucleotides in length. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

Polynucleotides used as a probe are typically conjugated with a detectable label such as a radioisotope, an enzyme, biotin, a fluorescent molecule or a chemiluminescent molecule. Oligonucleotides of the invention are useful in methods of detecting an allele of ghFAB-1, ghFAD2-1, ghSAD-1 and ghCPA-FAS-2 or other gene linked to a trait of interest, for example modified oil composition. Such methods, for example, employ nucleic acid hybridization and in many instances include oligonucleotide primer extension by a suitable polymerase (as used in PCR).

A variant of an oligonucleotide of the invention includes molecules of varying sizes of, and/or are capable of hybridizing, for example, to the cotton genome close to that of, the specific oligonucleotide molecules defined herein. For example, variants may comprise additional nucleotides (such as 1, 2, 3, 4, or more), or less nucleotides as long as they still hybridize to the target region. Furthermore, a few nucleotides may be substituted without influencing the ability of the oligonucleotide to hybridize to the target region. In addition, variants may readily be designed which hybridize close to, for example to within 50 nucleotides, the region of the plant genome where the specific oligonucleotides defined herein hybridize.

The terms "polynucleotide variant" and "variant" and the like refer to polynucleotides or their complementary forms displaying substantial sequence identity with a reference polynucleotide sequence. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that encode polypeptides that exhibit enzymatic or other regulatory activity, or polynucleotides capable of serving as selective probes or other hybridizing agents. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

By "corresponds to" or "corresponding to" is meant a polynucleotide (a) having a nucleotide sequence that is substantially identical or complementary to all or most of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein. Terms used to describe sequence relationships between two or more polynucleotides or polypeptides include "reference sequence", "comparison window", "sequence identity", "percentage of sequence identity", "substantial identity" and "identical", and are defined with respect to a minimum number of nucleotides or amino acid residues or over the full length. The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The % identity of a polynucleotide can be determined by GAP (Needleman and Wunsch, *J. Mol. Biol.* 48: 443-453, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides, or at least 400, at least 500 or at least 600 nucleotides in each case. Reference also may be made to the BLAST family of programs as for example disclosed by Altschul et al., *Nucleic Acids Res.* 25: 3389, 1997. A detailed discussion of sequence analysis can be found in Unit 19.3 of Ausubel et al., "*Current Protocols in Molecular Biology*", John Wiley & Sons Inc, 1994-1998, Chapter 15.

Nucleotide or amino acid sequences are indicated as "essentially similar" when such sequences have a sequence identity of at least 90%, especially at least 95%, more especially are identical. It is clear that when RNA sequences are described as essentially similar to, correspond to, or have a certain degree of sequence identity with, DNA sequences, thymine (T) in the DNA sequence is considered equal to uracil (U) in the RNA sequence.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 70%, preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Preferably, a polynucleotide of the invention which encodes a polypeptide with KASII, FAD2, SAD or CPA-FAS activity is greater than 800, preferably greater than 900, and even more preferably greater than 1,000 nucleotides in length.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

The present invention refers to the stringency of hybridization conditions to define the extent of complementarity of two polynucleotides. "Stringency" as used herein, refers to the temperature and ionic strength conditions, and presence or absence of certain organic solvents, during hybridization and washing. The higher the stringency, the higher will be the degree of complementarity between a target nucleotide sequence and the labelled polynucleotide sequence (probe). "Stringent conditions" refers to temperature and ionic conditions under which only nucleotide sequences having a high frequency of complementary bases will hybridize. As used herein, the term "hybridizes under low stringency, medium stringency, high stringency, or very high stringency conditions" describes conditions for hybridization and washing. Guidance for performing hybridization reactions can be found in Ausubel et al., (eds.), *Current Protocols in Molecular Biology*, John Wiley & Sons, NY, 6.3.1-6.3.6., 1989. Aqueous and nonaqueous methods are described in that reference and either can be used. Specific hybridization conditions referred to herein are as follows: 1) low stringency hybridization conditions are for hybridization in 6× sodium chloride/sodium citrate (SSC) at 45° C., followed by two washes in 0.2×SSC, 0.1% SDS at 50-55° C.; 2) medium stringency hybridization conditions are for hybridization in 6×SSC at about 45° C., followed by one or more washes in 0.2×SSC, 0.1% SDS at 60° C.; 3) high stringency hybridization conditions are for hybridization in 6×SSC at 45° C., followed by one or more washes in 0.2×SSC, 0.1% SDS at 65° C.; and 4) very high stringency hybridization conditions are for hybridization in 0.5 M sodium phosphate buffer, 7% SDS at 65° C., followed by one or more washes at 0.2×SSC, 1% SDS at 65° C.

Polypeptides

The terms "polypeptide" and "protein" are generally used interchangeably. The terms "proteins" and "polypeptides" as used herein also include variants, mutants, modifications, analogs and/or derivatives of the polypeptides of the invention as described herein. As used herein, "substantially purified polypeptide" refers to a polypeptide that has been separated from the lipids, nucleic acids, other peptides and other molecules with which it is associated in its native state. Preferably, the substantially purified polypeptide is at least 90% free from other components with which it is naturally associated. By "recombinant polypeptide" is meant a polypeptide made using recombinant techniques, i.e., through the expression of a recombinant polynucleotide in a cell, preferably a plant cell and more preferably a cereal plant cell.

The % identity of a polypeptide relative to another polypeptide can be determined by GAP (Needleman and Wunsch, 1970 (supra)) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids.

As used herein a "biologically active" fragment of a polypeptide is a portion of a polypeptide of the invention, less than full length, which maintains a defined activity of the full-length polypeptide. Biologically active fragments can be any size as long as they maintain the defined activity, but are preferably at least 200 or at least 250 amino acid residues long.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants (variants) of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics.

Mutant (altered variant) peptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama, *Trends Biotechnol.* 16: 76-82, 1998. These DNA shuffling techniques may include genes related to those of the present invention, such as genes from plant species other than cotton, and/or include different genes from the same plant encoding similar proteins. Products derived from mutated/altered DNA can readily be screened using techniques described herein to determine if they possess, for example, KASII or FAD2 activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 7 under the heading of "exemplary substitutions".

Polypeptides of the present invention can be produced in a variety of ways, including production and recovery of natural polypeptides, and production and recovery of recombinant polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention.

The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In certain embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, including a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of the plant, such as, for example, endosperm, embryo, leaves, fruit, tubers or root. In a preferred embodiment, a promoter is expressed selectively or preferentially in developing seed of a seed-bearing plant, preferably a cotton plant. The term may also refer to expression at specific developmental stages in an organ, such as in early, mid or late embryogenesis or different stages of maturity, or to expression that is inducible by certain environmental conditions or treatments. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in a plant. Typically, the promoter is expressed at a level 10-fold higher in the specific tissue or organ than in other tissues or organs. An illustrative tissue specific promoter is the promoter from a lectin gene which is expressed preferentially in the developing seed of dicot plants such as cotton. Other seed specific promoters are well known in the art.

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters, tissue specific promoters (see, e.g., U.S. Pat. No. 5,459,252 to Conkling et al.; WO 91/13992 to Advanced Technologies); promoters from viruses (including host specific viruses), or partially or wholly synthetic promoters. Numerous promoters that are functional in mono- and dicotyledonous plants are well known in the art (see, for example, Greve, *J. Mol. Appl. Genet.,* 1: 499-511, 1983; Salomon et al., *EMBO* 1, 3: 141-146, 1984; Garfinkel et al., *Cell,* 27: 143-153, 1983; Barker et al., *Plant Mol. Biol.,* 2: 235-350, 1983; including various promoters isolated from plants and viruses such as the cauliflower mosaic virus promoter (CaMV 35S, 19S). Many tissue specific promoter regions are known, including those from genes encoding enzymes involved in oil biosynthesis in seeds, or encoding napin, seed ACP, zein, or other seed storage proteins. Non-limiting methods for assessing promoter activity are disclosed by Medberry et al., *Plant Cell,* 4: 185-192, 1992, Medberry et al., *Plant J.* 3: 619-626, 1993, Sambrook et al., *Molecular Cloning: A Laboratory Manual* (2*nd Ed*). Cold Spring Harbour Laboratory, Cold Spring Harbour, N.Y. 1989 and McPherson et al. (U.S. Pat. No. 5,164,316).

Alternatively or additionally, the promoter may be an inducible promoter or a developmentally regulated promoter which is capable of driving expression of the introduced polynucleotide at an appropriate developmental stage of the plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from a lectin gene, the S3 gene of Subclover Stunt Virus, or nopaline synthase (nos) gene of *Agrobacterium tumefaciens* (Bevan et al., *Nucl. Acid Res.,* 11: 369, 1983). Suitable 3' non-translated sequences may also be derived from plant genes such as the 3' end of the protease inhibitor I or II genes from potato or tomato, the soybean storage protein genes and the small subunit of the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5 leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi, *Nucl. Acid Res.* 15: 6643, 1987.

Additionally, targeting sequences may be employed to target the enzyme encoded by the foreign or exogenous polynucleotide to an intracellular compartment, for example to the chloroplast, within plant cells or to the extracellular environment. For example, a nucleic acid sequence encoding a transit or signal peptide sequence may be operably linked to a sequence that encodes a chosen enzyme of the subject invention such that, when translated, the transit or signal peptide can transport the enzyme to a particular intracellular or extracellular destination, and can then be optionally post-translationally removed. Transit or signal peptides act by facilitating the transport of proteins through intracellular membranes, e.g., endoplasmic reticulum, vacuole, vesicle, plastid, mitochondrial and plasmalemma membranes. For example, the targeting sequence can direct a desired protein to a particular organelle such as a vacuole or a plastid (e.g., a chloroplast), rather than to the cytosol. Thus, the nucleic acid construct of the invention can further comprise a plastid transit peptide-encoding nucleic acid sequence operably linked between a promoter region and the foreign or exogenous polynucleotide.

Vectors

The present invention includes use of vectors for manipulation or transfer of genetic constructs. By "vector" is meant a nucleic acid molecule, preferably a DNA molecule derived, for example, from a plasmid, bacteriophage, or plant virus, into which a nucleic acid sequence may be inserted or cloned. A vector preferably is double-stranded DNA and contains one or more unique restriction sites and may be capable of autonomous replication in a defined host cell including a target cell or tissue or a progenitor cell or tissue thereof, or capable of integration into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP-A 256223; a glutamine synthetase gene conferring, upon overexpression, resistance to glutamine synthetase inhibitors such as phosphinothricin as, for example, described in WO87/05327, an acetyltransferase gene from *Streptomyces viridochromogenes* conferring resistance to the selective agent phosphinothricin as, for example, described in EP-A 275957, a gene encoding a 5-enolshikimate-3-phosphate synthase (EPSPS) conferring tolerance to N-phosphonomethylglycine as, for example, described by Hinchee et al., *Biotech.* 6: 915, 1988, a bar gene conferring resistance against bialaphos as, for example, described in WO91/02071; a nitrilase gene such as bxn from *Klebsiella ozaenae* which confers resistance to bromoxynil (Stalker et al., *Science,* 242: 419, 1988); a dihydrofolate reductase (DHFR) gene conferring resistance to methotrexate (Thillet et al., *J. Biol. Chem.* 263: 12500, 1988); a mutant acetolactate synthase gene (ALS), which confers resistance to imidazolinone, sulfonylurea or other ALS-inhibiting chemicals (EP-A-154 204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., *Biochem. Biophys. Res. Comm.* 126: 1259-68, 1985), which may be employed in calcium-sensitive bioluminescence detection; a green fluorescent protein gene (Niedz et al., *Plant Cell Reports,* 14: 403, 1995) or derivatives thereof; a luciferase (luc) gene (Ow et al., *Science,* 234: 856, 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Methods of Modifying Gene Expression

The level of a protein, for example an enzyme involved in oil biosynthesis in developing seeds of a plant, may be modulated by increasing the level of expression of a nucleotide sequence that codes for the protein in a plant cell, or decreasing the level of expression of a gene encoding the protein in the plant, leading to modified oil composition in the mature seed. The level of expression of a gene may be modulated by altering the copy number per cell, for example by introducing a synthetic genetic construct comprising the coding sequence and a transcriptional control element that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in a substantial modification of oil composition. This may be detected by simple testing of seedoil from the transformants. Alternatively, a population of mutagenized seed or a population of plants from a breeding program may be screened for individual lines with altered oil content or composition.

Reducing gene expression may be achieved through introduction and transcription of a "gene-silencing chimeric gene" introduced into the plant cell. The gene-silencing chimeric gene may be introduced stably into the plant cell's genome, preferably nuclear genome, or it may be introduced transiently, for example on a viral vector. As used herein "gene-silencing effect" refers to the reduction of expression of a target nucleic acid in a plant cell, which can be achieved by introduction of a silencing RNA. Such reduction may be the result of reduction of transcription, including via methylation of chromatin remodeling, or post-transcriptional modification of the RNA molecules, including via RNA degradation, or both. Gene-silencing includes an abolishing of the expression of the target nucleic acid or gene and a partial reduction in either extent or duration. It is sufficient that the level of expression of the target nucleic acid in the presence of the silencing RNA is lower that in the absence thereof. The level of expression may be reduced by at least about 40%, or at least about 50%, or at least about 60%, or at least about 70%, or at least about 80%, or at least about 90%, or at least about 95%, or at least about 99%. In preferred embodiments, the expression of the cotton ghFAB-1 or ghCPA-FAS-2 gene is reduced in seed by at least 60%, more preferably by at least 80% relative to a corresponding seed lacking the gene-silencing chimeric DNA. The target nucleic acid may be a gene involved in oil biosynthesis, oil accumulation such as genes involved in TAG assembly, including but not limited to acyltransferases or other enzymes of the Kennedey pathway, or oil metabolism, or may be any other endogenous genes, transgenes or exogenous genes such as viral genes which may not be present in the plant cell at the time of introduction of the transgene.

Antisense RNA Molecules

Antisense techniques may be used to reduce gene expression according to the invention. The term "antisense RNA" shall be taken to mean an RNA molecule that is complementary to at least a portion of a specific mRNA molecule and capable of reducing expression of the gene encoding the mRNA. Such reduction typically occurs in a sequence-dependent manner and is thought to occur by interfering with a post-transcriptional event such as mRNA transport from nucleus to cytoplasm, mRNA stability or inhibition of translation. The use of antisense methods is well known in the art (see for example, Hartmann and Endres, *Manual of Antisense Methodology*, Kluwer, 1999). The use of antisense techniques in plants has been reviewed by Bourque, *Plant Science,* 105: 125-149, 1995 and Senior, *Biotech. Genet. Engin. Revs.* 15: 79-119, 1998. Bourque, 1995 (supra) lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior, 1998 (supra) states that antisense methods are now a very well established technique for manipulating gene expression.

As used herein, the term "an antisense polynucleotide which hybridizes under physiological conditions" means that the polynucleotide (which is fully or partially single stranded) is at least capable of forming a double stranded polynucleotide with an RNA product of the gene to be inhibited, typically the mRNA encoding a protein such as those provided herein, under normal conditions in a cell. Antisense molecules may include sequences that correspond to the structural genes or for sequences that effect control over the gene expression or splicing event. For example, the antisense sequence may correspond to the coding region of the targeted gene, or the 5'-untranslated region (UTR) or the 3'-UTR or combination of these. It may be complementary in part to intron sequences, which may be spliced out during or after transcription, but is preferably complementary only to exon sequences of the target gene. In view of the generally greater divergence of the UTRs, targeting these regions provides greater specificity of gene inhibition.

The length of the antisense sequence should be at least 19 contiguous nucleotides, preferably at least 25 or 30 or 50 nucleotides, and more preferably at least 100, 200, 500 or 1000 nucleotides, to a maximum of the full length of the gene to be inhibited. The full-length sequence complementary to the entire gene transcript may be used. The length is most preferably 100-2000 nucleotides. The degree of identity of the antisense sequence to the targeted transcript should be at least 90% and more preferably 95-100%. Preferred antisense sequences comprise at least 30 contiguous nucleotides which are the complement of any sequence of at least 30 contiguous nucleotides from SEQ ID Nos: 1, 5, or 12. The antisense RNA molecule may of course comprise unrelated sequences which may function to stabilize the molecule.

Genetic constructs to express an antisense RNA may be readily made by joining a promoter sequence to a region of the target gene in an "antisense" orientation, which as used herein refers to the reverse orientation relative to the orientation of transcription and translation (if it occurs) of the sequence in the target gene in the plant cell. Accordingly, also provided by this invention is a nucleic acid molecule such as a chimeric DNA coding for an antisense RNA of the invention, including cells, tissues, organs, plants, seeds, particularly cotton plants or cottonseed and the like comprising the nucleic acid molecule.

Ribozymes

The term "ribozyme" as used herein refers to an RNA molecule which specifically recognizes a distinct substrate RNA and catalyzes its cleavage. Typically, the ribozyme contains a region of nucleotides which are complementary to a region of the target RNA, enabling the ribozyme to specifically hybridize to the target RNA under physiological conditions, for example in the cell in which the ribozyme acts, and an enzymatic region referred to herein as the "catalytic domain". The types of ribozymes that are particularly useful in this invention are the hammerhead ribozyme (Haseloff and Gerlach, *Nature* 334: 585-591, 1988, Perriman et al., *Gene,* 113: 157-163, 1992) and the hairpin ribozyme (Shippy et al., *Mol. Biotech.* 12: 117-129, 1999). DNA encoding the ribozymes can be synthesized using methods well known in the art and may be incorporated into a genetic construct or expression vector for expression in the cell of interest. Accordingly, also provided by this invention is a nucleic acid molecule such as a chimeric DNA coding for a ribozyme of the invention, including cells, tissues, organs, plants, grain and the like comprising the nucleic acid molecule. Typically, the DNA encoding the ribozyme is inserted into an expression cassette under control of a promoter and a transcription termination signal that function in the cell. Specific ribozyme cleavage sites within any potential RNA target may be identified by scanning the target molecule for ribozyme cleavage sites which include the trinucleotide sequences GUA, GUU and GUC. Once identified, short RNA sequences of between about 5 and 20 ribonucleotides corresponding to the region of the target gene 5' and 3' of the cleavage site may be evaluated for predicted structural features such as secondary structure that may render the oligonucleotide sequence less suitable. When employed, ribozymes may be selected from the group consisting of hammerhead ribozymes, hairpin ribozymes, axehead ribozymes, newt satellite ribozymes, Tetrahymena ribozymes and RNAse P ribozymes, and are designed according to methods known in the art based on the sequence of the target gene (for instance, see U.S. Pat. No. 5,741,679). The suitability of candidate targets may also be evaluated by testing their accessibility to hybridization with complementary oligonucleotides, using ribonuclease protection assays.

As with antisense polynucleotides described herein, ribozymes of the invention should be capable of hybridizing to a target nucleic acid molecule (for example SEQ ID Nos: 1, 3, 6 or 13) under "physiological conditions", namely those conditions within a cell, especially conditions in a plant cell such as a cotton cell.

RNA Interference/Duplex RNA

As used herein, "artificially introduced dsRNA molecule" refers to the introduction of dsRNA molecule, which may be produced in the cell by transcription from a chimeric gene encoding such dsRNA molecule, however does not refer to the conversion of a single stranded RNA molecule into a dsRNA inside the eukaryotic cell or plant cell. RNA interference (RNAi) is particularly useful for specifically reducing the expression of a gene or inhibiting the production of a particular protein. Although not wishing to be limited by theory, Waterhouse et al., *Proc. Natl. Acad. Sci. U.S.A.* 95: 13959-13964, 1998 have provided a model for the mechanism by which dsRNA can be used to reduce gene expression or protein production. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are transcribed to produce a hairpin RNA in which the sense and anti-sense sequences hybridize to form the dsRNA region with an intervening sequence or spacer region forming a loop structure, so the hairpin RNA comprises a stem-loop structure. The design and production of suitable dsRNA molecules for the present invention is well within the capacity of a person skilled in the art, particularly considering Waterhouse et al., 1998 (supra), Smith et al., *Nature,* 407: 319-320, 2000, WO 99/53050, WO 99/49029, and WO 01/34815. Accordingly, also provided by this invention is a nucleic acid molecule such as a chimeric DNA coding for a duplex RNA such as a hairpin RNA of the invention, including cells, tissues, organs, plants, seeds, particularly cotton plants or cottonseed, and the like comprising the nucleic acid molecule. In a preferred embodiment, the chimeric DNA has the structure shown schematically in FIG. 5.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. A preferred intron is an intron from the ghFAD2-1 gene. This arrangement has been shown to result in a higher efficiency of gene silencing (Smith et al., 2000 (supra)). The double-stranded region may comprise one or two RNA molecules, transcribed from either one DNA region or two. The dsRNA may be classified as long hpRNA, having long, sense and antisense regions which can be largely complementary, but need not be entirely complementary (typically forming a basepaired region larger than about 100 bp, preferably ranging between 200-1000 bp). hpRNA can also be smaller with the double-stranded portion ranging in size from about 30 to about 50 bp, or from 30 to about 100 bp (see WO04/073390, herein incorporated by reference). The presence of the double stranded RNA region is thought to trigger a response from an endogenous plant system that processes the double stranded RNA to oligonucleotides of 21-24 nucleotides long, and also uses these oligonucleotides for sequence-specific cleavage of the homologous RNA transcript from the target plant gene, efficiently reducing or eliminating the activity of the target gene.

The length of the sense and antisense sequences that hybridize should each be at least 19 contiguous nucleotides, preferably at least 21 or at least 27, or at least 30, or at least 50 contiguous nucleotides, and more preferably at least 100, at least 200, or at least 500 contiguous nucleotides, up to the full-length sequence corresponding to the entire gene transcript. The lengths are most preferably 100-2000 contiguous nucleotides. The degree of identity of the sense and antisense sequences to the targeted transcript should be at least 85%, preferably at least 90% and more preferably 95-100%. The longer the sequence, the less stringent the requirement is for overall sequence identity. The RNA molecule may of course comprise unrelated sequences which may function to stabilize the molecule. The RNA molecule may be a hybrid between different sequences targeting different target RNAs, allowing reduction in expression of more than one target gene, or it may be one sequence which corresponds to a family of related target genes such as a multigene family. In a preferred embodiment, the RNA molecule targets at least three different target genes, more preferably the ghFAB-1, ghFAD2-1, ghSAD-1 and ghCPA-FAS-2 genes in cotton. The sequences used in the dsRNA preferably correspond to exon sequences of the target gene and may correspond to 5' and/or 3' untranslated sequences or protein coding sequences or any combination thereof. The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors. Typically, the RNA molecule is expressed under the control of a RNA polymerase II or RNA polymerase III promoter. Examples of the latter include tRNA or snRNA promoters.

Examples of genetic constructs that encode dsRNA molecules that may be used to down-regulate the production of polypeptides for modification of oil composition in seed are provided in Examples 3 and 8.

Other silencing RNA may be "unpolyadenylated RNA" comprising at least 20 consecutive nucleotides having at least 95% sequence identity to the complement of a nucleotide sequence of an RNA transcript of the target gene, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having at least 95% sequence identity to the sequence of the target nucleic acid or the complement thereof, and further comprising a largely-double stranded region as described in WO03/076619.

MicroRNA regulation is a specialized branch of the RNA silencing pathway that evolved towards gene regulation, diverging from conventional RNAi/PTGS. MicroRNAs are a specific class of small RNAs that are encoded in gene-like elements organized in a characteristic partial inverted repeat. When transcribed, microRNA genes give rise to partially basepaired stem-looped precursor RNAs from which the microRNAs are subsequently processed. MicroRNAs are typically 21 nucleotides in length or 21-23 nucleotides in length. The released miRNAs are incorporated into RISC-like complexes containing a particular subset of Argonaute proteins that exert sequence-specific gene repression (see, for example, Millar and Waterhouse, *Fund Integr Genomics,* 5: 129-135, 2005; Pasquinelli et al., *Curr Opin Genet Develop*

15: 200-205, 2005; Almeida and Allshire, *Trends Cell Biol.* 15: 251-258, 2005, herein incorporated by reference).

Cosuppression

Another molecular biological approach that may be used for specifically reducing gene expression is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the "sense orientation" with respect to a promoter for its expression, which as used herein refers to the same orientation as transcription and translation (if it occurs) of the sequence relative to the sequence in the target gene. The size of the sense fragment, its correspondence to target gene regions, and its degree of homology to the target gene are as for the antisense sequences described above. In some instances the additional copy of the gene sequence interferes with the expression of the target plant gene. Reference is made to patent specification WO 97/20936 and European patent specification 0465572 for methods of implementing co-suppression approaches. The antisense, co-suppression or double stranded RNA molecules may also comprise a largely double-stranded RNA region, preferably comprising a nuclear localization signal, as described in WO 03/076619.

Any of these technologies for reducing gene expression can be used to coordinately reduce the activity of multiple genes. For example, one RNA molecule can be targeted against a family of related genes by targeting a region of the genes which is in common. Alternatively, unrelated genes may be targeted by including multiple regions in one RNA molecule, each region targeting a different gene. This can readily be done by fusing the multiple regions under the control of a single promoter, such as in Example 8.

Methods of Introducing Nucleic Acids into Plant Cells/Transformation

A number of techniques are available for the introduction of nucleic acid molecules into a plant host cell, well known to workers in the art. The term "transformation" means alteration of the genotype of an organism, for example a bacterium or a plant, by the introduction of a foreign or exogenous nucleic acid. By "transformant" is meant an organism so altered. As used herein the term "transgenic" refers to a genetically modified plant in which the endogenous genome is supplemented or modified by the integration, or stable maintenance in a replicable non-integrated form, of an introduced foreign or exogenous gene or sequence. By "transgene" is meant a foreign or exogenous gene or sequence that is introduced into the genome of a plant. The nucleic acid molecule may be stably integrated into the genome of the plant, or it may be replicated as an extrachromosomal element. By "genome" is meant the total inherited genetic complement of the cell, plant or plant part, and includes chromosomal DNA, plastid DNA, mitochondrial DNA and extrachromosomal DNA molecules. The term "regeneration" as used herein in relation to plant materials means growing a whole, differentiated plant from a plant cell, a group of plant cells, a plant part such as, for example, from an embryo, scutellum, protoplast, callus, or other tissue, but not including growth of a plant from a seed.

The particular choice of a transformation technology will be determined by its efficiency to transform certain plant species as well as the experience and preference of the person practicing the invention with a particular methodology of choice. It will be apparent to the skilled person that the particular choice of a transformation system to introduce a nucleic acid construct into plant cells is not essential to or a limitation of the invention, provided it achieves an acceptable level of nucleic acid transfer. Guidance in the practical implementation of transformation systems for plant improvement is provided by Birch, *Ann Rev Plant Physiol Plant Mol Biol.* 48: 297-326, 1997.

In principle, both dicotyledonous and monocotyledonous plants that are amenable to transformation can be modified by introducing a nucleic acid construct according to the invention into a recipient cell and growing a new plant that harbors and expresses a polynucleotide according to the invention.

Introduction and expression of foreign or exogenous polynucleotides in dicotyledonous plants such as cotton, tobacco, potato and legumes or monocotyledonous plants such as cereals, including wheat, barley, rice, corn, oats, rye and sorghum has been shown to be possible using the T-DNA of the tumor-inducing (Ti) plasmid of *Agrobacterium tumefaciens* (See, for example, Umbeck, U.S. Pat. No. 5,004,863, and International application PCT/US93/02480). A construct of the invention may be introduced into a plant cell utilizing *A. tumefaciens* containing the Ti plasmid. In using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is preferred that the *Agrobacterium* harbors a binary Ti plasmid system. Such a binary system comprises (1) a first Ti plasmid having a virulence region essential for the introduction of transfer DNA (T-DNA) into plants, and (2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells as, for example, described by De Framond, *Biotechnology,* 1: 262, 1983 and Hoekema et al., *Nature,* 303: 179, 1983. Such a binary system is preferred inter alia because it does not require integration into the Ti plasmid in *Agrobacterium.*

Methods involving the use of *Agrobacterium* include, but are not limited to transformation of plant cells or tissues with *Agrobacterium* such as transformation of seeds, apices or meristems with *Agrobacterium*, or inoculation in planta such as the floral-dip method as described by Bechtold et al., *C.R. Acad. Sci. Paris,* 316: 1194, 1993. This approach is based on the infiltration of a suspension of *Agrobacterium* cells. Alternatively, the chimeric construct may be introduced using root-inducing (Ri) plasmids of *Agrobacterium* as vectors.

Methods for transformation of cotton plants by introduction of an exogenous nucleic acid and for regeneration of plants from cells by somatic embryogenesis are well known in the art, Other methods for introducing the nucleic acid construct into a plant cell are by electroporation, or high velocity ballistic penetration by small particles (also known as particle bombardment or microprojectile bombardment) with the nucleic acid to be introduced contained either within the matrix of small beads or particles, or on the surface thereof as, for example described by Klein et al., *Nature,* 327: 70, 1987.

As used herein, an "induced mutation" is an artificially induced genetic variation which may be the result of chemical, radiation or biologically-based mutagenesis, for example transposon or T-DNA insertion. Preferred mutations are null mutations such as nonsense mutations, frameshift mutations, insertional mutations or splice-site variants which completely inactivate the gene of interest. Nucleotide insertional derivatives include 5' and 3' terminal fusions as well as intra-sequence insertions of single or multiple nucleotides. Insertional nucleotide sequence variants are those in which one or more nucleotides are introduced into the nucleotide sequence, which may be obtained by random insertion with suitable screening of the resulting products. Deletional variants are characterized by the removal of one or more nucleotides from the sequence. Preferably, a mutant gene has only a single insertion or deletion of a sequence of nucleotides relative to the wild-type gene. Substitutional nucleotide variants are those in which at least one nucleotide in the sequence has been removed and a different nucleotide inserted in its place. The preferred number of nucleotides affected by substitutions in a mutant gene relative to the wild-type gene is a maximum of ten nucleotides, more preferably a maximum of 9, 8, 7, 6, 5, 4, 3, or 2, or only one nucleotide. Such a substitution may be "silent" in that the substitution does not change the amino acid defined by the codon. Alternatively, conservative substituents are designed to alter one amino acid for another similar acting amino acid.

The term "mutation" as used herein does not include silent nucleotide substitutions which do not affect the activity of the gene, and therefore includes only alterations in the gene sequence which affect the gene activity. The term "polymorphism" refers to any change in the nucleotide sequence including such silent nucleotide substitutions.

Mutagenesis can be achieved by chemical or radiation means, for example EMS or sodium azide (Zwar and Chandler, *Planta* 197: 39-48, 1995) treatment of seed, or gamma irradiation, well know in the art. Isolation of mutants may be achieved by screening mutagenised plants or seed. In a polyploid plant such as cotton, screening is preferably done in a genotype that is already lacks one of the enzyme activities, so that a mutant entirely lacking the functional activity is sought. Alternatively, the mutation may be identified using techniques such as "tilling" in a population mutagenised with an agent such as EMS (Slade and Knauf, *Transgenic Res.* 14: 109-115, 2005). Such mutations may then be introduced into desirable genetic backgrounds by crossing the mutant with a plant of the desired genetic background and performing a suitable number of backcrosses to cross out the originally undesired parent background. The invention clearly extends to methods of producing or identifying such plants or the seed produced by such plants.

The process of producing plants of the invention may include mutagenesis and/or screening steps such as TILLING (Targeting Induced Local Lesions IN Genomes). In a first step, introduced mutations such as novel single base pair changes are induced in a population of plants by treating cells, seeds, pollen or other plant parts with a chemical mutagen or radiation, and then advancing plants to a generation where mutations will be stably inherited. DNA is extracted, and seeds are stored from all members of the population to create a resource that can be accessed repeatedly over time. For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cell, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique. TILLING is further described in Slade and Knauf, 2005 (supra), and Henikoff et al., *Plant Physiol.* 135: 630-636, 2004, herein incorporated by reference.

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., *Plant J.* 37: 778-786, 2004).

As used herein, the term "genetically linked" refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the situation where the marker locus comprises a polymorphism that is responsible for the trait of interest (in other words the marker locus is directly "linked" to the phenotype). Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM or 2 cM apart and most preferably about 0 cM apart.

As used herein, the "other genetic markers" may be any molecules which are linked to a desired trait of a plant, preferably a cotton plant. Such markers are well known to those skilled in the art and include molecular markers linked to genes determining traits such disease resistance, yield, plant morphology, lint quality etc. Any molecular biological technique known in the art which is capable of detecting alleles of genes of interest can be used in the methods of the present invention. Such methods include, but are not limited to, the use of nucleic acid amplification, nucleic acid sequencing, nucleic acid hybridization with suitably labelled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof. The invention also includes the use of molecular marker techniques to detect polymorphisms linked to alleles of. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (McPherson and Moller (Ed), BIOS Scientific Publishers Ltd, Oxford, 2000). PCR can be performed on cDNA obtained from reverse transcribing mRNA isolated from plant cells expressing an SSII gene or on genomic DNA isolated from a plant. A primer in this context is an oligonucleotide sequence that is capable of hybridizing in a sequence specific fashion to the target sequence and being extended during the PCR. Amplicons or PCR products or PCR fragments or amplification products are extension products that comprise the primer and the newly synthesized copies of the target sequences. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target, target sequence or template refer to nucleic acid sequences which are amplified.

Methods for direct sequencing of nucleotide sequences are well known to those skilled in the art and can be found for example in Ausubel et al., (supra) and Sambrook et al., (supra). Sequencing can be carried out by any suitable method, for example, dideoxy sequencing, chemical sequencing or variations thereof. Direct sequencing has the advantage of determining variation in any base pair of a particular sequence.

Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these, particularly seed comprising modified oil composition.

As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

A "transgenic plant" as used herein refers to a plant that contains a gene construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants". A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "corresponding non-transgenic plant" refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention, Wild-type cells, tissue or plants may be used as controls to compare levels of expression of an exogenous nucleic acid or the extent and nature of trait modification with cells, tissue or plants modified as described herein. A typical wild-type plant with respect to cotton is of the variety "Coker".

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein/enzyme defined herein in the desired plant or plant organ. Transgenic plant parts include all parts and cells of said plants comprising the transgene such as, for example, cultured tissues, callus and protoplasts.

Any of several methods may be employed to determine the presence of a transgene in a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers to amplify a specific DNA, the presence of which will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed may also be identified i.e. distinguished from non-transformed or wild-type plants by their phenotype, for example conferred by the presence of a selectable marker gene, or conferred by the phenotype of modified oil composition of seed of the plant, or related phenotype such as altered enzyme activity.

As used herein, "germination" refers to the emergence of the root tip from the seed coat after imbibition. "Germination rate" refers to the percentage of seeds in a population which have germinated over a period of time, for example 14 or 21 days, after imbibition. A population of seeds can be assessed daily over several days to determine the germination percentage over time. With regard to seeds of the present invention, as used herein the term "germination rate which is substantially the same" means that the germination rate of the transgenic seeds is at least 80% that of isogenic wild-type seeds.

Plants provided by or contemplated for use in the practice of the present invention include angiosperms, including both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruit. Preferably, the plant is a cotton plant, and the plant cell is a cotton plant cell. Examples of cereal plants include, but are not limited to, wheat, barley, rice, maize (corn), sorghum, oats, and rye. In an embodiment, the cotton plant is a progeny plant of the line DCS9 (Example 7) and contains the same transgene located in the same position in the genome.

As used herein, the term "cotton" refers to any species of the Genus *Gossypium*, preferably of the species *Gossypium hirsutum* or *Gossypium barbadense.*

Food Production

In another aspect, the invention provides plants, particularly cotton plants, and seed, particularly cottonseed, and products obtained therefrom comprising oil from the seed, particularly cottonseed oil, that is useful for food or feed production or for non-food uses, the seed having modified seedoil composition compared to corresponding wild-type seed. Preferably the plant from which the seed is obtained has a reduced level of KASII, preferably also a reduced level of FAD2 and/or SAD-1, and optionally further a reduced level of CPA-FAS-2 activities in the seed during development. The seedoil may also have a reduced level of CPA, CPE and/or gossypol. The seedoil of the present invention is useful for food production and in particular for commercial food production, for example in the manufacture of chocolates or other confectionary. Such food production might include mixing the seedoil as one ingredient with other ingredients in commercial food production. In preferred embodiments which is desirable for use in food production, the seedoil has a modified composition as specified herein.

Oil is readily isolated from cleaned, de-linted and hulled seeds of the invention using standard methods, for example cooking at high temperatures, pressing, milling using screw press (high pressure) and/or procedures for extraction of oil using solvents, stream and/or high pressure. The oil content of cottonseed, or the content of any fatty acid in the oil of cottonseed, is conveniently determined as described herein. Alternatively or in addition the procedures of Folch et al., *J. Biol. Chem.* 226: 497, 1957 or variations thereof as described elsewhere (see for example Liu et al., 2002 (supra)) may be employed. The fatty acid content and/or composition of cotton seed oil may be conveniently determined using gas liquid chromatography against known standard fatty acids, by comparing the fatty acid methyl ester peaks and retention times of the standards with the sample being tested, and by standard integration of the peaks obtained. However, the present invention is not to be limited by the method of determining the content and/or composition of cottonseed oil, in particular the means for determining fatty acid or other lipid components. Oil is composed almost entirely of triacylglycerols (TAGs) that comprise three fatty acids esterified to a glycerol backbone. To assess the TAG content of oil, oil may be purified such as by solid phase extraction (SPE) on silica gel cartridges. The TAG composition may be qualitatively assessed by reverse phase high resolution liquid chromatography (HPLC) using a refractive index detector and propionitrile as mobile phase. From purified oil, fatty acid methyl esters (FAMEs) are prepared such as by methylation with cold solution of KOH in methanol and the esters analysed by capillary gas chromatography (GC) using high polar columns. From the fatty acid composition, the theoretical TAG composition may be calculated by a computer program employing a typical distribution of fatty acids in the triacylglycerol for cottonseed oil. Mathematical algorithms may be calculated from theoretical and experimental (HPLC) triacylglycerol compositions, and the resulting values compared with those contained in a data base comprising data sets determined by conducting the analysis on different standards of oils.

Food Products

The invention also encompasses food products produced with the seedoil. The plant of the invention or products derived therefrom containing oil or lint may be used in a variety of applications for human use or consumption. As used herein, "humans" refers to *Homo sapiens*. The seedoil can be used readily in food processing procedures, in particular where increased melting temperatures of an oil ingredient for the food are desired. The oil may be incorporated into products such as margarine, shortening, mayonnaise, dairy products such as icecream or custard, or added as an ingredient to other foods or food materials, such as bread, cake, biscuits, pastries, breakfast cereals, pasta, noodles or sauces.

Other parts of the plants of the invention that are edible may be used as foods for human consumption or as feed for animal use. For example, leaves, stems, roots, tubers, fruit, pods or extracts or parts of these comprising cells of the invention from any of these may be used for human or animal consumption. Modified oil content and composition of the plants of the invention and parts thereof may provide advantages for use of these materials as animal feed such as, for example, as feed for pigs, cattle, horses, poultry such as chickens and other animals.

The food product may be packaged ready for sale or in bulk form. The invention also provides methods of preparing the food product of the invention, and recipes or instructions for preparing such foods. The methods may comprise the steps of crushing, extracting, milling, cooking, frying, canning, packaging or other processing steps known in the art. The methods or recipes or instructions may include the steps of processing the oil of the invention and/or admixing it with other food ingredients, such as heating or baking the mixture or the product to, for example, at least 100° C. The method may include the step of packaging the product so that it is ready for sale.

The present invention is further described by the following non-limiting Examples.

Example 1

Illustrative Methods and Materials

Isolation of RNA

Two grams of cotton embryos or leaf tissue frozen with liquid nitrogen were ground to a fine powder using a mortar and pestle and transferred to a beaker containing 22 mls cold extraction buffer and stirred constantly. The extraction buffer contained 200 mM Tris-HCl pH8.5, 1.5% Lithium dodecylsulfate, 300 mM LiCl, 10 mM $Na_2$EDTA, 1% sodium deoxycholate, 1% Nonidet P-40. This was followed by adding 5% insoluble PVP, 90 mM mercaptoethanol, 10 mM DTT (dithiothreitol), 0.1% DEPC and stirred for 10 min prior to being transferred to a Corex tube. Then 18.4 ml of 3M ammonium acetate was added and mixed well. It was centrifuged at 6,000×rpm for 20 min at 4° C. The supernatant was transferred to a new tube and precipitated by adding 1/10 volume of 3 M NaAc, pH5.2 and ½ final volume of cold isopropanol and stored at −20° C. fort hour prior to centrifugation at 6,000× rpm for 30 min using a swing rotor. The pellet was resuspended in 1 ml $dH_2O$ and transferred to two Eppendorf tubes (500 μA in each tube). The suspension was extracted with an equal volume of phenol/chloroform/isoamyl alcohol solution (25:24:1) and the phases were separated by centrifugation for 5 min at 4° C. The aqueous top layer was carefully transferred into a new Eppendorf tube and it was extracted again with chloroform as above. Half volume of 5M LiCl was added to the aqueous sample, mixed well and left on ice for 3 hours prior to centrifugation at 12,000×rpm for 15 min at 4° C. The pellet was resuspended in 50 μl $dH_2O$. Finally, the RNA sample was precipitated by adding 5 μl NaAc and 138 μl cold ethanol and incubated on dry ice for 30 minute prior to centrifugation for 15 min at 4° C. The RNA pellet was dried under vacuum and then dissolved in 30 μl RNase-free $H_2O$.

Construction of a Cottonseed cDNA Library

Cotton poly(A)$^+$ RNA was isolated from total RNA prepared as described above, using a mRNA purification kit (Pharmacia), essentially as described by the manufacturer. To prepare cDNA, a cDNA synthesis kit (Pharmacia) was used, essentially as described by the manufacturer, using 1-5 μg poly(A)$^+$ RNA as starting material. The double-stranded cDNA product was blunt-ended, and ligated to EcoRI/NotI adaptors, using standard procedures. Following the removal of excess unligated adaptors, the cDNA was cloned into the bacteriophage vector Lambda ZAPII (Stratagene, USA), and packaged using a commercially-available packaging system (Stratagene, USA), according to the manufacturer's instructions.

The cDNA libraries described herein generally contained about 92% recombinant bacteriophage particles, in a total of about $1.5\times10^7$ plaque forming units (pfu) per ml of unamplified library.

Following plaque-purification of positively hybridizing plaques, the ExAssist/SOLR system (Stratagene, USA) was used to excise the pBluescript SK(−) phagemid from the Lambda ZAPII vector, as described by the manufacturer.

All other methods such as gel electrophoresis, transfer of nucleic acids to membranes for hybridization, preparation of labelled DNA probes, and screening of cDNA libraries were by standard methods (Ausubel et al., (supra)). Unless otherwise stated hybridization conditions were as described by Khandjian, *Bio/Technology,* 5: 165-167, 1987, herein incorporated by reference, using 50 mM Tris-HCl pH7.5, 1M NaCl, 50% formamide, 10×Denhardt's solution, 10% dextran sulfate, 1% SDS, 0.1% sodium pyrophosphate, 0.1 mg/ml herring sperm DNA at 42° C. Membranes were then briefly washed in 2×SSC, 0.1% SDS at 65° C., followed by two further washes in 0.2×SSC, 0.1% SDS at 65° C. for 15 min each (high stringency).

Example 2

Isolation of Cotton cDNAs Encoding KASII

Two cDNA clones encoding proteins with homology to KASII in cotton were identified and isolated from a developing cottonseed cDNA library (Example 1) as follows. A PCR fragment corresponding to approximately 400 bp of the protein coding region of the *Arabidopsis* gene encoding KASII (Accession number: AF318307) was amplified using forward and reverse primers: 5'-ATGGTGG GTGCGTCTTCCTCTT-3' (SEQ ID NO: 17) and 5'-CACTACAACATAGAAGGTAT-GTG-3' (SEQ ID NO: 18) and template DNA obtained from *Arabidopsis* plants. The PCR fragment was labelled and used to probe the cDNA library under high stringency and two different KASII-like cDNAs were isolated. These were designated ghKASII-A and ghKASII-B. It appeared that the ghKASII-B sequence was a full length cDNA as it had untranslated regions at both 5' and 3' ends. However, the ghKASII-A sequence had an additional 270 coding nucleotides at its 5' end and therefore it was likely that the 5' coding sequence was not complete. The ghKASII-A cDNA was 1997 bp long (SEQ ID NO: 1) and encoded a predicted protein of 522 amino acids (SEQ ID NO: 2). The ghKASII-B cDNA was 1628 bp long (SEQ ID NO: 3) and encoded a predicted protein of 433 amino acids (SEQ ID NO: 4) which was presumed to include a signal peptide sequence used for translocation of the protein into the plastid.

The predicted amino acid sequences of ghKASII-A and ghKASII-B had 92% identity relative to the other. Because their 3'UTR sequences were quite different, it was thought that they were derived from two different genes belonging to a KASII gene family in cotton. ghKASII-A had about 80-85% identity to other KASII genes from other dicot plants, and about 70% identity to some other monocot KASII genes. FIGS. 3 and 4 show the nucleotide and predicted amino acid sequences of ghKAS-A and -B, respectively.

Example 3

Figure 5:
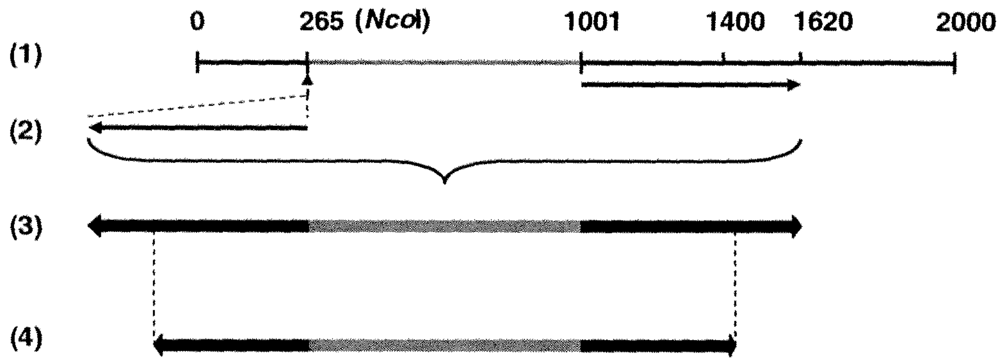
FIG. 5 is a schematic diagram showing the inverted repeat configuration of chimeric DNA to express a hairpin RNA for inhibition of the ghKASII-A gene. (1) The DNA sequence corresponding to nucleotides 1001 to 1620 of ghKASII-A (SEQ ID NO: 1) was (see 2) inserted at the NcoI site at nt 265 of ghKASII-A, in an antisense orientation thereby producing the inverted repeat (IR) structure as shown in (3), which was then truncated by PCR amplifying the first 400 bp of the repeated DNA sequences and the intervening 750 bp spacer, to create (4) the DNA sequence encoding the hairpin RNA molecule.
Figure 7:
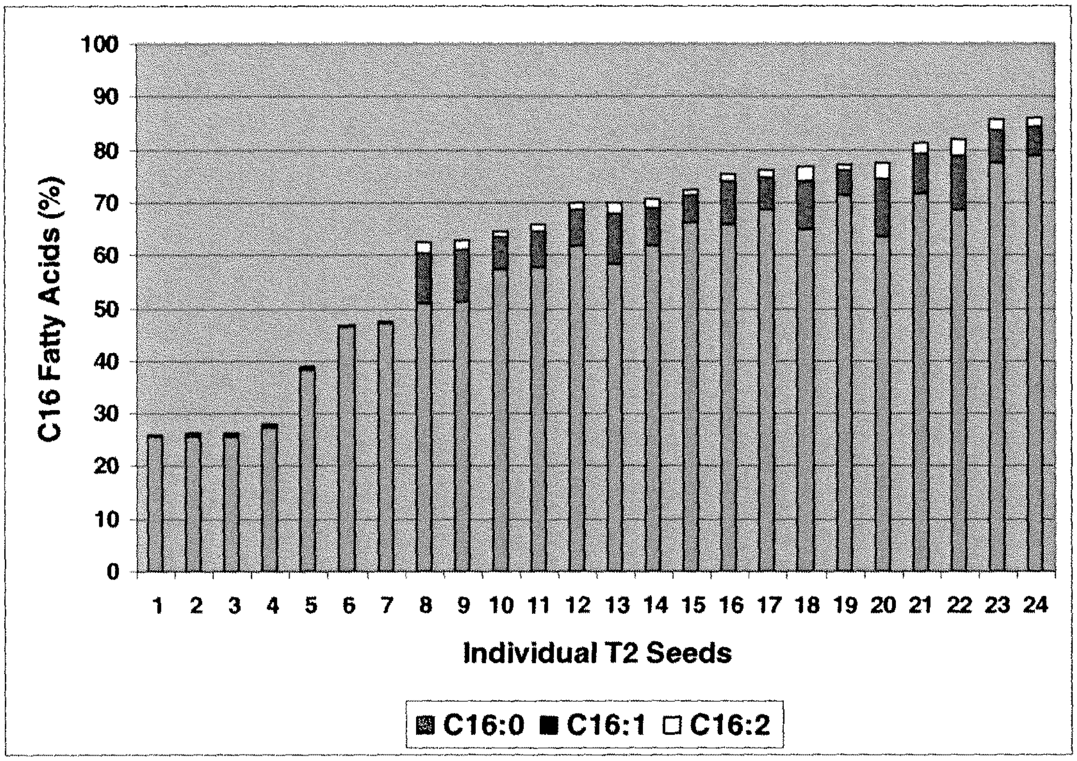
FIG. 7 is a representation of the C16 fatty acid composition of seedoil from T2 seeds. The percentage is shown of palmitic acid and its C16 derivative fatty acids (C16:1 and C16:2) in 24 individual $T_2$ seeds obtained from the primary ($T_1$) transgenic cotton line KIR-1. Seeds 1-4 appeared to be null segregants based on their C16:0 levels being the same as wild-type.

Design and Construction of a Chimeric DNA to Express a Hairpin RNA Molecule Targeting GHKASII-A A genetic construct to express a chimeric hairpin RNA molecule for RNAi mediated reduction of expression of the ghKASII-A of cotton was made as follows. The construct is shown schematically in FIG. 4 and contained an inverted repeat of the nucleotides from 1001 to 1400 of the ghKASII-A gene (SEQ ID NO: 1). A DNA fragment corresponding to nucleotides 1001 to 1620 of ghKASII-A was PCR amplified using the oligonucleotide primers: Nco-K10S: 5'-CCATGGCTAATCGC GATGGATTTGTCATGG-3' (SEQ ID NO: 19), and Nco-K10A: 5'-CCATGGCTCT-TCGGCCAAAT GTAAGAAA-3' (SEQ ID NO: 20) which incorporating NcoI restriction sites at both ends of the amplified fragment. The amplified PCR fragment was then inserted at the NcoI site at nucleotide position 265 of ghKASII-A, in an antisense orientation. Subsequently the first 400 bp of the inverted repeat units with the intervening 750 bp spacer were amplified by PCR using the primer Sma-KIR-SA: 5'-CCCGGGCGTATTGCCTGTACCGT TGC-3' (SEQ ID NO: 21) which was present in both inverted repeat units and with an additional SmaI site for facilitating the subsequent cloning. As a result of this cloning strategy, the inverted repeat units were separated by about 750 bp of sequence from the ghKASII-A gene. This spacer acted to stabilize the inverted repeat and thereby facilitate the cloning of the inverted repeat in the plasmid vector in *E. coli*. The sequence of the inverted repeat is shown in FIG. 5 (SEQ ID NO: 5).

To achieve seed specific expression, the inverted repeat sequence was placed under the control of a soybean lectin promoter (Lec-P) from the lec1 gene of soybean and a transcription terminator/polyadenylation sequence (Lec-T) (Cho et al., *Plant Molecular Biology Reporter* 13: 255-269, 1995). The hairpin RNA-expressing gene was positioned adjacent to the 3' end of a selectable marker gene which had an NPTII protein coding region driven by a nos promoter and nos3' transcription terminator/polyadenylation region.

Example 4

Transformation of Cotton with the KASII-A Silencing Construct

The KASII-A silencing construct inserted into a binary vector and introduced into *Agrobacterium tumefaciens* strain AGL1. The transformed bacteria were used to transform cotton variety Coker315 as described by Liu et al., *Plant Physiol.* 129: 1732-1743, 2002. Briefly, cotyledons excised from 10-days old aseptically-grown cotton seedlings were used as explants and were infected and co-cultivated with the *A. tumefaciens* transformants for a period of two days. This was followed by a six-week period of selection on MS medium (Murashige and Skoog, *Physiologia Plantarum.* 15: 473-497, 1962) containing 0.1 mg/l 2,4-D, 0.1 mg/l kinetin, 50 mg/l kanamycin sulphate, and 25 mg/l cefotaxime. Healthy calli derived from the cotyledon explants were then transferred to MS medium containing 5 mg/l 6-(γ,γ-dimethylallylamino)-purine (2ip), 0.1 mg/l naphthalene acetic acid (NAA), 25 mg/l kanamycin, and 250 mg/l cefotaxime for a second period of six weeks at 28° C. Somatic embryos started to form after about six to ten weeks of incubation and were transferred to fresh plates, but without added phytohormone or antibiotics, until they germinated. Plantlets that developed from the somatic embryos were subsequently transferred to soil and maintained in a glasshouse once leaves and roots were developed, with 28/20° C. (day/night) growth temperature.

Example 5

Phenotypic Analysis of Cotton Transformants

Four independent cotton lines transformed with the KASII-A silencing construct were regenerated and grown to maturity. No obvious phenotypic differences were observed between the transgenic and non-transgenic parental plants except that two of the four lines were male sterile, possibly due to side effects of prolonged tissue culture. The two male-fertile lines, KIR-1 and KIR-10, produced normal sized seeds.

A portion consisting of about ⅛ of the cotyledons of the mature seeds was excised from $T_2$ seeds obtained from the primary $T_1$ transgenic plants and each portion subjected to of fatty acid composition analysis by fatty acid methylester analysis (FAME) and gas chromatography-mass spectrometry (GC-MS). Total lipids were isolated using the method of Bligh et al., *Canadian Journal of Biochemistry and Physiology* 37: 911-917, 1959 and fatty acid methylesters (FAMEs) were prepared using standard methods as described by Liu et al., 2002 (supra). FAMEs were subsequently separated by gas chromatography (GC), using an Agilent 6890 GC fitted with a forte GC capillary column (30 m×0.25 mm). Fatty acids were identified by reference to FAME standards.

FIG. 6 shows the C16 fatty acid composition of seedoil from cotyledons of 24 randomly selected individual $T_2$ seeds in line KIR-1. Four seeds had C16 fatty acid composition similar to the non-transformed control plants and were presumed to be null segregants. This correlated with the absence of the transgene in these seed. The levels of palmitic acid and its derived C16 fatty acids in the other 20 seeds were increased, with the majority of seeds having palmitic acid levels exceeding 50% of the total fatty acid in the oil. The C16-derived fatty acids C16:1 (palmitoleic acid) and C16:2 were also increased, mostly in palmitoleic acid (C16:1) and to a lesser extent C16:2. The total percentage of C16 fatty acids reached a remarkable level of at least 85% of the total fatty acids. Palmitoleic acid and C16:2 were raised to at least 11.0% and 3.3% of total fatty acids, respectively, in some seed. Interestingly, the level of accumulation of the unsaturated C16 fatty acids was not strictly correlated with the level of palmitic acid. For example, the highest palmitic acid level observed, 78.7%, was found in a seed with 7.3% total unsaturated C16 fatty acids. This is in contrast to another individual seed containing 50.7% palmitic acid and 11.8% unsaturated C16 fatty acids.

The fatty acid composition for all major fatty acids is given in Table 1 for the 24 $T_2$ seeds from line KIR-1. In all seeds with increased percentages of palmitic and palmitoleic acids, the C18 fatty acids including stearic, oleic and linoleic acids were all reduced. Oleic acid was reduced in some seed to below 2%. There was a trend among the seedoils for increased levels of the fatty acid C18:1n-7 which is the elongation product of palmitoleic acid.

Figure 8:
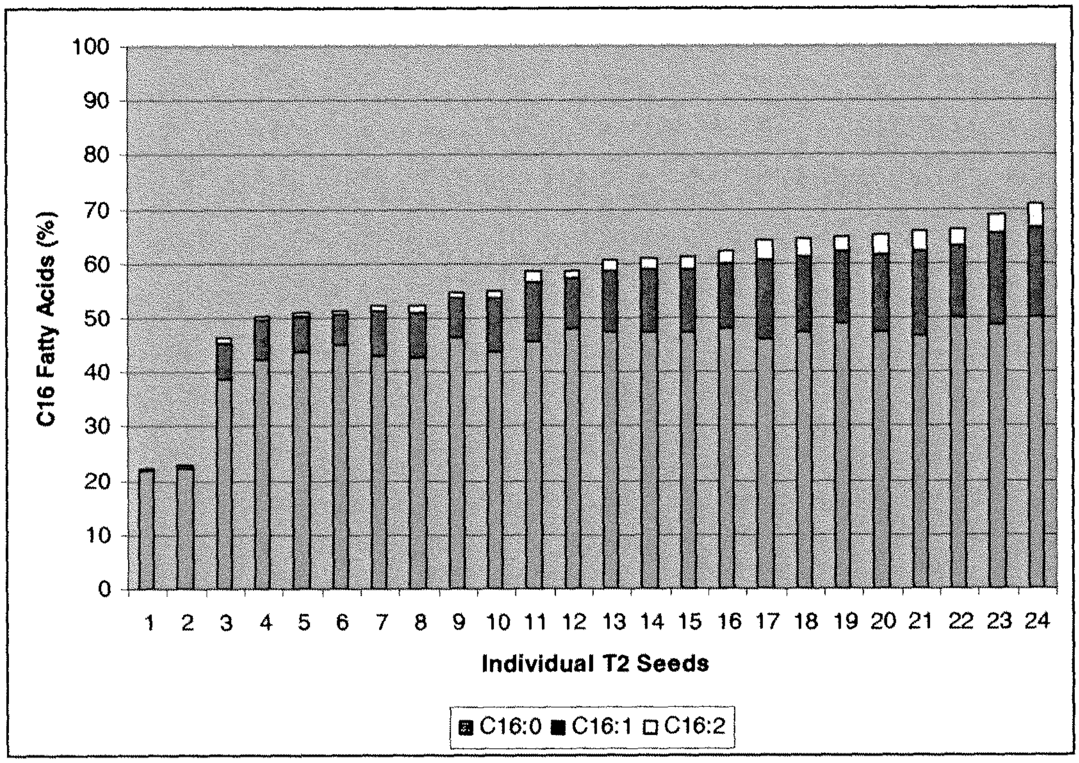
FIG. 8 shows the percentage of palmitic acid and its unsaturated C16 derivative fatty acids in 24 randomly selected individual $T_2$ seeds obtained from plant KIR-10.

In addition to KIR-1, mature $T_2$ seeds obtained from the second fertile cotton plant, KIR-10, were also analysed for the fatty acid composition. FIG. 8 shows the percentage of palmitic acid and its unsaturated C16 derivative fatty acids in 24 randomly selected individual $T_2$ seeds obtained from plant KIR-10. The first two seeds were obviously null segregants. This proportion of nulls (2/24) suggested that the transgenic plant KIR-10 contained more than one transgene. Palmitic acid levels in the other seeds were increased to between 39% and 50% of total fatty acids in the oil. This extent of increase in palmitic acid in seeds from KIR-10 was less than in seeds from KIR-1. In KIR-10, the C16 unsaturated fatty acids palmitoleic acid (C16:1) and C16:2 were also increased from normally low amounts to as high as 20.7%. The total amount of C16 unsaturated fatty acids in KIR-10 seedoil tended to be higher compared to KIR-1 seedoil, even though levels of palmitic acid were lower in KIR-10. Furthermore, levels of palmitic acid and its derivative unsaturated C16 fatty acids were better correlated in KIR-10 seed. As for KR-1, the increase in levels of C16 fatty acids was at the expense of C18 fatty acids, except for the C18:1n-7 which was the elongation product of palmitoleic acid. The fatty acid composition of the 24 $T_2$ seeds for KIR-10 is tabulated in Table 2.

Fatty Acid Composition of Seedoil of Progeny Plants

The inheritance and stability of the high-palmitic trait in further generation/progeny seeds of line KIR-10 was assessed. Eight $T_2$ seeds with raised palmitic acid were germinated and grown into mature $T_2$ plants. Approximately 15 mature $T_3$ seeds obtained from each of these $T_2$ plants were harvested and subjected to analysis of fatty acid composition. C16 fatty acids including palmitic acid and its derived palmitoleic acid and C16:2 of $T_3$ seeds derived from four representative $T_2$ lines were elevated to the same extent as in the previous generation. Palmitic acid levels were increased to between 40 to 50% of total fatty acids. Three of the lines showed no null segregants, showing uniformly increased palmitic acid levels and were presumed to be homozygous for the transgene. This correlated with uniform presence of the transgene.

These data clearly demonstrated that targeting the ghKASII-A gene with a silencing construct enabled increased palmitic acid in the seedoil in cotton, from which it was concluded that ghKASII-A was the gene that should be targeted in cotton. The increased C16 fatty acids in the transgenic cotton was stably inherited correlated with the presence of the transgene.

Example 6

Inactivating Other Genes in Addition to KASII

In order to exemplify the inactivation of other oil biosynthesis genes in addition to that encoding KASII and determine the effect of the combination on the seed oil composition, the $T_2$ plant of KIR-10 was crossed with a cotton plants homozygous for a second transgene.

Inactivation of ghSAD-1 in Addition to ghKASII-A

Transgenic cotton plants designated "HS" contained a transgene expressing an inhibitor of expression of the ghSAD-1 gene, encoding Δ9-desaturase. When expressed, this transgene by itself elevated stearic acid levels in addition to a decrease in palmitic acid levels (Liu et al., 2002 (supra); WO2001/79499, both herein incorporated by reference). The KIR-10 $T_2$ plant was used as a pollen donor in a cross with a plant of the transgenic line HS-35 as the female parent. As before, an approximately ⅛ portion of the cotyledons was excised from each individual mature $F_1$ hybrid seed and seed-oil extracted from each subjected to GC analysis for fatty acid composition, while the remaining part of each seed with intact embryo axis was germinated and allowed to grow to maturity. The fatty acid composition of the cotyledon portions of the $F_1$ hybrid seeds derived from the crosses between KIR-10 and HS-35 are shown in Table 3.

As shown in Table 3, the $F_1$ hybrid seeds derived the cross between the KIR-10 $T_2$ plant and the high-stearic line, HS-35, showed a new phenotype which included both increased palmitic acid and stearic acid levels. Six out of the 15 sampled seeds showed similar fatty acid composition to the female parent, HS-35. It was concluded that those seeds did not contain the KASII-A silencing transgene. This indicated that the KIR-10 $T_2$ plant which provided the pollen in the cross was heterozygous for the KASII-A silencing transgene. In the other nine seeds, palmitic acid levels in the seedoil were increased to a similar level as in the KIR-10 $T_2$ parent and the stearic acid levels were increased 2.5 to 5-fold. However, the stearic acid level in these seeds was much lower than that in the HS-35 parent without the KASII-A silencing construct. This indicated that stearic acid in the F1 seed was still being converted efficiently to linoleic acid even in the presence of the SAD-1 silencing construct, although not as efficiently as in the wild-type seed.

Inactivation of ghFAD2-1 in Addition to ghKASII-A

Four different FAD2 genes have been isolated from cotton, each encoding possible microsomal oleoyl-Δ12 desaturases which could desaturate oleic acid to linoleic acid (Liu et al., 1999a (supra); Liu et al., 1999b (supra); Kargiotidou et al., *Journal of Experimental Botany* 2008 59(8): 2043-2056, 2008, both herein incorporated by reference). A first gene, designated ghFAD2-1, was specifically expressed in developing seeds at about the same time as active oil biosynthesis (Liu et al., 1999a (supra)). Two nucleotide sequences for ghFAD2-1 are presented herein (SEQ ID Nos: 6 and 8, encoding amino acid sequences SEQ ID Nos: 7 and 9) which are 96% identical along their full lengths and therefore probably represent cDNAs corresponding to either different alleles or more likely the homoeologous FAD2-1 genes in the tetraploid cotton. A second gene, ghFAD2-2, (Accession No. Y10112) had a low level constitutive expression and was expressed at a low level throughout seed development (Pirtle et al., 2001 (supra)). The nucleotide sequence of ghFAD2-2 is about 72% identical to the central half of ghFAD2-1. The third and fourth members ghFAD2-3 (Accession No. AF331163) and ghFAD2-4 (Accession No. AY279314) appeared to be expressed more highly in leaves and other cotton tissues rather than seeds (Kargiotidou et al., 2008 (supra)). ghFAD2-3 and ghFAD2-4 have nucleotide sequences which are about 72% identical to ghFAD2-1.

Based on these observations and the previous production of high-oleic cottonseed oil by RNAi down-regulation of ghFAD2-1 (Liu et al., 2002 (supra); U.S. Pat. No. 6,974,898), this gene was thought to encode the major FAD2 activity in cotton seeds. A region of the ghFAD2-1 gene having the sequence of nucleotides 5-354 of SEQ ID NO: 6 was selected to make an RNAi construct for down-regulation of the gene (Liu et al., 2002 (supra)) and was designed to be specific for ghFAD2-1. U.S. Pat. No. 6,974,898 used a 92 bp region from the 5'-UTR of ghFAD2-1, and Liu et al., 2002 (supra), also used a 540 bp region from the 5' end of the transcribed part of the gene. Transgenic cotton plants designated "HO" contained the hairpin RNA-expressing transgene expressing an inhibitor of expression of the ghFAD2-1 gene, encoding Δ12-desaturase. When expressed, this transgene by itself elevated oleic acid levels, primarily by blocking conversion to linoleic acid, in addition to a decrease in palmitic acid levels (Liu et al., 2002 (supra); WO2001/79499).

A KIR-10 $T_2$ plant produced as described above was used as a pollen donor in a cross with a plant of the transgenic line HO-30 as the female parent. As before, a ⅛th portion of the cotyledons was excised from each individual mature $F_1$ hybrid seed and seedoil extracted from each subjected to GC analysis for fatty acid composition, while the remaining part of each seed with intact embryo axis was germinated and allowed to grow to maturity. The fatty acid composition of the cotyledon portions of the $F_1$ hybrid seeds derived from the crosses between KIR-10 and HS-30 are shown in Table 4.

As shown by the data in Table 4, the F1 hybrid seeds from the cross between the KIR-10 plant and the high-oleic plant, HO-30, showed both elevated palmitic and oleic acid levels in the seedoil. Twelve out of the fourteen $F_1$ seeds sampled in the Table 4 showed the increase of both fatty acids in the oil, while the other two seeds showed the same oil composition as the female parent, HO-30. These two seeds were presumed to be null for the KASII-A silencing transgene. In the other 12 seeds, the average levels of palmitic and oleic acid in the seedoil were 41% and 37%, respectively. Similar to the KIR-10 $T_2$ parent, the palmitoleic acid levels in these F1 seeds were also increased to an average of 12%. The linoleic acid remained at a low level similar to that in the HO parent. It was concluded that it was possible to raise both palmitic and oleic acid levels in the seed oil by using the combination of silencing constructs.

Inactivation of ghSAD-1 and ghFAD2-1 in Addition to ghKASII-A

The KIR-10 plant was crossed with a homozygous HO/HS cotton plant, HO/HS-9. The HO/HS-9 plant was produced by previously crossing HO-30 and HS-35 plants and subsequently selecting progeny that were homozygous for both the HO and HS transgenes. The HO/HS-9 plant had elevated levels of both oleic and stearic acids as a result of simultaneous silencing of ghFAD2-1 and ghSAD-1 in a seed-specific manner The KIR-10 $T_2$ plant was used as the pollen donor and HO/HS-9 plant as the female parent. As before, an ⅛th portion of each cotyledon was excised from individual mature $F_1$ hybrid seeds and extracted seedoil was subjected to GC analysis for fatty acid composition, while the remaining portions of the seeds with intact embryo axis were germinated and plants grown to maturity. The fatty acid composition of the oil from the cotyledon portions of the $F_1$ hybrid seeds derived from the crosses between KIR-10 and HO/HS-9 are shown in Table 5.

Among the 44 sampled individual F1 seeds, five appeared to be null for the KASII-A silencing transgene (PSO_1, 25, 27, 36, 42). The other 39 seeds showed increased levels of both palmitic and oleic acid as provided by the parents, in addition to moderate increases in stearic acid levels which averaging 3.4%, i.e. 2-3-fold increased compared to wild-type cottonseed oil. Linoleic acid levels were low, about 5%, a similar level as in the crosses between the KASII-A silenced plant and the FAD2-1 silenced plant. The palmitoleic acid level in the seed with the three constructs was increased to 5.8% on average. These data showed that it was possible to simultaneously increase palmitic acid, oleic acid and stearic acid levels in the seedoil.

Example 7

Cloning of Genes Encoding Cyclopropane Fatty Acid Synthase (CPA-FAS) in Cotton CPA-FAS catalyses the first committed step in production of cyclopropane fatty acids, the conversion of oleic acid to DHS. Two EST sequences from *G. hirsutum* were identified as being differentially expressed after infection of cotton roots and hypocotyls with *Fusarium oxysporeum* (Dowd et al., *Molecular Plant-Microbe Interactions.* 17: 654-667, 2004). One of the EST sequences, CD486555, was used as a DNA probe to screen the cDNA library made from developing cottonseed (Example 1) and a second cDNA library made from RNA obtained from cotton roots. The DNA sequence of the probe DNA is given in SEQ ID NO: 10.

After high stringency hybridization with the probe, two different full length cDNAs with unique 5' and 3' UTR sequences were isolated from the cDNA library made from cotton root RNA. A third cDNA clone was isolated from the cottonseed cDNA library. They were designated as ghCPA-FAS-1, 2 and -3 respectively. The DNA sequences and the predicted amino acid sequences of the encoded polypeptides are given in SEQ ID NO: 11-16.

The deduced ghCPA-FAS polypeptides each comprised 865-873 amino acids and had calculated molecular masses of approximately 99 kDa. This probably represented the mature protein since CPA-FAS enzyme, being active in the ER, was not expected to have a 5' signal peptide. Similarly to CPA-FAS from *Sterculia foetida* and the homologous proteins from *Arabidopsis* (Accession No. AT23510) and rice (AK069115) predicted from genomic sequences, the encoded ghCPA-FAS proteins had an N-terminal FAD-binding domain fused to a C-terminal domain which had homology to various methyltransferases. This was consistent with predicted CPA-FAS activity of the proteins. At the N-terminus, the first 20 amino acids of the ghCPA-FAS proteins appeared to be hydrophobic and were thought to be involved in membrane anchoring.

When the deduced amino acid sequences of the three different ghCPA-FAS cDNAs were compared with homlogous DNA sequences from *Sterculia foetida, Arabidopsis* and rice, it was observed that ghCPA-FAS-1 (AY574036) and ghCPA-FAS-2 (AY574037) shared 97% amino acid identity, but only 64-65% identity to ghCPA-FAS-3 (AY574038). In contrast, ghCPA-FAS-3 showed higher sequence homology with each of the *Arabidopsis* genes—74% amino acid identity with At23510, and 75% amino acid identity with At23530. This suggested that ghCPA-FAS-3 evolved separately before cotton speciation. *Arabidopsis* and rice are not known to accumulate CPA or CPE fatty acids and therefore the functionality of the CPA-FAS genes in these plants is investigated.

The genomic organization of CPA-FAS genes in cotton was investigated by Southern blot hybridization analysis using the protein coding region of ghCPA-FAS-1 as a probe. At least three hybridizing bands were detected in HindIII digested DNA from diploid cottons, while there were twice as many hybridizing bands in tetraploid cottons. It was concluded that each of the three ghCPA-FAS genes were represented by a single locus in diploid *Gossypium* and two homoeologous loci in tetraploid cottons. This demonstrated that allotetraploid cotton contained two copies of each of the three genes present in the A- and D-genome diploid progenitors.

Expression of the cotton CPA-FAS genes were analysed, looking for differentially expression in cotton tissues. Total RNA was extracted from various cotton tissues including roots, hypocotyls, leaves and developing embryos at various times after anthesis and analysed in Northern blot hybridization experiments. This revealed that the ghCPA-FAS-1 transcript level was high in roots and hypocotyls, but not detected in leaves and developing embryos, while ghCPA-FAS-2 expression was detected in all tissues examined except the leaves. In the developing embryos, maximal transcript levels of ghCPA-FAS-2 were found in embryos during the middle part of seed development, from approximately 20-40 days after anthesis. This was the main time period for oil production in developing cotton embryos. It was therefore predicted that ghCPA-FAS-2 played a key role in determining the biosynthesis of cyclopropenoid fatty acids in cottonseed and therefore was a candidate target gene for down-regulation to reduce CPA and CPE fatty acids in cottonseed oil.

Example 8

Genetic Construct to Simultaneously Down-Regulate GHFAD2-1, GHCPA-FAS-2 and GHFATB-1 in Cottonseed A genetic construct to express a chimeric hairpin RNA molecule for RNAi mediated reduction of gene expression was made as follows. The RNAi gene silencing construct was designed to simultaneously target three different genes with the goal of achieving significant reductions in cyclopropane fatty acids in combination with significantly increased oleic acid in cottonseed oil. The construct contained an inverted repeat of a chimeric sequence made from 350 bp of ghFAD2-1, 442 bp of ghCPA-FAS-2 and 358 bp of ghFatB-1 fused together. The inverted repeat units of this chimeric sequence were separated by Intron I from the ghFad2-1 gene, which was 1120 bp long, with intact 5' and 3' exon/intron boundaries. The intron acted as a spacer to stabilize the inverted repeat and thereby facilitate the cloning of the inverted repeat in the plasmid vector in *E. coli*. To achieve seed specific expression, the inverted repeat sequence was placed under the control of a soybean lectin promoter (Lec-P) and a transcription terminator/polyadenylation sequence (Lec-T) (Cho et al., 1995 (supra)). The hairpin RNA-expressing gene was positioned adjacent to the 3' end of a selectable marker gene comprised of an NPTII protein coding region driven by the sub-clover stunt virus promoter (Sc1-F) and terminator (Sc3-T). This genetic construct was named the MonoCott construct.

The MonoCott genetic constructs was inserted into a binary vector and introduced into *Agrobacterium tumefaciens* strain AGL1. The transformed bacteria were used to transform cotton variety Coker315 as described above. Six independent cotton lines transformed with the MonoCott RNAi construct were regenerated from calli and allowed to grow to maturity in the greenhouse, flowering and producing seed as normal. No obvious phenotypic differences were observed between the transgenic plants and the non-transgenic (wild-type) parental plants of the variety Coker315.

When seedoil from seeds of one transgenic line transformed with the MonoCott construct was analysed by FAME and GC-MS, the oil had a fatty acid composition having a markedly increased level of oleic acid, in combination with reduced cyclopropane fatty acid levels in the embryo axes. The cyclopropane fatty acids, including DHS, STC and MVL are not present at significant levels in cotton cotyledons in mature cottonseed, but rather are concentrated in the embryo axes of the mature seeds. Non-transformed cotton embryo axes, as represented by the untransformed Coker315, contained total cyclopropane fatty acids at a level of 11.5% of total fatty acids (average of 23 randomly sampled seeds). In oil from embryo axes of the seed transformed with the MonoCott construct, there was a substantial reduction in all three cyclopropane fatty acids with total cyclic fatty acid level averaging only 3.8% in 26 randomly selected seeds. This represented a reduction of total cyclopropane fatty acids more than 60% compared to wild-type and more than 80% compared to high-oleic transgenic seed. The resultant level of cyclopropane fatty acids in the seedoil from the whole cottonseed of the transgenic lines was in the range of 0.1% to 0.5%. These data showed that the ghCPA-FAS-2 gene encoded the major CPA-FAS enzyme in cottonseed and that silencing this gene was effective to substantially reducing cyclopropane fatty acids in cottonseed oil.

The same region of the ghCPA-FAS-2 gene can be used to produce a hairpin RNA silencing construct, which can be used to produce transgenic cotton plants. These plants can be crossed with the KIR-1 and KIR-10 plants described above, having high palmitic acid levels, to produce cottonseed oil with reduced levels of cyclopropane fatty acids in addition to high levels of palmitic acid. Alternatively, a single construct to express a hybrid hairpin RNA molecule can be produced, to simultaneously down-regulate the KASII-A and CPA-FAS-2 genes.

Example 9

Isolation or Identification of KASII Genes from Other Sources

The cotton KASII-A sequence can be used to isolate KASII encoding nucleic acid sequences from other plant species, fungal species or other organisms. DNA probes can be prepared as described in Example 2 and used to probe cDNA libraries prepared from developing seeds of the plant species of interest, preferably from an oilseed crop plant, or to genomic DNA libraries. Alternatively, PCR using degenerate primers designed to hybridize to conserved regions of the KASII genes can be used in PCR or RT-PCR amplification reactions to isolate the corresponding regions from KASII genes from other plant species. The conserved regions can be identified by comparison of the KASII sequences disclosed herein with the *Arabidopsis* sequence (Accession number: AF318307) or other sequences in databases. Table 8 sets out a list of sequences (each Accession No/sequence herein incorporated by reference) identified from a sequence database using the program BLAST as having significant identity over a reference region to KASII-A in SEQ ID NO: 1.

Homologous silencing constructs for other oilseed crop plants can be prepared based on the KASII sequences isolated by such approaches, in an analogous fashion to the cotton KASII-A silencing construct described above.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Fatty acid composition in seed oil from 24 individual seeds obtained from a primary transgenic cotton line (KIR-1).

| Sample | C14:0 | C16:0 | C16:1 | C16:2 | C18:0 | C18:1 (n-9) | C18:1 (n-7) | C18:2 | C18:3 | C20:0 |
|---|---|---|---|---|---|---|---|---|---|---|
| KIR-1_1 | 0.6 | 25.4 | 0.5 | 0.0 | 2.1 | 11.1 | 0.7 | 58.9 | 0.1 | 0.2 |
| KIR-1_2 | 1.0 | 25.6 | 0.6 | 0.0 | 1.9 | 12.2 | 0.8 | 57.3 | 0.1 | 0.3 |
| KIR-1_3 | 0.7 | 25.8 | 0.5 | 0.0 | 2.2 | 11.1 | 0.7 | 58.5 | 0.1 | 0.3 |
| KIR-1_4 | 0.7 | 27.4 | 0.5 | 0.0 | 2.3 | 10.9 | 0.7 | 57.1 | 0.1 | 0.3 |
| KIR-1_5 | 0.9 | 38.3 | 0.6 | 0.0 | 2.2 | 9.3 | 0.7 | 47.4 | 0.1 | 0.3 |
| KIR-1_6 | 0.6 | 46.4 | 0.3 | 0.0 | 4.9 | 8.0 | 0.4 | 38.7 | 0.0 | 0.5 |
| KIR-1_7 | 0.7 | 46.9 | 0.4 | 0.0 | 4.0 | 8.0 | 0.5 | 38.7 | 0.0 | 0.5 |
| KIR-1_8 | 0.2 | 50.7 | 9.7 | 2.0 | 1.0 | 2.6 | 1.7 | 31.4 | 0.2 | 0.3 |
| KIR-1_9 | 0.2 | 51.4 | 9.6 | 2.0 | 1.0 | 2.7 | 1.7 | 30.8 | 0.1 | 0.2 |
| KIR-1_10 | 0.3 | 57.3 | 6.2 | 0.9 | 1.1 | 3.6 | 1.3 | 28.5 | 0.1 | 0.3 |
| KIR-1_11 | 0.2 | 57.5 | 7.0 | 1.2 | 1.2 | 2.6 | 1.5 | 28.0 | 0.1 | 0.3 |
| KIR-1_12 | 0.3 | 58.5 | 9.4 | 2.0 | 1.1 | 2.0 | 1.3 | 24.5 | 0.2 | 0.3 |
| KIR-1_13 | 0.3 | 61.8 | 7.3 | 1.5 | 1.1 | 2.2 | 1.2 | 24.1 | 0.0 | 0.3 |
| KIR-1_14 | 0.2 | 61.9 | 6.7 | 1.3 | 1.1 | 2.2 | 1.2 | 24.7 | 0.1 | 0.3 |
| KIR-1_15 | 0.2 | 63.3 | 11 | 3.3 | 1.2 | 1.1 | 1.5 | 17.5 | 0.1 | 0.3 |
| KIR-1_16 | 0.1 | 65.0 | 9.2 | 2.7 | 1.1 | 1.1 | 1.5 | 18.5 | 0.1 | 0.3 |
| KIR-1_17 | 0.2 | 66.0 | 7.9 | 1.6 | 1.2 | 1.7 | 1.1 | 19.5 | 0.1 | 0.3 |
| KIR-1_18 | 0.2 | 66.1 | 5.4 | 1.0 | 1.2 | 2.3 | 1.1 | 21.9 | 0.1 | 0.3 |
| KIR-1_19 | 0.2 | 68.5 | 6.2 | 1.2 | 1.1 | 1.6 | 1.0 | 19.3 | 0.1 | 0.3 |
| KIR-1_20 | 0.2 | 68.6 | 10.1 | 3.1 | 1.1 | 1.0 | 1.2 | 13.9 | 0.1 | 0.3 |

Seeds KIR-1_1 to 4 were null segregates based on their having essentially wild-type composition.

TABLE 2

Fatty acid composition in seedoil from 24 individual $T_2$ seeds from the transgenic cotton plant KIR-10.

| Sample | C14:0 | C16:0 | C16:1 | C16:2 | C18:0 | C18:1 (n-9) | C18:1 (n-7) | C18:2 | C18:3 | C20:0 |
|---|---|---|---|---|---|---|---|---|---|---|
| KIR-10_1 | 0.6 | 21.7 | 0.5 | 0.0 | 1.8 | 14.5 | 0.8 | 59.6 | 0.1 | 0.2 |
| KIR-10_2 | 0.6 | 22.3 | 0.5 | 0.0 | 1.8 | 13.3 | 0.8 | 60.1 | 0.1 | 0.2 |
| KIR-10_3 | 0.2 | 38.8 | 6.5 | 0.8 | 0.9 | 5.9 | 1.7 | 44.8 | 0.1 | 0.2 |
| KIR-10_4 | 0.3 | 42.3 | 7.3 | 0.8 | 0.9 | 5.3 | 1.6 | 41.0 | 0.1 | 0.2 |
| KIR-10_5 | 0.2 | 42.8 | 8.2 | 1.4 | 0.8 | 4.1 | 1.7 | 40.2 | 0.2 | 0.2 |
| KIR-10_6 | 0.2 | 43.1 | 8.1 | 1.0 | 1.0 | 5.6 | 1.7 | 38.8 | 0.1 | 0.2 |
| KIR-10_7 | 0.2 | 43.7 | 9.8 | 1.5 | 0.8 | 4.1 | 1.7 | 38.0 | 0.2 | 0.0 |
| KIR-10_8 | 0.3 | 43.8 | 6.3 | 0.7 | 1.0 | 5.6 | 1.5 | 40.3 | 0.1 | 0.2 |
| KIR-10_9 | 0.3 | 45.0 | 5.8 | 0.6 | 1.1 | 6.3 | 1.5 | 38.6 | 0.1 | 0.2 |
| KIR-10_10 | 0.2 | 45.8 | 10.8 | 1.9 | 0.9 | 3.9 | 1.7 | 34.2 | 0.1 | 0.2 |
| KIR-10_11 | 0.1 | 46.2 | 14.4 | 3.8 | 0.8 | 2.3 | 2.1 | 29.5 | 0.2 | 0.2 |
| KIR-10_12 | 0.2 | 46.4 | 7.5 | 0.9 | 1.0 | 4.5 | 1.5 | 37.4 | 0.1 | 0.2 |
| KIR-10.13 | 0.1 | 46.7 | 15.5 | 3.6 | 0.8 | 2.2 | 2.1 | 28.4 | 0.2 | 0.2 |
| KIR-10_14 | 0.2 | 47.2 | 11.8 | 2.3 | 0.9 | 3.1 | 1.7 | 32.2 | 0.2 | 0.2 |
| KIR-10_15 | 0.2 | 47.3 | 11.3 | 2.0 | 0.9 | 3.3 | 1.7 | 32.7 | 0.1 | 0.2 |
| KIR-10_16 | 0.1 | 47.4 | 14.2 | 3.6 | 0.8 | 2.2 | 2.0 | 28.9 | 0.1 | 0.2 |
| KIR-10_17 | 0.2 | 47.5 | 13.8 | 3.2 | 0.9 | 2.7 | 1.8 | 29.3 | 0.2 | 0.2 |
| KIR-10_18 | 0.2 | 47.5 | 11.3 | 2.2 | 1.1 | 3.6 | 1.7 | 31.7 | 0.1 | 0.2 |
| KIR-10_19 | 0.2 | 48.0 | 9.4 | 1.3 | 0.9 | 3.7 | 1.5 | 34.3 | 0.1 | 0.2 |
| KIR-10_20 | 0.2 | 48.0 | 11.8 | 2.3 | 1.0 | 3.5 | 1.8 | 30.6 | 0.2 | 0.2 |
| KIR-10_21 | 0.1 | 48.7 | 16.8 | 3.4 | 0.9 | 2.3 | 1.9 | 25.1 | 0.2 | 0.2 |
| KIR-10_22 | 0.2 | 48.9 | 13.5 | 2.6 | 0.9 | 2.9 | 1.8 | 28.6 | 0.1 | 0.2 |
| KIR-10_23 | 0.2 | 50.0 | 13.4 | 2.8 | 0.9 | 2.2 | 1.6 | 28.2 | 0.2 | 0.2 |
| KIR-10_24 | 0.1 | 50.1 | 16.4 | 4.3 | 0.9 | 1.8 | 1.9 | 23.7 | 0.2 | 0.3 |

Seeds KIR-10_1 and 2 were null segregants based on their having essentially wild-type composition.

TABLE 3

Fatty acid composition in seedoil from 15 individual $F_1$ seeds from a cross between transgenic cotton plant KIR-10 and the high stearic line, HS-35.

| | C14:0 | C16:0 | C16:1 | C18:0 | 18:1 (n-9) | 18:1 (n-7) | C18:2 | C18:3 | C20:0 |
|---|---|---|---|---|---|---|---|---|---|
| PS_01 | 0.5 | 19.3 | 0.1 | 22.8 | 7.7 | 0.2 | 47.6 | 0.2 | 1.1 |
| PS_02 | 0.5 | 19.5 | 0.2 | 21.8 | 8.3 | 0.2 | 47.9 | 0.2 | 1.0 |
| PS_03 | 0.4 | 17.0 | 0.2 | 23.5 | 8.7 | 0.2 | 48.3 | 0.3 | 1.1 |
| PS_07 | 0.6 | 20.0 | 0.2 | 20.2 | 8.9 | 0.3 | 48.5 | 0.1 | 1.0 |
| PS_011 | 0.5 | 20.0 | 0.2 | 23.3 | 7.6 | 0.2 | 46.4 | 0.2 | 1.2 |
| PS_012 | 0.6 | 20.5 | 0.2 | 18.6 | 8.8 | 0.2 | 49.8 | 0.2 | 0.9 |
| PS_04 | 0.3 | 46.1 | 2.2 | 4.5 | 5.0 | 0.5 | 40.2 | 0.2 | 0.6 |
| PS_05 | 0.3 | 48.9 | 3.7 | 2.5 | 4.9 | 0.7 | 38.0 | 0.2 | 0.4 |
| PS_06 | 0.3 | 50.7 | 2.7 | 4.0 | 4.2 | 0.6 | 36.4 | 0.2 | 0.6 |
| PS_08 | 0.3 | 50.1 | 2.2 | 4.9 | 4.1 | 0.5 | 36.7 | 0.2 | 0.7 |
| PS_09 | 0.3 | 51.3 | 2.6 | 4.5 | 4.7 | 0.6 | 35.0 | 0.2 | 0.6 |
| PS_010 | 0.3 | 51.9 | 2.7 | 4.1 | 4.1 | 0.6 | 35.3 | 0.2 | 0.6 |
| PS_013 | 0.2 | 48.9 | 2.1 | 4.7 | 4.3 | 0.5 | 38.0 | 0.2 | 0.7 |
| PS_014 | 0.2 | 51.3 | 2.6 | 3.7 | 4.1 | 0.6 | 36.2 | 0.2 | 0.7 |
| PS_015 | 0.2 | 50.8 | 2.9 | 3.6 | 4.4 | 0.7 | 36.2 | 0.2 | 0.6 |

TABLE 4

Fatty acid composition in 14 individual $F_1$ seeds from a cross between transgenic cotton plant KIR-10 and the homozygous high oleic plant HO-30 line.

| | C14:0 | C16:0 | 16:1 | C18:0 | C18:1 n-9 | 18:1 n-7 | 18:2 | 18:3 | 20:0 |
|---|---|---|---|---|---|---|---|---|---|
| PO_2 | 0.5 | 17.0 | 0.7 | 1.9 | 73.1 | 0.9 | 4.9 | 0.1 | 0.3 |
| PO_7 | 0.6 | 17.0 | 0.7 | 1.7 | 74.3 | 0.9 | 4.0 | 0.1 | 0.3 |

TABLE 4-continued

Fatty acid composition in 14 individual $F_1$ seeds from a cross between transgenic cotton plant KIR-10 and the homozygous high oleic plant HO-30 line.

| | C14:0 | C16:0 | 16:1 | C18:0 | C18:1 n-9 | 18:1 n-7 | 18:2 | 18:3 | 20:0 |
|---|---|---|---|---|---|---|---|---|---|
| PO-1 | 0.2 | 41.0 | 12.4 | 1.3 | 36.9 | 1.8 | 5.4 | 0.1 | 0.4 |
| PO_3 | 0.2 | 38.6 | 10.7 | 1.4 | 39.3 | 1.8 | 7.0 | 0.2 | 0.3 |
| PO_4 | 0.2 | 38.7 | 11.7 | 1.2 | 39.9 | 1.9 | 5.5 | 0.2 | 0.3 |
| PO_5 | 0.2 | 42.1 | 16.1 | 1.2 | 32.0 | 1.8 | 5.7 | 0.2 | 0.3 |
| PO_6 | 0.2 | 42.8 | 13.6 | 2.0 | 33.3 | 1.8 | 5.2 | 0.1 | 0.4 |
| PO_8 | 0.2 | 38.5 | 10.3 | 1.6 | 40.9 | 1.9 | 5.6 | 0.2 | 0.3 |
| PO_9 | 0.2 | 45.1 | 11.1 | 2.4 | 33.8 | 1.7 | 4.5 | 0.1 | 0.4 |
| PO_10 | 0.2 | 41.1 | 12.5 | 1.8 | 35.4 | 1.8 | 6.2 | 0.2 | 0.3 |
| PO_11 | 0.2 | 37.5 | 10.9 | 1.2 | 40.2 | 1.8 | 7.2 | 0.2 | 0.3 |
| PO_12 | 0.2 | 40.9 | 12.9 | 1.3 | 35.6 | 1.9 | 6.3 | 0.2 | 0.3 |
| PO_13 | 0.2 | 38.6 | 10.3 | 1.3 | 39.3 | 1.8 | 7.4 | 0.2 | 0.3 |

TABLE 5

Fatty acid composition in 44 individual $F_1$ seeds from a cross between primary transgenic cotton plant KIR-10 and the homozygous HO/HS-9 line.

| | C14:0 | C16:0 | 16:1 | C18:0 | C18:1 n-9 | C18:1 n-7 | C18:2 | C18:3 | C20:0 |
|---|---|---|---|---|---|---|---|---|---|
| PSO_1 | 0.3 | 19.8 | 7.3 | 3.8 | 51.5 | 1.7 | 14.4 | 0.2 | 0.3 |
| PSO_2 | 0.2 | 49.6 | 7.5 | 2.8 | 31.0 | 0.9 | 6.4 | 0.2 | 0.7 |
| PSO_3 | 0.3 | 41.1 | 5.1 | 2.7 | 44.2 | 0.9 | 4.6 | 0.1 | 0.6 |
| PSO_4 | 0.3 | 41.9 | 4.3 | 3.6 | 43.3 | 0.8 | 4.6 | 0.1 | 0.7 |
| PSO_5 | 0.2 | 49.0 | 7.4 | 2.7 | 33.5 | 0.8 | 5.0 | 0.1 | 0.6 |
| PSO_6 | 0.2 | 44.1 | 6.1 | 2.7 | 39.6 | 0.9 | 4.9 | 0.1 | 0.6 |
| PSO_7 | 0.3 | 48.4 | 7.3 | 2.5 | 33.1 | 0.8 | 6.3 | 0.2 | 0.6 |
| PSO_8 | 0.2 | 40.9 | 4.1 | 4.0 | 44.1 | 0.7 | 4.6 | 0.1 | 0.7 |
| PSO_9 | 0.2 | 42.0 | 5.7 | 2.8 | 42.0 | 0.9 | 5.1 | 0.1 | 0.6 |
| PSO_10 | 0.3 | 46.3 | 8.3 | 2.2 | 35.5 | 1.0 | 5.4 | 0.1 | 0.5 |
| PSO_11 | 0.3 | 42.4 | 4.3 | 3.7 | 41.9 | 0.7 | 5.4 | 0.1 | 0.7 |
| PSO_12 | 0.2 | 45.6 | 5.9 | 2.8 | 38.1 | 0.8 | 5.2 | 0.1 | 0.6 |
| PSO_13 | 0.3 | 42.6 | 3.9 | 4.1 | 42.5 | 0.7 | 4.4 | 0.1 | 0.8 |
| PSO_14 | 0.2 | 45.1 | 4.8 | 3.6 | 39.3 | 0.7 | 4.8 | 0.1 | 0.7 |
| PSO_15 | 0.2 | 44.5 | 6.3 | 2.8 | 39.0 | 0.8 | 5.1 | 0.1 | 0.6 |
| PSO_16 | 0.2 | 46.6 | 6.0 | 3.0 | 37.3 | 0.9 | 4.6 | 0.1 | 0.7 |
| PSO_17 | 0.3 | 44.5 | 6.2 | 2.9 | 38.5 | 1.0 | 5.2 | 0.1 | 0.6 |
| PSO_18 | 0.2 | 47.1 | 6.8 | 2.5 | 36.7 | 0.9 | 4.8 | 0.0 | 0.6 |
| PSO_19 | 0.3 | 41.6 | 4.1 | 3.8 | 43.3 | 0.7 | 4.9 | 0.1 | 0.7 |
| PSO_20 | 0.2 | 40.1 | 3.7 | 4.2 | 44.7 | 0.7 | 5.0 | 0.1 | 0.8 |
| PSO_21 | 0.2 | 44.1 | 4.6 | 3.4 | 40.9 | 0.7 | 4.6 | 0.1 | 0.7 |
| PSO_22 | 0.2 | 35.7 | 3.1 | 4.5 | 47.9 | 0.8 | 6.1 | 0.2 | 0.8 |
| PSO_23 | 0.2 | 51.2 | 7.9 | 2.6 | 29.1 | 1.0 | 6.4 | 0.2 | 0.7 |
| PSO_24 | 0.2 | 48.6 | 8.4 | 2.3 | 32.0 | 1.1 | 6.1 | 0.2 | 0.6 |
| PSO_25 | 0.4 | 15.2 | 0.2 | 20.0 | 55.3 | 0.3 | 6.2 | 0.2 | 1.6 |
| PSO_26 | 0.2 | 39.5 | 3.7 | 4.0 | 45.1 | 0.8 | 5.2 | 0.1 | 0.8 |
| PSO_27 | 0.4 | 15.0 | 0.2 | 24.5 | 51.1 | 0.2 | 5.7 | 0.2 | 1.9 |
| PSO_28 | 0.3 | 36.7 | 3.7 | 3.9 | 47.0 | 0.8 | 5.9 | 0.2 | 0.8 |
| PSO_29 | 0.2 | 51.7 | 8.3 | 2.4 | 29.3 | 0.9 | 5.8 | 0.2 | 0.6 |
| PSO_30 | 0.2 | 39.1 | 2.0 | 7.6 | 42.5 | 0.5 | 5.9 | 0.2 | 1.2 |
| PSO_31 | 0.2 | 45.8 | 6.7 | 2.4 | 36.3 | 1.0 | 6.3 | 0.2 | 0.6 |
| PSO_32 | 0.2 | 49.3 | 9.1 | 2.0 | 31.0 | 1.1 | 5.9 | 0.2 | 0.6 |
| PSO_33 | 0.2 | 51.1 | 7.7 | 2.5 | 30.6 | 0.9 | 5.3 | 0.1 | 0.7 |
| PSO_34 | 0.2 | 36.4 | 2.3 | 6.7 | 45.8 | 0.6 | 6.0 | 0.2 | 1.1 |
| PSO_35 | 0.2 | 45.1 | 4.3 | 3.7 | 38.1 | 0.8 | 6.0 | 0.2 | 0.8 |
| PSO_36 | 0.4 | 15.1 | 0.2 | 20.8 | 54.7 | 0.3 | 6.0 | 0.2 | 1.6 |
| PSO_37 | 0.2 | 51.1 | 8.2 | 2.6 | 29.3 | 1.0 | 5.8 | 0.2 | 0.7 |
| PSO_38 | 0.2 | 47.9 | 6.0 | 3.0 | 35.2 | 0.9 | 5.2 | 0.1 | 0.8 |
| PSO_39 | 0.2 | 49.1 | 7.7 | 2.6 | 31.1 | 1.0 | 6.9 | 0.2 | 0.6 |
| PSO_40 | 0.2 | 42.6 | 2.7 | 7.5 | 43.8 | 0.6 | 0.2 | 0.3 | 1.2 |
| PSO_41 | 0.2 | 43.1 | 5.6 | 3.6 | 44.7 | 1.0 | 0.2 | 0.2 | 0.8 |
| PSO_42 | 0.4 | 16.0 | 0.3 | 18.0 | 62.4 | 0.4 | 0.2 | 0.2 | 1.5 |
| PSO_43 | 0.2 | 40.1 | 3.1 | 5.2 | 43.3 | 0.7 | 5.7 | 0.2 | 0.9 |
| PSO_44 | 0.2 | 51.5 | 11.2 | 2.1 | 32.4 | 1.2 | 0.0 | 0.2 | 0.5 |

TABLE 6

| Summary of sequence identifiers | |
|---|---|
| SEQUENCE ID NO: | DESCRIPTION |
| 1 | cDNA sequence of ghKASII-A, 1997 nucleotides, protein coding region: nucleotides: 1-1569 |
| 2 | amino acid sequence of ghKASII-A encoded by SEQ ID NO: 1 |
| 3 | cDNA sequence of ghKASII-B, 1628 nucleotides, protein coding region: 41-1342 |
| 4 | amino acid sequence of ghKASII-B encoded by SEQ ID NO: 3 |
| 5 | nucleotide sequence of inverted repeat in genetic construct encoding part of ghKASII-A |
| 6 | cDNA sequence encoding cotton FAD2 from ghFAD2-1 gene. 1362 nucleotides, protein coding region: nucleotides 73-1227 |
| 7 | amino acid sequence of ghFAD2-1 encoded by SEQ ID NO: 6 |
| 8 | *Gossypium hirsutum* mRNA for omega-6 desaturase (FAD2-1) also known as oleoyl-delta12 desaturase. Accession No. X97016 1386 bp, protein coding region: nucleotides 54-1211. Homology with SEQ ID NO: 6 was 96% along the full length of the cDNAs |
| 9 | amino acid sequence of ghFAD2-1 encoded by SEQ ID NO: 8 |
| 10 | EST sequence from *Gossypium hirsutum* (Dowd et al., 2004 (supra)). Accession No. CD486555 |
| 11 | Nucleotide sequence of ghCPA-FAS-1 encoding *Gossypium hirsutum* cyclopropane fatty acid synthase (CPA-FAS-1), Accession No. AY574036, complete cDNA sequence, 2884 bp, protein coding region: nucleotides 33-2654. |
| 12 | amino acid sequence of ghCPA-FAS- encoded by SEQ ID NO: 11 |
| 13 | Nucleotide sequence of ghCPA-FAS-2 encoding *Gossypium hirsutum* cyclopropane fatty acid synthase (CPA-FAS-2), Accession No. AY574037, complete cDNA sequence, 2827 bp, protein coding region: nucleotides 16-2613. |
| 14 | amino acid sequence of ghCPA-FAS-2 encoded by SEQ ID NO: 13 |
| 15 | Nucleotide sequence of ghCPA-FAS-3 encoding *Gossypium hirsutum* cyclopropane fatty acid synthase (CPA-FAS-3), Accession No. AY574038, complete cDNA sequence, 2912 bp, protein coding region: nucleotides 109-2706. |
| 16 | amino acid sequence of ghCPA-FAS-3 encoded by SEQ ID NO: 15 |
| 17 | primer for amplification of KASII |
| 18 | primer for amplification of KASII |
| 19 | primer for amplification of ghKASII-A (Nco-K10S) |
| 20 | primer for amplification of ghKASII-A (Nco-K10A) |
| 21 | primer for amplification of ghKASII-A (Sma-KIR-SA) |
| 22 | nucleotide sequence of Δ9 desaturase (SAD-1) of *Gossypium hirsutum* |
| 23 | amino acid sequence encoded by SEQ ID NO: 22 |

TABLE 7

| Exemplary and Preferred Amino Acid Substitutions | | |
|---|---|---|
| Original Residue | EXEMPLARY SUBSTITUTIONS | PREFERRED SUBSTITUTIONS |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

TABLE 8

| Sequences producing significant alignments with cotton KASII-A (SEQ ID NO: 1) | | | | | | |
|---|---|---|---|---|---|---|
| Accession | Description | Max score | Total score | Query coverage | E value | Max ident |
| DQ987700.1 | *Jatropha curcas* beta-ketoacyl-ACP synthase II mRNA, complete cds | 1314 | 1314 | 68% | 0.0 | 81% |
| AY907522.1 | *Glycine max* plastid 3-keto-acyl-ACP synthase II-B (KASII-B) mRNA, complete cds; nuclear gene for plastid product | 1312 | 1312 | 66% | 0.0 | 82% |
| AY907523.1 | *Glycine max* plastid 3-keto-acyl-ACP synthase II-A (KASII-A) mRNA, complete cds; nuclear gene for plastid product | 1290 | 1290 | 66% | 0.0 | 81% |
| L13241.1 | Castor bean chloroplast beta-ketoacyl-ACP synthase mRNA, complete cds | 1281 | 1281 | 66% | 0.0 | 81% |
| AF244518.1 | *Glycine max* developing seed beta-ketoacyl-ACP synthetase 2 mRNA, complete cds; nuclear gene for proplastid product | 1249 | 1249 | 66% | 0.0 | 81% |
| AF026149.1 | *Perilla frutescens* beta-ketoacyl-ACP synthase II (KAS II) mRNA, complete cds | 1155 | 1155 | 66% | 0.0 | 79% |
| AF060518.1 | *Cuphea pulcherrima* 3-ketoacyl-ACP synthase (Kas4) mRNA, complete cds | 1121 | 1121 | 66% | 0.0 | 78% |
| NM_179557.2 | *Arabidopsis thaliana* FAB1 (FATTY ACID BIOSYNTHESIS 1); fatty-acid synthase (FAB1) mRNA, complete cds | 1083 | 1083 | 63% | 0.0 | 78% |
| NM_106154.2 | *Arabidopsis thaliana* FAB1 (FATTY ACID BIOSYNTHESIS 1); fatty-acid synthase (FAB1) mRNA, complete cds | 1083 | 1083 | 63% | 0.0 | 78% |
| AF318307.1 | *Arabidopsis thaliana* beta-ketoacyl-ACP synthetase 2 mRNA, complete cds; nuclear gene for plastid product | 1083 | 1083 | 63% | 0.0 | 78% |
| AF419598.1 | *Arabidopsis thaliana* At1g74960/F9E10_19 mRNA, complete cds | 1083 | 1083 | 63% | 0.0 | 78% |
| AY054196.1 | *Arabidopsis thaliana* At1g74960/F9E10_19 mRNA, complete cds | 1083 | 1083 | 63% | 0.0 | 78% |
| AY097344.1 | *Arabidopsis thaliana* At1g74960/F9E10_19 mRNA, complete cds | 1079 | 1079 | 63% | 0.0 | 78% |

TABLE 8-continued

| Sequences producing significant alignments with cotton KASII-A (SEQ ID NO: 1) | | | | | | |
|---|---|---|---|---|---|---|
| Accession | Description | Max score | Total score | Query coverage | E value | Max ident |
| AY081285.1 | *Arabidopsis thaliana* putative 3-ketoacyl-ACP synthase (At1g74960) mRNA, complete cds | 1077 | 1077 | 63% | 0.0 | 78% |
| AF412045.1 | *Arabidopsis thaliana* At1g74960/F9E10_19 mRNA, complete cds | 1076 | 1076 | 63% | 0.0 | 78% |
| AF220453.2 | *Elaeis guineensis* beta-ketoacyl-ACP synthase II mRNA, complete cds | 1067 | 1067 | 65% | 0.0 | 78% |
| XXU67316.1 | *Cuphea wrightii* beta-ketoacyl-ACP synthase II (CwKASII2) mRNA, complete cds | 1061 | 1061 | 66% | 0.0 | 77% |
| AF244520.1 | *Brassica napus* developing seed beta-ketoacyl-ACP synthetase 2 mRNA, complete cds; nuclear gene for proplastid product | 1058 | 1058 | 63% | 0.0 | 78% |
| U67317.1 | *Cuphea wrightii* beta-ketoacyl-ACP synthase II (CwKASHII1) mRNA, complete cds | 1054 | 1054 | 65% | 0.0 | 77% |
| AJ344250.1 | *Cuphea lanceolata* mRNA for beta-ketoacyl-ACP synthase IV (kas4 gene) | 1043 | 1043 | 66% | 0.0 | 77% |
| DQ835562.1 | *Helianthus annuus* plastid 3-keto-acyl-ACP synthase II (KASII) mRNA, complete cds; nuclear gene for plastid product | 1023 | 1023 | 62% | 0.0 | 78% |
| AF060519.2 | *Cuphea hookeriana* 3-ketoacyl-ACP synthase (Kas4) mRNA, complete cds | 1000 | 1000 | 66% | 0.0 | 76% |
| AF242848.1 | *Brassica napus* beta-ketoacyl-acyl carrier protein synthase mRNA, partial cds | 978 | 978 | 62% | 0.0 | 77% |
| Z34268.1 | *H. vulgare* (pMaW22) mRNA for beta-ketoacyl-ACP synthase | 949 | 949 | 63% | 0.0 | 76% |
| CT829616.1 | *Oryza sativa* (*indica* cultivar-group) cDNA clone: OSIGCRA222A19, full insert sequence | 895 | 895 | 66% | 0.0 | 75% |
| NM_001066809.1 | *Oryza sativa* (*japonica* cultivar-group) Os07g0616200 (Os07g0616200) mRNA, complete cds | 895 | 895 | 66% | 0.0 | 75% |
| AK067275.1 | *Oryza sativa Japonica* Group cDNA clone: J013098L18, full insert sequence | 895 | 895 | 66% | 0.0 | 75% |
| Z34267.1 | *H. vulgare* (pMaW20) pseudo mRNA for beta-ketoacyl-ACP synthase (partial) | 892 | 892 | 59% | 0.0 | 76% |
| Z34269.1 | *H. vulgare* (pMaW25) mRNA for beta-ketoacyl-ACP synthase | 863 | 863 | 60% | 0.0 | 75% |
| AY106155.1 | *Zea mays* PCO093981 mRNA sequence | 859 | 859 | 63% | 0.0 | 75% |
| AY103998.1 | *Zea mays* PCO121523 mRNA sequence | 859 | 859 | 62% | 0.0 | 75% |
| BT018837.1 | *Zea mays* clone EL01N0552G07.d mRNA sequence | 818 | 818 | 62% | 0.0 | 74% |
| Z34266.1 | *H. vulgare* (pMaW21) pseudo mRNA for beta-ketoacyl-ACP synthase (partial) | 801 | 801 | 51% | 0.0 | 77% |
| XM_001773086.1 | *Physcomitrella patens* subsp. *patens* predicted protein (PHYPADRAFT_87584) mRNA, complete cds | 737 | 737 | 62% | 0.0 | 73% |
| XM_001768868.1 | *Physcomitrella patens* subsp. *patens* predicted protein (PHYPADRAFT_214865) mRNA, complete cds | 722 | 722 | 61% | 0.0 | 73% |
| XM_001768942.1 | *Physcomitrella patens* subsp. *patens* predicted protein (PHYPADRAFT_230580) mRNA, complete cds | 672 | 672 | 62% | 0.0 | 72% |
| XM_001763254.1 | *Physcomitrella patens* subsp. *patens* predicted protein (PHYPADRAFT_182892) mRNA, complete cds | 652 | 652 | 62% | 0.0 | 71% |
| AY089977.1 | *Elaeis oleifera* beta-ketoacyl-ACP synthase II mRNA, partial cds | 619 | 619 | 35% | 1e−173 | 79% |
| AY845865.1 | *Betula pendula* plastid beta-ketoacyl ACP synthase mRNA, partial cds; nuclear gene for plastid product | 578 | 578 | 26% | 4e−161 | 84% |
| AY805139.1 | *Helianthus annuus* cultivar Mammoth ketoacyl-ACP synthase II (KASII) mRNA, partial cds | 554 | 554 | 34% | 4e−154 | 78% |
| BT016639.1 | *Zea mays* clone Contig472 mRNA sequence | 260 | 260 | 27% | 1e−65 | 71% |
| AY805138.1 | *Helianthus annuus* cultivar Mammoth ketoacyl-ACP synthase II-like (KASII) mRNA, partial sequence | 255 | 255 | 21% | 5e−64 | 74% |
| AF243182.1 | *Glycine max* beta-ketoacyl-ACP synthetase I mRNA, complete cds; nuclear gene for proplastid product | 248 | 248 | 27% | 8e−62 | 70% |
| EF177175.1 | *Helianthus annuus* plastid 3-keto-acyl-ACP synthase I (KASI) mRNA, complete cds; nuclear gene for plastid product | 241 | 241 | 27% | 1e−59 | 70% |
| AK230286.1 | *Arabidopsis thaliana* mRNA for hypothetical protein, complete cds, clone: RAFL24-06-B17 | 230 | 230 | 27% | 2e−56 | 70% |
| NM_123998.2 | *Arabidopsis thaliana* KAS I (3-KETOACYL-ACYL CARRIER PROTEIN SYNTHASE I); fatty-acid synthase (KAS I) mRNA, complete cds | 230 | 230 | 27% | 2e−56 | 70% |
| AY123979.1 | *Arabidopsis thaliana* AT5g46290/MPL12_7 mRNA, complete cds | 230 | 230 | 27% | 2e−56 | 70% |
| AY094005.1 | *Arabidopsis thaliana* AT5g46290/MPL12_7 mRNA, complete cds | 230 | 230 | 27% | 2e−56 | 70% |
| AY087843.1 | *Arabidopsis thaliana* clone 38900 mRNA, complete sequence | 230 | 230 | 27% | 2e−56 | 70% |
| AY037261.1 | *Arabidopsis thaliana* AT5g46290/MPL12_7 mRNA, complete cds | 230 | 230 | 27% | 2e−56 | 70% |
| BX830997.1 | *Arabidopsis thaliana* Full-length cDNA Complete sequence from clone GSLTLS47ZD12 of Adult vegetative tissue of strain col-0 of *Arabidopsis thaliana* (thale cress) | 230 | 230 | 27% | 2e−56 | 70% |
| AF243183.1 | *Glycine max* beta-ketoacyl-ACP synthetase I-2 mRNA, complete cds; nuclear gene for proplastid product | 230 | 230 | 27% | 2e−56 | 69% |
| NM_001063588.1 | *Oryza sativa* (*japonica* cultivar-group) Os06g0196600 (Os06g0196600) mRNA, complete cds | 228 | 228 | 27% | 8e−56 | 70% |
| AK060515.1 | *Oryza sativa Japonica* Group cDNA clone: 001-020-A01, full insert sequence | 228 | 228 | 27% | 8e−56 | 70% |
| U24177.1 | *Arabidopsis thaliana* 3-ketoacyl-acyl carrier protein synthase I (KAS I) mRNA, complete cds | 228 | 228 | 27% | 8e−56 | 70% |
| DQ987699.1 | *Jatropha curcas* beta-ketoacyl-ACP synthase I mRNA, complete cds | 226 | 226 | 28% | 3e−55 | 70% |
| EF599102.1 | *Ricinus communis* plastid 3-keto-acyl-ACP synthase II (KASII) gene, complete cds; nuclear gene for plastid product | 223 | 1389 | 68% | 3e−54 | 91% |
| AP008212.1 | *Oryza sativa* (*japonica* cultivar-group) genomic DNA, chromosome 6 | 221 | 269 | 18% | 1e−53 | 93% |
| AP003510.3 | *Oryza sativa Japonica* Group genomic DNA, chromosome 6, PAC clone: P0528E04 | 221 | 221 | 16% | 1e−53 | 74% |
| AF026148.1 | *Perilla frutescens* beta-ketoacyl-ACP synthase I (KAS I) mRNA, complete cds | 221 | 221 | 27% | 1e−53 | 69% |
| AM460084.2 | *Vitis vinifera* contig VV78X215898.9, whole genome shotgun sequence | 212 | 1395 | 64% | 6e−51 | 90% |

TABLE 8-continued

Sequences producing significant alignments with cotton KASII-A (SEQ ID NO: 1)

| Accession | Description | Max score | Total score | Query coverage | E value | Max ident |
|---|---|---|---|---|---|---|
| DQ141237.1 | *Cuphea pulcherrima* plastid 3-ketoacyl-ACP synthase I (KASI) mRNA, complete cds; nuclear gene for plastid product | 208 | 208 | 31% | 7e−50 | 67% |
| L13242.1 | Castor bean chloroplast beta-ketoacyl-ACP synthase (50 kDa synthase) mRNA, complete cds | 208 | 208 | 28% | 7e−50 | 69% |
| AK249874.1 | *Hordeum vulgare* subsp. *vulgare* cDNA clone: FLbaf58p11, mRNA sequence | 205 | 205 | 27% | 9e−49 | 69% |
| AC013258.5 | *Arabidopsis thaliana* chromosome 1 BAC F9E10 genomic sequence, complete sequence | 199 | 1085 | 54% | 4e−47 | 90% |
| AC008263.2 | *Arabidopsis thaliana* chromosome 1 BAC F25A4 sequence, complete sequence | 199 | 1085 | 54% | 4e−47 | 90% |
| AY109499.1 | *Zea mays* CL2801_1 mRNA sequence | 196 | 196 | 27% | 5e−46 | 68% |
| AF085148.1 | *Capsicum chinense* strain habanero 3-oxoacyl-[acyl-carrier-protein] synthase (Kas) mRNA, complete cds | 196 | 196 | 39% | 5e−46 | 66% |
| AC146651.10 | *Medicago truncatula* clone mth2-113d3, complete sequence | 194 | 251 | 25% | 2e−45 | 72% |
| AM459157.2 | *Vitis vinifera* contig VV78X267237.9, whole genome shotgun sequence | 192 | 237 | 21% | 6e−45 | 73% |
| AF244519.1 | *Brassica napus* developing seed beta-ketoacyl-ACP synthetase 1 mRNA, complete cds; nuclear gene for proplastid product | 192 | 192 | 27% | 6e−45 | 68% |
| AM441408.2 | *Vitis vinifera* contig VV78X004929.9, whole genome shotgun sequence | 187 | 1231 | 62% | 2e−43 | 87% |
| AP004472.1 | *Lotus japonicus* genomic DNA, chromosome 4, clone: LjT17P02, TM0006, complete sequence | 187 | 1062 | 51% | 2e−43 | 91% |
| AC215389.2 | *Solanum lycopersicum* chromosome 2 clone C02HBa0122F06, complete sequence | 181 | 251 | 22% | 1e−41 | 72% |
| AJ718354.1 | *Nicotiana tabacum* cDNA-AFLP-fragment BSTT43-24-550, cultivar Bright Yellow 2 | 181 | 181 | 19% | 1e−41 | 70% |
| AP010266.1 | *Solanum lycopersicum* DNA, chromosome 8, clone: C08SLm0118A12, complete sequence | 178 | 229 | 22% | 1e−40 | 72% |
| AP009514.1 | *Solanum lycopersicum* DNA, chromosome 8, clone: C08HBa0014G04, complete sequence | 178 | 229 | 22% | 1e−40 | 72% |
| AB010698.1 | *Arabidopsis thaliana* genomic DNA, chromosome 5, P1 clone: MPL12 | 178 | 229 | 25% | 1e−40 | 72% |
| AC144483.10 | *Medicago truncatula* chromosome 8 clone mth2-12f13, complete sequence | 174 | 1037 | 55% | 1e−39 | 89% |
| EU664594.1 | *Daucus carota* subsp. *sativus* clone DCG333 RFLP marker genomic sequence | 169 | 442 | 24% | 6e−38 | 86% |
| EF613260.1 | *Ricinus communis* plastid 3-keto-acyl-ACP synthase I (KASI) gene, complete cds; nuclear gene for plastid product | 165 | 215 | 23% | 8e−37 | 71% |
| AC189210.1 | *Brassica rapa* subsp. *pekinensis* clone KBrB007O13, complete sequence | 165 | 213 | 23% | 8e−37 | 72% |
| AC213147.1 | *Oryza officinalis* clone OO_Ba0112L09, complete sequence | 163 | 729 | 43% | 3e−36 | 84% |
| AP008213.1 | *Oryza sativa* (*japonica* cultivar-group) genomic DNA, chromosome 7 | 163 | 794 | 42% | 3e−36 | 85% |
| AP004988.3 | *Oryza sativa Japonica* Group genomic DNA, chromosome 7, BAC clone: B1056G08 | 163 | 794 | 42% | 3e−36 | 85% |
| M60410.1 | *Hordeum vulgare* beta-ketoacyl-ACP synthase I (Kas12) mRNA, complete cds | 161 | 161 | 22% | 9e−36 | 68% |
| CT834060.1 | *Oryza sativa* (*indica* cultivar-group) cDNA clone: OSIGCPI237D08, full insert sequence | 159 | 159 | 20% | 3e−35 | 68% |
| NM_001059439.1 | *Oryza sativa* (*japonica* cultivar-group) Os04g0445700 (Os04g0445700) mRNA, complete cds | 159 | 159 | 20% | 3e−35 | 68% |
| AK120916.1 | *Oryza sativa Japonica* Group cDNA clone: J023034I15, full insert sequence | 159 | 159 | 20% | 3e−35 | 68% |
| AK071888.1 | *Oryza sativa Japonica* Group cDNA clone: J013046E01, full insert sequence | 159 | 159 | 20% | 3e−35 | 68% |
| XM_001762635.1 | *Physcomitrella patens* subsp. *patens* predicted protein (PHYPADRAFT_125854) mRNA, complete cds | 158 | 158 | 34% | 1e−34 | 66% |
| CR855182.1 | *Oryza sativa* genomic DNA, chromosome 4, BAC clone: OSIGBa0140O07, complete sequence | 149 | 149 | 15% | 6e−32 | 70% |
| AP008210.1 | *Oryza sativa* (*japonica* cultivar-group) genomic DNA, chromosome 4 | 149 | 191 | 16% | 6e−32 | 100% |
| AL731593.2 | *Oryza sativa* genomic DNA, chromosome 4, BAC clone: OSJNBa0027P08, complete sequence | 149 | 149 | 15% | 6e−32 | 70% |
| XM_001416432.1 | *Ostreococcus lucimarinus* CCE9901 predicted protein (OSTLU_35878) mRNA, complete cds | 143 | 143 | 22% | 3e−30 | 67% |
| CP000582.1 | *Ostreococcus lucimarinus* CCE9901 chromosome 2, complete sequence | 143 | 143 | 22% | 3e−30 | 67% |
| M95172.1 | *Hordeum vulgare* chloroplast beta-ketoacyl-ACP sythase I isozyme (Kas12) gene, exons 1 through 7 and complete cds | 141 | 141 | 15% | 9e−30 | 70% |
| NM_001036941.1 | *Arabidopsis thaliana* KAS I (3-KETOACYL-ACYL CARRIER PROTEIN SYNTHASE I); fatty-acid synthase (KAS I) mRNA, complete cds | 138 | 138 | 17% | 1e−28 | 70% |
| AE017160.1 | *Chlamydophila pneumoniae* TW-183, section 4 of 4 of the complete genome | 138 | 138 | 15% | 1e−28 | 70% |
| BA000008.3 | *Chlamydophila pneumoniae* J138 genomic DNA, complete sequence | 138 | 138 | 15% | 1e−28 | 70% |

BIBLIOGRAPHY

Almeida and Allshire, *Trends Cell Biol.* 15: 251-258, 2005.

Altschul et al., *Nucleic Acids Res.* 25: 3389, 1997.

Ausubel et al., (eds.), *Current Protocols in Molecular Biology*, John Wiley & Sons, NY, 6.3.1-6.3.6., 1989.

Ausubel et al., *Current Protocols in Molecular Biology*, John Wiley & Sons hie, 1994-1998, Chapter 15.

Barker et al., *Plant Mol. Biol.,* 2: 235-350, 1983.

Bechtold et al., *C.R. Acad. Sci. Paris,* 316: 1194, 1993.

Bevan et al., *Nucl. Acid Res.,* 11: 369, 1983.

Birch, *Ann Rev Plant Physiol Plant Mol Biol.* 48: 297-326, 1997.

Bligh et al., *Canadian Journal of Biochemistry and Physiology* 37: 911-917, 1959.

Bourque, *Plant Science,* 105: 125-149, 1995.

Cherry, *J. Am. Oil Chem. Soc.* 60: 360-367, 1983.

Cho et al., *Plant Molecular Biology Reporter* 13: 255-269, 1995.

Comai et al., *Plant J.* 37: 778-786, 2004.

De Framond, *Biotechnology,* 1: 262, 1983.

Dowd et al., *Molecular Plant-Microbe Interactions.* 17: 654-667, 2004.

Folch et al., *J. Biol. Chem.* 226: 497, 1957.

Fuller et al., *J. Food Sci.* 31: 477-480, 1966.

Garfinkel et al., *Cell,* 27: 143-153, 1983.
Greve, *J. Mol. Appl. Genet.,* 1:499-511, 1983.
Harayama, *Trends Biotechnol.* 16: 76-82, 1998.
Hartmann and Endres, *Manual of Antisense Methodology*, Kluwer, 1999.
Haseloff and Gerlach, *Nature* 334: 585-591, 1988.
Henikoff et al., *Plant Physiol.* 135: 630-636, 2004.
Hinchee et al., *Biotech.* 6: 915, 1988.
Hoekema et al., *Nature,* 303: 179, 1983.
Hutchins et al., *Journal of American Oil Chemists Society* 45: 397-399, 1968.
Johnson et al., *Nature* 214: 1244-1245, 1967.
Joshi, *Nucl. Acid Res.* 15: 6643, 1987.
Kargiotidou et al., *Journal of Experimental Botany* 2008 59(8): 2043-2056, 2008.
Khandjian, *Bio/Technology,* 5: 165-167, 1987.
Klein et al., *Nature,* 327: 70, 1987.
Liu et al., *Plant Physiol.* 120:339, 1999b.
Liu et al., *Plant Physiol.* 129: 1732-1743, 2002.
Liu et al., *Australian Journal of Plant Physiology* 26: 101-106, 1999a.
McPherson and Moller (Ed), BIOS Scientific Publishers Ltd, Oxford, 2000.
Medberry et al., *Plant Cell,* 4: 185-192, 1992.
Medberry et al., *Plant J.* 3: 619-626, 1993.
Merker and Mattil (1965). U.S. Pat. No. 3,201,431.
Millar and Waterhouse, *Fund Integr Genomics,* 5: 129-135, 2005.
Mojovic et al., *Enzyme Microb Technol.* 15: 438-443, 1993.
Mounts et al., *J. Am. Oil Chem. Soc.* 65: 624-628, 1998.
Murashige and Skoog, *Physiologia Plantarum,* 15: 473-497, 1962.
Needleman and Wunsch, *J. Mol. Biol.* 48: 443-453, 1970.
Niedz et al., *Plant Cell Reports,* 14: 403, 1995.
O'Brien, Cottonseed Oil. In: F. D. Gunstone (Ed.) Vegetable Oils in Food Technology: Composition, Properties and Uses. Blackwell Publishing, Oxford, pp. 203-230, 2002.
Ow et al., *Science,* 234: 856, 1986.
Pasquinelli et al. *Curr Opin Genet Develop* 15: 200-205, 2005.
Perriman et al., *Gene,* 113: 157-163, 1992.
Pirtle et al., *Biochim. Biophys. Acta* 1522: 122-129, 2001.
Prasher et al., *Biochem. Biophys. Res. Comm.* 126: 1259-68, 1985.
Roehm et al., *Lipids* 5: 80-84, 1970.
Salomon et al., *EMBO J.,* 3: 141-146, 1984.
Sambrook et al., *Molecular Cloning: A Laboratory Manual* (*2nd Ed*). Cold Spring Harbour Laboratory, Cold Spring Harbour, N.Y. 1989.
Senior, *Biotech. Genet. Engin. Revs.* 15: 79-119, 1998.
Shenstone and Vickery, *Nature* 190: 68-169, 1961.
Shippy et al., *Mol. Biotech.* 12: 117-129, 1999.
Slade and Knauf, *Transgenic Res.* 14: 109-115, 2005.
Smith et al., *Nature,* 407: 319-320, 2000.
Stalker et al., *Science,* 242: 419, 1988.
Millet et al., *J. Biol. Chem.* 263: 12500, 1988.
Waterhouse et al., *Proc. Natl. Acad. Sci. U.S.A.* 95: 13959-13964, 1998.
Wollett and Dietshy, *Amer. J. Clin. Nutr.* 60: 991-96, 1994.
Zwar and Chandler, *Planta* 197: 39-48, 1995.

The invention claimed is:

1. A process for producing seed oil, comprising the steps of:

(i) obtaining cotton seed, wherein the cotton seed has a reduced level relative to wild-type seed of a protein having amino acids in a sequence that is at least 95% identical to either the amino acid sequence set forth as SEQ ID NO: 2 or SEQ ID NO: 4, wherein said reduction is achieved by directly targeting a gene encoding said protein or a RNA product of said gene, and wherein the cotton seed is capable of producing a male-fertile cotton plant, wherein in the oil of the seed 28% to about 80% by weight of the total fatty acid content is C16 fatty acid, about 3% to about 33% is stearic acid, about 1% to about 40% is oleic acid, about 4% to about 50% is linoleic acid, and 0% to about 10% is linolenic acid;

(ii) extracting the oil from the seed; and (iii) recovering the seed oil.

2. The process of claim 1, wherein 0% to about 16% of the total fatty acid content is palmitoleic acid.

3. The process of claim 1, wherein 0% to about 4% of the total fatty acid content is C16:2 fatty acid.

4. The process of claim 1, wherein 30% to about 80% of the total fatty acid content is C16 fatty acid.

5. The process of claim 1, wherein at least 95% of the total fatty acid content in the seed oil is in the form of triacylglycerols.

6. The process of claim 1, wherein step (ii) comprises crushing the seed.

7. The process of claim 1, wherein step (iii) comprises purifying the seed oil.

8. Cotton seed, wherein the cotton seed has a reduced level relative to wild-type seed of a protein having amino acids in a sequence that is at least 95% identical to either the amino acid sequence set forth as SEQ ID NO: 2 or SEQ ID NO: 4, wherein said reduction is achieved by directly targeting a gene encoding said protein or a RNA product of said gene, and wherein the cotton seed is capable of producing a male-fertile cotton plant, wherein in its seed oil 28% to about 80% of the total fatty acid content is C16 fatty acid, about 3% to about 33% is stearic acid, about 1% to about 40% is oleic acid, about 4% to about 50% is linoleic acid, and 0% to about 10% is linolenic acid.

9. The seed of claim 8, wherein 0% to about 16% of the total fatty acid content is palmitoleic acid.

10. The seed of claim 8, wherein 0% to about 4% of the total fatty acid content is C16:2 fatty acid.

11. The seed of claim 8, wherein 30% to about 80% of the total fatty acid content is C16 fatty acid.

12. The seed of claim 8, wherein at least 95% of the total fatty acid content in the seed oil is in the form of triacylglycerols.

13. The process of claim 1, wherein the total fatty acid content of the seed comprises 11% palmitoleic acid.

14. The process of claim 1, wherein the seed is homozygous for a silencing construct targeting the ghKASII-A gene.

15. The seed of claim 8, wherein the total fatty acid content of the seed comprises 11% palmitoleic acid.

16. The seed of claim 8, wherein the seed is homozygous for a silencing construct targeting the ghKASII-A gene.

17. The process of claim 1, wherein the cotton seed has a reduced level of a protein having amino acids in a sequence that is identical to either the amino acid sequence set forth as SEQ ID NO: 2 or SEQ ID NO: 4.

18. The seed of claim 8, wherein the seed has a reduced level of a protein having amino acids in a sequence that is identical to either the amino acid sequence set forth as SEQ ID NO: 2 or SEQ ID NO: 4.

19. The process of claim 1, wherein directly targeting the gene encoding said protein or the RNA product of said gene is achieved by an antisense technique, RNA interference, a ribozyme, cosuppression, or mutagenesis.

20. The seed of claim 8, wherein directly targeting the gene encoding said protein or the RNA product of said gene is achieved by an antisense technique, RNA interference, a ribozyme, cosuppression, or mutagenesis.

* * * * *